United States Patent
Yee et al.

(10) Patent No.: US 12,202,877 B2
(45) Date of Patent: Jan. 21, 2025

(54) T CELL RECEPTORS WITH MAGE-B2 SPECIFICITY AND USES THEREOF

(71) Applicant: Board of Regents, The University of Texas System, Austin, TX (US)

(72) Inventors: Cassian Yee, Houston, TX (US); Ke Pan, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1009 days.

(21) Appl. No.: 17/048,748

(22) PCT Filed: Apr. 19, 2019

(86) PCT No.: PCT/US2019/028239
§ 371 (c)(1),
(2) Date: Oct. 19, 2020

(87) PCT Pub. No.: WO2019/204683
PCT Pub. Date: Oct. 24, 2019

(65) Prior Publication Data
US 2021/0363215 A1     Nov. 25, 2021

Related U.S. Application Data

(60) Provisional application No. 62/660,083, filed on Apr. 19, 2018.

(51) Int. Cl.
| | | |
|---|---|---|
| C07K 16/00 | (2006.01) | |
| A61K 39/00 | (2006.01) | |
| C07K 14/725 | (2006.01) | |
| C07K 16/28 | (2006.01) | |
| C12N 5/0783 | (2010.01) | |
| A61K 38/00 | (2006.01) | |

(52) U.S. Cl.
CPC ...... *C07K 14/7051* (2013.01); *A61K 39/4611* (2023.05); *A61K 39/4632* (2023.05); *A61K 39/464486* (2023.05); *C07K 16/2833* (2013.01); *C12N 5/0636* (2013.01); *A61K 38/00* (2013.01); *A61K 2039/54* (2013.01); *A61K 2239/55* (2023.05); *C07K 16/2818* (2013.01); *C07K 2317/35* (2013.01); *C07K 2317/565* (2013.01); *C07K 2319/30* (2013.01)

(58) Field of Classification Search
CPC ............ C07K 14/7051; C07K 16/2833; C07K 2317/565; C07K 16/30; A61K 39/00119
See application file for complete search history.

(56) References Cited

U.S. PATENT DOCUMENTS

| | | |
|---|---|---|
| 2013/0273647 A1 | 10/2013 | Sahin et al. |
| 2013/0274203 A1 | 10/2013 | Morgan et al. |
| 2018/0000913 A1 | 1/2018 | Hacohen et al. |
| 2018/0044631 A1 | 2/2018 | Riken |
| 2018/0164315 A1 | 6/2018 | Alten et al. |

FOREIGN PATENT DOCUMENTS

| | | | | |
|---|---|---|---|---|
| DE | 10 2016 123 859 | | 3/2018 | |
| WO | WO 2007-131092 | | 11/2007 | |
| WO | WO 2012/038055 | | 3/2012 | |
| WO | WO 2012/054825 | | 4/2012 | |
| WO | WO 2013/039889 | | 3/2013 | |
| WO | WO 2014/043441 | | 3/2014 | |
| WO | WO 2017/148888 | | 9/2017 | |
| WO | WO 2017/174822 | | 10/2017 | |
| WO | WO 2017/174823 | | 10/2017 | |
| WO | WO 2018-055140 | | 3/2018 | |
| WO | WO 2018/058002 | | 3/2018 | |
| WO | WO2018162563 A1 | * | 3/2018 | ........... C12N 5/0636 |
| WO | WO 2018/067618 | | 4/2018 | |
| WO | WO2019036688 A1 | * | 2/2019 | ......... A61K 39/0011 |

OTHER PUBLICATIONS

Robbins, P.F. et al., Single and Dual Amino Acid Substitutions in TCR CDRs Can Enhance Antigen-Specific T Cell Functions. J Immunol May 1, 2008; 180 (9): 6116-6131 (Year: 2008).*
Shamel, W.W.A. et al. Coexistence of multivalent and monovalent TCRs explains high sensitivity and wide range of response. J Exp Med 2005 (Year: 2005).*
Office Action issued in Japanese Application No. 2020-556863, mailed Feb. 2, 2023, and English translation thereof.
Barnea et al., "Analysis of endogenous peptides bound by soluble MHC class I molecules: a novel approach for identifying tumor-specific antigens", Eur. J. Immunol., 32: 213-222 (2002).
International Search Report and Written Opinion for PCT/US2019/028239 dated Jul. 22, 2019, 17 pages.
International Preliminary Report on Patentability for PCT/US2019/028239 dated Oct. 20, 2020, 9 pages.
Office Action issued in Chinese Application No. 201980037254.1, mailed Oct. 18, 2022.
Shraibman et al., "HLA peptides derived from tumor antigens induced by inhibition of DNA methylation for development of drug of drug-facilitated immunotherapy", Mol Cell Proteomics, 15(9):3058-70 (2016).
Supplementary Partial European Search Report for EP 19787925 dated Dec. 21, 2021, 13 pages.
Supplementary European Search Report for EP 19787925 dated May 16, 2022, 12 pages.
Van Rhijn Ildiko et al., "CD1d-restricted T cell activation by nonlipidic small molecules", Proceedings of the National Academy of Sciences, vol. 101, No. 37, pp. 13578-13583, Sep. 14, 2004.

* cited by examiner

*Primary Examiner* — Daniel E Kolker
*Assistant Examiner* — Estella M. Gustilo
(74) *Attorney, Agent, or Firm* — Parker Highlander PLLC

(57) ABSTRACT

The present disclosure provides methods for generating MAGE-B2 specific T cells and compositions comprising engineered MAGE-B2-specific T cell receptors. Further provided are methods of treating cancer comprising administering the MAGE-B2-specific T cells.

18 Claims, 26 Drawing Sheets
Specification includes a Sequence Listing.

SEQUENCE LISTING

```
<160> NUMBER OF SEQ ID NOS: 45

<210> SEQ ID NO 1
<211> LENGTH: 10
<212> TYPE: PRT
<213> ORGANISM: Artificial sequence
<220> FEATURE:
<223> OTHER INFORMATION: Synthetic amino acid

<400> SEQUENCE: 1

Gly Val Tyr Asp Gly Glu Glu His Ser Val
1               5                   10

<210> SEQ ID NO 2
<211> LENGTH: 813
<212> TYPE: DNA
<213> ORGANISM: Artificial sequence
<220> FEATURE:
<223> OTHER INFORMATION: Synthetic oligonucleotide

<400> SEQUENCE: 2
atgaactatt ctccaggctt agtatctctg atactcttac tgcttggaag aacccgtgga      60
aattcagtga cccagatgga agggccagtg actctctcag aagaggcctt cctgactata     120
aactgcacgt acacagccac aggatacccc tcccttttct ggtatgtcca atatcctgga     180
gaaggtctac agctcctcct gaaagccacg aaggctgatg acaagggaag caacaaaggt     240
tttgaagcca cataccgtaa agaaaccact tctttccact tggagaaagg ctcagttcaa     300
gtgtcagact cagcggtgta cttctgtgct ctgaccaacg actacaagct cagctttgga     360
gccggaacca cagtaactgt aagagcaaat atccagaacc ctgaccctgc cgtgtaccag     420
ctgagagact ctaaatccag tgacaagtct gtctgcctat tcaccgattt tgattctcaa     480
acaaatgtgt cacaaagtaa ggattctgat gtgtatatca cagacaaaac tgtgctagac     540
atgaggtcta tggacttcaa gagcaacagt gctgtggcct ggagcaacaa atctgacttt     600
gcatgtgcaa acgccttcaa caacagcatt attccagaag acaccttctt ccccagccca     660
gaaagttcct gtgatgtcaa gctggtcgag aaaagctttg aaacagatac gaacctaaac     720
tttcaaaacc tgtcagtgat tgggttccga atcctcctcc tgaaagtggc cgggtttaat     780
ctgctcatga cgctgcggct gtggtccagc tga                                  813

<210> SEQ ID NO 3
<211> LENGTH: 220
<212> TYPE: PRT
<213> ORGANISM: Artificial sequence
<220> FEATURE:
<223> OTHER INFORMATION: Synthetic amino acid

<400> SEQUENCE: 3

Ser Leu Phe Trp Tyr Val Gln Tyr Pro Gly Glu Gly Leu Gln Leu Leu
1               5                   10                  15

Leu Lys Ala Thr Lys Ala Asp Asp Lys Gly Ser Asn Lys Gly Phe Glu
            20                  25                  30
```

Ala Thr Tyr Arg Lys Glu Thr Thr Ser Phe His Leu Glu Lys Gly Ser
                35                  40                  45

Val Gln Val Ser Asp Ser Ala Val Tyr Phe Cys Ala Leu Thr Asn Asp
 50                  55                  60

Tyr Lys Leu Ser Phe Gly Ala Gly Thr Thr Val Thr Val Arg Ala Asn
 65                  70                  75                  80

Ile Gln Asn Pro Asp Pro Ala Val Tyr Gln Leu Arg Asp Ser Lys Ser
                85                  90                  95

Ser Asp Lys Ser Val Cys Leu Phe Thr Asp Phe Asp Ser Gln Thr Asn
                100                 105                 110

Val Ser Gln Ser Lys Asp Ser Asp Val Tyr Ile Thr Asp Lys Thr Val
                115                 120                 125

Leu Asp Met Arg Ser Met Asp Phe Lys Ser Asn Ser Ala Val Ala Trp
                130                 135                 140

Ser Asn Lys Ser Asp Phe Ala Cys Ala Asn Ala Phe Asn Asn Ser Ile
145                 150                 155                 160

Ile Pro Glu Asp Thr Phe Phe Pro Ser Pro Glu Ser Ser Cys Asp Val
                165                 170                 175

Lys Leu Val Glu Lys Ser Phe Glu Thr Asp Thr Asn Leu Asn Phe Gln
                180                 185                 190

Asn Leu Ser Val Ile Gly Phe Arg Ile Leu Leu Leu Lys Val Ala Gly
                195                 200                 205

Phe Asn Leu Leu Met Thr Leu Arg Leu Trp Ser Ser
                210                 215                 220

<210> SEQ ID NO 4
<211> LENGTH: 930
<212> TYPE: DNA
<213> ORGANISM: Artificial sequence
<220> FEATURE:
<223> OTHER INFORMATION: Synthetic oligonucleotide

<400> SEQUENCE: 4
atgggtcctg ggcttctcca ctggatggcc ctttgtctcc ttggaacagg tcatggggat      60
gccatggtca tccagaaccc aagataccag gttacccagt ttggaaagcc agtgaccctg     120
agttgttctc agactttgaa ccataacgtc atgtactggt accagcagaa gtcaagtcag     180
gccccaaagc tgctgttcca ctactatgac aaagatttta caatgaagc agacacccct     240 gataacttcc aatccaggag gccgaacact tctttctgct tcttgacat ccgctcacca     300 ggcctggggg acgcagccat gtacctgtgt gccaccagca gggcgggag gtacaatgag     360 cagttcttcg ggcagggac acggctcacc gtgctagagg acctgaaaaa cgtgttccca     420
cccgaggtcg ctgtgtttga gccatcagaa gcagagatct cccacaccca aaaggccaca     480
ctggtgtgcc tggccacagg cttcttccct gaccacgtgg agctgagctg gtgggtgaat     540
gggaaggagg tgcacagtgg ggtcagcacg gacccgcagc ccctcaagga gcagcccgcc     600
ctcaatgact ccagatactg cctgagcagc cgcctgaggg tctcggccac cttctggcag     660 aaccccgca accacttccg ctgtcaagtc cagttctacg gctctcgga gaatgacgag     720 tggacccagg atagggccaa acccgtcacc cagatcgtca gcgccgaggc tgggggtaga     780
gcagactgtg gctttaccct ggtgtcctac cagcaagggg tcctgtctgc caccatcctc     840
tatgagatcc tgctagggaa ggccacccctg tatgctgtgc tggtcagcgc ccttgtgttg     900
atggccatgg tcaagagaaa ggatttctga                                      930

```
<210> SEQ ID NO 5
<211> LENGTH: 309
<212> TYPE: PRT
<213> ORGANISM: Artificial sequence
<220> FEATURE:
<223> OTHER INFORMATION: Synthetic amino acid

<400> SEQUENCE: 5

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
                20                  25                  30

Gln Phe Gly Lys Pro Val Thr Leu Ser Cys Ser Gln Thr Leu Asn His
            35                  40                  45

Asn Val Met Tyr Trp Tyr Gln Gln Lys Ser Ser Gln Ala Pro Lys Leu
        50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Arg Gly Gly Arg Tyr Asn Glu Gln Phe Phe Gly Pro Gly Thr Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Phe
305

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6
```
gccacaggat acccttcc                                              18

<210> SEQ ID NO 7
<211> LENGTH: 6
<212> TYPE: PRT
<213> ORGANISM: Artificial sequence
<220> FEATURE:
<223> OTHER INFORMATION: Synthetic amino acid

<400> SEQUENCE: 7

Ala Thr Gly Tyr Pro Ser
1               5

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
gccacgaagg ctgatgacaa g                                          21

<210> SEQ ID NO 9
<211> LENGTH: 7
<212> TYPE: PRT
<213> ORGANISM: Artificial sequence
<220> FEATURE:
<223> OTHER INFORMATION: Synthetic amino acid

<400> SEQUENCE: 9

Ala Thr Lys Ala Asp Asp Lys
1               5

<210> SEQ ID NO 10
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 10
gctctgacca acgactacaa gctcagc                                    27

<210> SEQ ID NO 11
<211> LENGTH: 9
<212> TYPE: PRT
<213> ORGANISM: Artificial sequence
<220> FEATURE:
<223> OTHER INFORMATION: Synthetic amino acid

<400> SEQUENCE: 11

Ala Leu Thr Asn Asp Tyr Lys Leu Ser
1               5

<210> SEQ ID NO 12
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 12
ttgaaccata acgtc                                                 15

<210> SEQ ID NO 13

```
<211> LENGTH: 5
<212> TYPE: PRT
<213> ORGANISM: Artificial sequence
<220> FEATURE:
<223> OTHER INFORMATION: Synthetic amino acid

<400> SEQUENCE: 13

Leu Asn His Asn Val
1               5

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 14
tactatgaca aagatttt                                               18

<210> SEQ ID NO 15
<211> LENGTH: 6
<212> TYPE: PRT
<213> ORGANISM: Artificial sequence
<220> FEATURE:
<223> OTHER INFORMATION: Synthetic amino acid

<400> SEQUENCE: 15

Tyr Tyr Asp Lys Asp Phe
1               5

<210> SEQ ID NO 16
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 16
gccaccagca ggggcgggag gtacaatgag cagttc                           36

<210> SEQ ID NO 17
<211> LENGTH: 12
<212> TYPE: PRT
<213> ORGANISM: Artificial sequence
<220> FEATURE:
<223> OTHER INFORMATION: Synthetic amino acid

<400> SEQUENCE: 17

Ala Thr Ser Arg Gly Gly Arg Tyr Asn Glu Gln Phe
1               5                   10

<210> SEQ ID NO 18
<211> LENGTH: 822
<212> TYPE: DNA
<213> ORGANISM: Artificial Sequence
<220> FEATURE:
<223> OTHER INFORMATION: Alpha Chain (TRAV10*01)

<400> SEQUENCE: 18
atgaaaaagc atctgacgac cttcttggtg attttgtggc tttattttta taggggaat    60 ggcaaaaacc aagtggagca gagtcctcag tccctgatca tcctggaggg aaagaactgc   120
actcttcaat gcaattatac agtgagcccc ttcagcaact taaggtggta taagcaagat   180
actgggagag gtcctgtttc cctgacaatc atgactttca gtgagaacac aaagtcgaac   240
```

```
ggaagatata cagcaactct ggatgcagac acaaagcaaa gctctctgca catcacagcc    300
tcccagctca gcgattcagc ctcctacatc tgtgtggtga tttcaggctt tcagaaactt    360
gtatttggaa ctggcacccg acttctggtc agtccaaata tccagaaccc tgaccctgcc    420
gtgtaccagc tgagagactc taaatccagt gacaagtctg tctgcctatt caccgatttt    480
gattctcaaa caaatgtgtc acaaagtaag gattctgatg tgtatatcac agacaaaact    540
gtgctagaca tgaggtctat ggacttcaag agcaacagtg ctgtggcctg agcaacaaa    600 tctgactttg catgtgcaaa cgccttcaac aacagcatta ttccagaaga caccttcttc    660
cccagcccag aaagttcctg tgatgtcaag ctggtcgaga aagctttga acagatacg     720 aacctaaact ttcaaaacct gtcagtgatt gggttccgaa tcctcctcct gaaagtggcc    780
gggtttaatc tgctcatgac gctgcggctg tggtccagct aa                      822
```

```
<210> SEQ ID NO 19
<211> LENGTH: 273
<212> TYPE: PRT
<213> ORGANISM: Artificial Sequence
<220> FEATURE:
<223> OTHER INFORMATION: Alpha Chain

<400> SEQUENCE: 19

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
                20                  25                  30

Ile Ile Leu Glu Gly Lys Asn Cys Thr Leu Gln Cys Asn Tyr Thr Val
            35                  40                  45

Ser Pro Phe Ser Asn Leu Arg Trp Tyr Lys Gln Asp Thr Gly Arg Gly
        50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ile Ser Gly Phe Gln Lys Leu Val Phe Gly Thr Gly Thr Arg Leu
        115                 120                 125

Leu Val Ser Pro Asn Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
```

Ser

<210> SEQ ID NO 20
<211> LENGTH: 939
<212> TYPE: DNA
<213> ORGANISM: Artificial Sequence
<220> FEATURE:
<223> OTHER INFORMATION: Beta Chain (TRBV11-3*04)

<400> SEQUENCE: 20

| | | | | | |
|---|---|---|---|---|---|
| atgggtacca | ggctcctctg | ctgggtggcc | ttctgtctcc | tggtggaaga | actcatagaa | 60 |
| gctggagtgg | ttcagtctcc | cagatataag | attatagaga | aaaaacagcc | tgtggctttt | 120 |
| tggtgcaatc | ctatttctgg | ccacaatacc | ctttactggt | accggcagaa | cttgggacag | 180 |
| ggcccggagc | ttctgattcg | atatgagaat | gaggaagcag | tagacgattc | acagttgcct | 240 |
| aaggatcgat | ttctgcaga | gaggctcaaa | ggagtagact | ccactctcaa | gatccagcct | 300 |
| gcagagcttg | gggactcggc | cgtgtatctc | tgtgccagca | gcttccctaa | acagggatcc | 360 |
| tacaatgagc | agttcttcgg | gccagggaca | cggctcaccg | tgctagagga | cctgaaaaac | 420 |
| gtgttcccac | ccgaggtcgc | tgtgtttgag | ccatcagaag | cagagatctc | cacacccaa | 480 |
| aaggccacac | tggtgtgcct | ggccacaggc | ttcttccctg | accacgtgga | gctgagctgg | 540 |
| tgggtgaatg | gaaggaggt | gcacagtggg | gtcagcacgg | accgcagcc | cctcaaggag | 600 |
| cagcccgccc | tcaatgactc | cagatactgc | ctgagcagcc | gcctgagggt | ctcggccacc | 660 |
| ttctggcaga | acccccgcaa | ccacttccgc | tgtcaagtcc | agttctacgg | gctctcggag | 720 |
| aatgacgagt | ggacccagga | tagggccaaa | cccgtcaccc | agatcgtcag | cgccgaggcc | 780 |
| tggggtagag | cagactgtgg | ctttacctcg | gtgtcctacc | agcaagggg | cctgtctgcc | 840 |
| accatcctct | atgagatcct | gctagggaag | gccaccctgt | atgctgtgct | ggtcagcgcc | 900 |
| cttgtgttga | tggccatggt | caagagaaag | gatttctaa | | | 939 |

<210> SEQ ID NO 21
<211> LENGTH: 312
<212> TYPE: PRT
<213> ORGANISM: Artificial Sequence
<220> FEATURE:
<223> OTHER INFORMATION: Beta Chain

<400> SEQUENCE: 21

Met Gly Thr Arg Leu Leu Cys Trp Val Ala Phe Cys Leu Leu Val Glu
1               5                   10                  15

Glu Leu Ile Glu Ala Gly Val Val Gln Ser Pro Arg Tyr Lys Ile Ile
            20                  25                  30

Glu Lys Lys Gln Pro Val Ala Phe Trp Cys Asn Pro Ile Ser Gly His
        35                  40                  45

Asn Thr Leu Tyr Trp Tyr Arg Gln Asn Leu Gly Gln Gly Pro Glu Leu
    50                  55                  60

Leu Ile Arg Tyr Glu Asn Glu Glu Ala Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Glu Leu Gly Asp Ser Ala Val Tyr Leu Cys Ala
            100                 105                 110

Ser Ser Phe Pro Lys Gln Gly Ser Tyr Asn Glu Gln Phe Phe Gly Pro
        115                 120                 125

```
Gly Thr Arg Leu Thr Val Leu Glu Asp Leu Lys Asn Val Phe Pro Pro
            130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Phe
305                 310

<210> SEQ ID NO 22
<211> LENGTH: 18
<212> TYPE: DNA
<213> ORGANISM: Artificial Sequence
<220> FEATURE:
<223> OTHER INFORMATION: Alpha Chain CDR1

<400> SEQUENCE: 22
gtgagcccct tcagcaac                                                 18

<210> SEQ ID NO 23
<211> LENGTH: 6
<212> TYPE: PRT
<213> ORGANISM: Artificial Sequence
<220> FEATURE:
<223> OTHER INFORMATION: Alpha chain CDR1

<400> SEQUENCE: 23

Val Ser Pro Phe Ser Asn
1               5

<210> SEQ ID NO 24
<211> LENGTH: 21
<212> TYPE: DNA
<213> ORGANISM: Artificial Sequence
<220> FEATURE:
<223> OTHER INFORMATION: Alpha chain CDR2

<400> SEQUENCE: 24
atgactttca gtgagaacac a                                             21

<210> SEQ ID NO 25
<211> LENGTH: 7
<212> TYPE: PRT
<213> ORGANISM: Artificial Sequence
```

```
<220> FEATURE:
<223> OTHER INFORMATION: Alpha chain CDR2

<400> SEQUENCE: 25

Met Thr Phe Ser Glu Asn Thr
1               5

<210> SEQ ID NO 26
<211> LENGTH: 30
<212> TYPE: DNA
<213> ORGANISM: Artificial Sequence
<220> FEATURE:
<223> OTHER INFORMATION: Alpha chai CDR3

<400> SEQUENCE: 26
gtggtgattt caggctttca gaaacttgta                                        30

<210> SEQ ID NO 27
<211> LENGTH: 10
<212> TYPE: PRT
<213> ORGANISM: Artificial Sequence
<220> FEATURE:
<223> OTHER INFORMATION: Alpha chain CDR3

<400> SEQUENCE: 27

Val Val Ile Ser Gly Phe Gln Lys Leu Val
1               5                   10

<210> SEQ ID NO 28
<211> LENGTH: 15
<212> TYPE: DNA
<213> ORGANISM: Artificial Sequence
<220> FEATURE:
<223> OTHER INFORMATION: Beta chain CDR1

<400> SEQUENCE: 28
tctggccaca atacc                                                        15

<210> SEQ ID NO 29
<211> LENGTH: 5
<212> TYPE: PRT
<213> ORGANISM: Artificial Sequence
<220> FEATURE:
<223> OTHER INFORMATION: Beta chain CDR1

<400> SEQUENCE: 29

Ser Gly His Asn Thr
1               5

<210> SEQ ID NO 30
<211> LENGTH: 18
<212> TYPE: DNA
<213> ORGANISM: Artificial Sequence
<220> FEATURE:
<223> OTHER INFORMATION: Beta chain CDR2

<400> SEQUENCE: 30
tatgagaatg aggaagca                                                     18

<210> SEQ ID NO 31
<211> LENGTH: 6
<212> TYPE: PRT
<213> ORGANISM: Artificial Sequence
<220> FEATURE:
<223> OTHER INFORMATION: Beta hain CDR2

<400> SEQUENCE: 31
```

Tyr Glu Asn Glu Glu Ala
1               5

<210> SEQ ID NO 32
<211> LENGTH: 42
<212> TYPE: DNA
<213> ORGANISM: Artificial Sequence
<220> FEATURE:
<223> OTHER INFORMATION: Beta chain CDR3

<400> SEQUENCE: 32
gccagcagct tccctaaaca gggatcctac aatgagcagt tc        42

<210> SEQ ID NO 33
<211> LENGTH: 14
<212> TYPE: PRT
<213> ORGANISM: Artificial Sequence
<220> FEATURE:
<223> OTHER INFORMATION: Beta chain CDR3

<400> SEQUENCE: 33

Ala Ser Ser Phe Pro Lys Gln Gly Ser Tyr Asn Glu Gln Phe
1               5                   10

<210> SEQ ID NO 34
<211> LENGTH: 57
<212> TYPE: DNA
<213> ORGANISM: Artificial Sequence
<220> FEATURE:
<223> OTHER INFORMATION: Alpha chain signal peptide

<400> SEQUENCE: 34
atgaactatt ctccaggctt agtatctctg atactcttac tgcttggaag aacccgt        57

<210> SEQ ID NO 35
<211> LENGTH: 19
<212> TYPE: PRT
<213> ORGANISM: Artificial Sequence
<220> FEATURE:
<223> OTHER INFORMATION: Alpha chain signal peptide 3

<400> SEQUENCE: 35

Met Asn Tyr Ser Pro Gly Leu Val Ser Leu Ile Leu Leu Leu Gly
1               5                   10                  15

Arg Thr Arg

<210> SEQ ID NO 36
<211> LENGTH: 336
<212> TYPE: DNA
<213> ORGANISM: Artificial Sequence
<220> FEATURE:
<223> OTHER INFORMATION: Alpha chain variable region 2

<400> SEQUENCE: 36
ggaaattcag tgacccagat ggaagggcca gtgactctct cagaagaggc cttcctgact        60
ataaactgca cgtacacagc cacaggatac ccttcccttt tctggtatgt ccaatatcct       120
ggagaaggtc tacagctcct cctgaaagcc acgaaggctg atgacaaggg aagcaacaaa       180
ggttttgaag ccacataccg taagaaacc acttctttcc acttggagaa aggctcagtt        240
caagtgtcag actcagcggt gtacttctgt gctctgacca acgactacaa gctcagcttt       300
ggagccggaa ccacagtaac tgtaagagca aatatc                                 336

<210> SEQ ID NO 37
<211> LENGTH: 111
<212> TYPE: PRT
<213> ORGANISM: Artificial Sequence
<220> FEATURE:
<223> OTHER INFORMATION: Alpha chain variable region 3

<400> SEQUENCE: 37

```
Gly Asn Ser Val Thr Gln Met Glu Gly Pro Val Thr Leu Ser Glu Glu
1               5                   10                  15

Ala Phe Leu Thr Ile Asn Cys Thr Tyr Thr Ala Thr Gly Tyr Pro Ser
            20                  25                  30

Leu Phe Trp Tyr Val Gln Tyr Pro Gly Glu Gly Leu Gln Leu Leu Leu
        35                  40                  45

Lys Ala Thr Lys Ala Asp Asp Lys Gly Ser Asn Lys Gly Phe Glu Ala
50                  55                  60

Thr Tyr Arg Lys Glu Thr Thr Ser Phe His Leu Glu Lys Gly Ser Val
65                  70                  75                  80

Gln Val Ser Asp Ser Ala Val Tyr Phe Cys Ala Leu Thr Asn Asp Tyr
                85                  90                  95

Lys Leu Ser Phe Gly Ala Gly Thr Thr Val Thr Val Arg Ala Asn
            100                 105                 110
```

<210> SEQ ID NO 38
<211> LENGTH: 420
<212> TYPE: DNA
<213> ORGANISM: Artificial Sequence
<220> FEATURE:
<223> OTHER INFORMATION: Alpha chain constant region 2

<400> SEQUENCE: 38

```
cagaaccctg accctgccgt gtaccagctg agagactcta atccagtga caagtctgtc      60
tgcctattca ccgatttga ttctcaaaca aatgtgtcac aaagtaagga ttctgatgtg     120
tatatcacag acaaaactgt gctagacatg aggtctatgg acttcaagag caacagtgct    180
gtggcctgga gcaacaaatc tgactttgca tgtgcaaacg ccttcaacaa cagcattatt    240
ccagaagaca ccttcttccc cagcccagaa agttcctgtg atgtcaagct ggtcgagaaa    300
agctttgaaa cagatacgaa cctaaacttt caaaacctgt cagtgattgg gttccgaatc    360
ctcctcctga aagtggccgg gtttaatctg ctcatgacgc tgcggctgtg gtccagctga    420
```

<210> SEQ ID NO 39
<211> LENGTH: 140
<212> TYPE: PRT
<213> ORGANISM: Artificial Sequence
<220> FEATURE:
<223> OTHER INFORMATION: Alpha chain constant region 3

<400> SEQUENCE: 39

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
50                  55                  60

Ser Asn Lys Ser Asp Phe Ala Cys Ala Asn Ala Phe Asn Asn Ser Ile
65                  70                  75                  80
```

```
Ile Pro Glu Asp Thr Phe Phe Pro Ser Pro Glu Ser Ser Cys Asp Val
                85                  90                  95
Lys Leu Val Glu Lys Ser Phe Glu Thr Asp Thr Asn Leu Asn Phe Gln
            100                 105                 110
Asn Leu Ser Val Ile Gly Phe Arg Ile Leu Leu Leu Lys Val Ala Gly
        115                 120                 125
Phe Asn Leu Leu Met Thr Leu Arg Leu Trp Ser Ser
    130                 135                 140
```

<210> SEQ ID NO 40
<211> LENGTH: 57
<212> TYPE: DNA
<213> ORGANISM: Artificial Sequence
<220> FEATURE:
<223> OTHER INFORMATION: Beta chain signal peptide 4

<400> SEQUENCE: 40

```
atgggtcctg ggcttctcca ctggatggcc ctttgtctcc ttggaacagg tcatggg        57
```

<210> SEQ ID NO 41
<211> LENGTH: 19
<212> TYPE: PRT
<213> ORGANISM: Artificial Sequence
<220> FEATURE:
<223> OTHER INFORMATION: Beta chain signal peptide 5

<400> SEQUENCE: 41

```
Met Gly Pro Gly Leu Leu His Trp Met Ala Leu Cys Leu Leu Gly Thr
1               5                   10                  15
Gly His Gly
```

<210> SEQ ID NO 42
<211> LENGTH: 342
<212> TYPE: DNA
<213> ORGANISM: Artificial Sequence
<220> FEATURE:
<223> OTHER INFORMATION: Beta chain variable region 4

<400> SEQUENCE: 42

```
gatgccatgg tcatccagaa cccaagatac caggttaccc agtttggaaa gccagtgacc        60
ctgagttgtt ctcagacttt gaaccataac gtcatgtact ggtaccagca gaagtcaagt       120
caggccccaa agctgctgtt ccactactat gacaaagatt ttaacaatga agcagacacc       180
cctgataact ccaatccag gaggccgaac acttctttct gctttcttga catccgctca        240
ccaggcctgg gggacgcagc catgtacctg tgtgccacca gcaggggcgg gaggtacaat       300
gagcagttct cgggccagg gacacggctc accgtgctag ag                          342
```

<210> SEQ ID NO 43
<211> LENGTH: 114
<212> TYPE: PRT
<213> ORGANISM: Artificial Sequence
<220> FEATURE:
<223> OTHER INFORMATION: Beta chain variable region 5

<400> SEQUENCE: 43

```
Asp Ala Met Val Ile Gln Asn Pro Arg Tyr Gln Val Thr Gln Phe Gly
1               5                   10                  15
Lys Pro Val Thr Leu Ser Cys Ser Gln Thr Leu Asn His Asn Val Met
            20                  25                  30
Tyr Trp Tyr Gln Gln Lys Ser Ser Gln Ala Pro Lys Leu Leu Phe His
        35                  40                  45
```

Tyr Tyr Asp Lys Asp Phe Asn Asn Glu Ala Asp Thr Pro Asp Asn Phe
    50                  55                  60

Gln Ser Arg Arg Pro Asn Thr Ser Phe Cys Phe Leu Asp Ile Arg Ser
65                  70                  75                  80

Pro Gly Leu Gly Asp Ala Ala Met Tyr Leu Cys Ala Thr Ser Arg Gly
                85                  90                  95

Gly Arg Tyr Asn Glu Gln Phe Phe Gly Pro Gly Thr Arg Leu Thr Val
            100                 105                 110

Leu Glu

<210> SEQ ID NO 44
<211> LENGTH: 531
<212> TYPE: DNA
<213> ORGANISM: Artificial Sequence
<220> FEATURE:
<223> OTHER INFORMATION: Beta chain constant region 4

<400> SEQUENCE: 44
gacctgaaaa acgtgttccc acccgaggtc gctgtgtttg agccatcaga agcagagatc      60
tcccacaccc aaaaggccac actggtgtgc ctggccacag gcttcttccc tgaccacgtg     120
gagctgagct ggtgggtgaa tgggaaggag gtgcacagtg gggtcagcac ggacccgcag     180
cccctcaagg agcagcccgc cctcaatgac tccagatact gcctgagcag ccgcctgagg     240
gtctcggcca ccttctggca gaaccccgc aaccacttcc gctgtcaagt ccagttctac     300
gggctctcgg agaatgacga gtggaccag gatagggcca aacccgtcac ccagatcgtc     360
agcgccgagg cctggggtag agcagactgt ggctttacct cggtgtccta ccagcaaggg     420
gtcctgtctg ccaccatcct ctatgagatc ctgctaggga aggccaccct gtatgctgtg     480
ctggtcagcg cccttgtgtt gatggccatg gtcaagagaa aggatttctg a            531

<210> SEQ ID NO 45
<211> LENGTH: 175
<212> TYPE: PRT
<213> ORGANISM: Artificial Sequence
<220> FEATURE:
<223> OTHER INFORMATION: Beta chain constant region 5

<400> SEQUENCE: 45

Asp Leu Lys Asn Val Phe Pro Pro Glu Val Ala Val Phe Glu Pro Ser
1               5                  10                  15

Glu Ala Glu Ile Ser His Thr Gln Lys Ala Thr Leu Val Cys Leu Ala
                20                  25                  30

Thr Gly Phe Phe Pro Asp His Val Glu Leu Ser Trp Trp Val Asn Gly
            35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140

```
Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp
                165             170                 175
```

T CELL RECEPTORS WITH MAGE-B2 SPECIFICITY AND USES THEREOF

This application is a national phase application under 35 U.S.C. § 371 of International Application No. PCT/US2019/028239, filed Apr. 19, 2019, which claims the benefit of U.S. Provisional Patent Application No. 62/660,083, filed Apr. 19, 2018, each of which is incorporated herein by reference in their entirety.

The sequence listing that is contained in the file named "UTFCP1372WO_ST25.txt", which is 29 KB (as measured in Microsoft Windows) and was created on Apr. 19, 2019, is filed herewith by electronic submission and is incorporated by reference herein.

FIELD

The present invention relates generally to the fields of medicine and immunology. More particularly, it concerns T cell receptors that specifically recognize melanoma-associated antigen B2 (MAGE-B2).

BACKGROUND

T cell-based therapies have shown significant promise as a method for treating many cancers; unfortunately, this approach has also been hindered by a paucity of immunogenic antigen targets for common cancers and potential toxicity to non-cancerous tissues. These T cell-based therapies can include adoptive cell therapy (ACT) and/or vaccination approaches which induce antitumor T cell responses. Cancer vaccination approaches can comprise the delivery of specific antigens with peptide, protein, DNA, or RNA vaccines, or the induction of anti-cancer responses using dendritic cell (DC) vaccines.

ACT generally involves infusing autologous activated tumor-specific T cells into a patient, e.g., to treat cancer. ACT has resulted in therapeutic clinical responses in melanoma patients. Generally, to develop effective anti-tumor T cell responses, the following three steps are normally required: priming and activating antigen-specific T cells, migrating activated T cells to the tumor site, and recognizing and killing a tumor by antigen-specific T cells.

The choice of target antigen is important for induction of effective antigen-specific T cells. While several tumor-associated antigens have been identified for melanoma and a handful of other solid tumor malignancies, there are few immunogenic targets for pancreatic, ovarian, gastric, lung, cervical, breast, and head and neck cancer. There is a lack of target antigens that are both immunogenic and tumor-specific in their expression patterns, characteristics necessary to be effective at treating cancer and avoid substantial off-target side effects. Thus, there is an unmet medical need for novel T cell-based therapies to additional target antigens for these malignancies.

SUMMARY

Certain embodiments of the present disclosure provide T cell receptors (TCR) which are capable of binding an antigenic peptide derived from the Melanoma-associated Antigen B2 (MAGE-B2). In one embodiment, the TCR comprises a TCR alpha polypeptide having at least 90%, 91%, 92%, 93%, 94%, 95%, 96%, 97%, 98%, 99%, or 100% identity to the sequence of SEQ ID NO: 3 and a TCR beta polypeptide having at least 90%, 91%, 92%, 93%, 94%, 95%, 96%, 97%, 98%, 99%, or 100% identity to the sequence of SEQ ID NO: 5. In another embodiment, there is provided a TCR comprising a TCR alpha polypeptide with at least 90%, 91%, 92%, 93%, 94%, 95%, 96%, 97%, 98%, 99%, or 100% identity to CDR1 (SEQ ID NO: 7), CDR2 (SEQ ID NO: 9), and CDR3 (SEQ ID NO: 11) and a TCR beta polypeptide comprising sequences with at least 90%, 91%, 92%, 93%, 94%, 95%, 96%, 97%, 98%, 99%, or 100% identity to CDR1 (SEQ ID NO: 13), CDR2 (SEQ ID NO: 15), and CDR3 (SEQ ID NO: 17). In particular aspects, the TCR comprises a TCR alpha polypeptide having a sequence of SEQ ID NO: 3 and a TCR beta polypeptide having a sequence of SEQ ID NO: 5.

In another embodiment, the TCR comprises a TCR alpha polypeptide having at least 90%, 91%, 92%, 93%, 94%, 95%, 96%, 97%, 98%, 99%, or 100% identity to the sequence of SEQ ID NO: 19 and a TCR beta polypeptide having at least 90%, 91%, 92%, 93%, 94%, 95%, 96%, 97%, 98%, 99%, or 100% identity to the sequence of SEQ ID NO: 22. In another embodiment, there is provided a TCR comprising a TCR alpha polypeptide with at least 90%, 91%, 92%, 93%, 94%, 95%, 96%, 97%, 98%, 99%, or 100% identity to CDR1 (SEQ ID NO: 23), CDR2 (SEQ ID NO: 25), and CDR3 (SEQ ID NO: 27) and a TCR beta polypeptide comprising sequences with at least 90%, 91%, 92%, 93%, 94%, 95%, 96%, 97%, 98%, 99%, or 100% identity to CDR1 (SEQ ID NO: 29), CDR2 (SEQ ID NO: 31), and CDR3 (SEQ ID NO: 33). In particular aspects, the TCR comprises a TCR alpha polypeptide having a sequence of SEQ ID NO: 19 and a TCR beta polypeptide having a sequence of SEQ ID NO: 22.

In some aspects, the antigenic peptide is HLA-A2 restricted. In some aspects, the antigenic peptide is HLA-A*0201, HLA-A*0202, HLA-A*0203, HLA-A*0204, or HLA-A*0205 restricted. In particular aspects, the antigenic peptide is HLA-A*0201 restricted.

In some aspects, the TCR is a soluble TCR lacking a transmembrane domain. In certain aspects, the TCR further comprises a detectable label and/or a therapeutic agent.

In another embodiment, there is provided a multivalent TCR complex comprising a plurality of TCRs according to the embodiments (e.g., a TCR capable of binding an antigenic peptide derived from MAGE-B2). In some aspects, the multivalent TCR comprises 2, 3, 4 or more TCRs. In certain aspects, the multivalent TCR is present in a lipid bilayer or attached to a particle. In certain aspects, the TCRs are conjugated via a linker molecule.

A further embodiment provides a polypeptide comprising a TCR alpha polypeptide having at least 90%, 91%, 92%, 93%, 94%, 95%, 96%, 97%, 98%, 99%, or 100% identity to the sequence of SEQ ID NO: 3 and/or a TCR beta polypeptide having at least 90%, 91%, 92%, 93%, 94%, 95%, 96%, 97%, 98%, 99%, or 100% identity to the sequence of SEQ ID NO: 5. Another embodiment provides a polypeptide comprising a TCR alpha polypeptide with at least 90%, 91%, 92%, 93%, 94%, 95%, 96%, 97%, 98%, 99%, or 100% identity to CDR1 (SEQ ID NO: 7), CDR2 (SEQ ID NO: 9), and CDR3 (SEQ ID NO: 11) and a TCR beta polypeptide comprising sequences with at least 90%, 91%, 92%, 93%, 94%, 95%, 96%, 97%, 98%, 99%, or 100% identity to CDR1 (SEQ ID NO: 13), CDR2 (SEQ ID NO: 15), and CDR3 (SEQ ID NO: 17). In particular aspects, the polypeptide comprises a TCR alpha polypeptide of SEQ ID NO: 3 and a TCR beta polypeptide of SEQ ID NO: 5. In some aspects, the polypeptide comprises a TCR alpha polypeptide of SEQ ID NO: 3. In certain aspects, the polypeptide comprises a TCR beta polypeptide of SEQ ID NO: 5. Further provided herein are polynucleotides encoding the polypeptide of the embodiments.

A further embodiment provides a polypeptide comprising a TCR alpha polypeptide having at least 90%, 91%, 92%, 93%, 94%, 95%, 96%, 97%, 98%, 99%, or 100% identity to the sequence of SEQ ID NO: 19 and/or a TCR beta polypeptide having at least 90%, 91%, 92%, 93%, 94%, 95%, 96%, 97%, 98%, 99%, or 100% identity to the sequence of SEQ ID NO: 22. Another embodiment provides a polypeptide comprising a TCR alpha polypeptide with at least 90%, 91%, 92%, 93%, 94%, 95%, 96%, 97%, 98%, 99%, or 100% identity to CDR1 (SEQ ID NO: 23), CDR2 (SEQ ID NO: 25), and CDR3 (SEQ ID NO: 27) and a TCR beta polypeptide comprising sequences with at least 90%, 91%, 92%, 93%, 94%, 95%, 96%, 97%, 98%, 99%, or 100% identity to CDR1 (SEQ ID NO: 29), CDR2 (SEQ ID NO: 31), and CDR3 (SEQ ID NO: 33). In particular aspects, the polypeptide comprises a TCR alpha polypeptide of SEQ ID NO: 19 and a TCR beta polypeptide of SEQ ID NO: 22. In some aspects, the polypeptide comprises a TCR alpha polypeptide of SEQ ID NO: 19. In certain aspects, the polypeptide comprises a TCR beta polypeptide of SEQ ID NO: 22. Further provided herein are polynucleotides encoding the polypeptide of the embodiments.

In another embodiment there is provided an expression vector comprising the TCR of the embodiments (e.g., a TCR capable of binding an antigenic peptide derived from MAGE-B2). In some aspects, the expression vector is a viral vector. In certain aspects, the viral vector is a retroviral vector or lentiviral vector. In additional aspects, the TCR comprises a linker domain. In some aspects, the linker domain is between the TCR alpha polypeptide and TCR beta polypeptide. In certain aspects, the linker domain comprises one or more cleavage sites. In some aspects, the one or more cleavage sites are a Furin cleavage site and/or a P2A cleavage site. In some aspects, the one or more cleavage sites are separated by a spacer. In particular aspects, the spacer is SGSG or GSG. In some aspects, the TCR alpha polypeptide and TCR beta polypeptide are linked by an IRES sequence.

Further provided herein is a host cell engineered to express a TCR of the embodiments (e.g., a TCR capable of binding an antigenic peptide derived from MAGE-B2).

In some aspects, the cell is an immune cell. In certain aspects, the cell is isolated from the umbilical cord or blood. In some aspects, the immune cell is a T cell or peripheral blood lymphocyte. In particular aspects, the T cell is a CD8$^+$ T cell, CD4$^+$ T cell, or γδ T cell. In some aspects, the relevant signaling molecule can be attached to the TCR, and upon TCR engagement, transmit an activation signal in non-T cell immune effector cells. In certain aspects, the cell is an NK cell, invariant NK cell, NKT cell, mesenchymal stem cell (MSC), or induced pluripotent stem (iPS) cell. In some aspects, the cell is allogeneic or autologous. Further provided herein is a pharmaceutical composition comprising a population of MAGE-B2 TCR-specific cells of the embodiments.

Further provided herein is a method for engineering a MAGE-B2-specific immune cell comprising contacting said immune cell with the expression vector of the embodiments. In some aspects, the immune cell is a T cell, peripheral blood lymphocyte, NK cell, invariant NK cell, or NKT cell. In some aspects, contacting is further defined as transfecting or transducing. In certain aspects, the peripheral blood lymphocyte is stimulated with OKT3 and IL-2. In additional aspects, the method further comprises sorting the immune cells to isolate TCR engineered T cells, performing T cell cloning by serial dilution, and expansion of a T cell clone by rapid expansion protocol.

In another embodiment, there is provided the use of a therapeutically effective amount of MAGE-B2-specific TCR expressing cells according to the embodiments for the treatment of cancer. Also provided herein is a composition comprising an effective amount of MAGE-B2-specific cells according to the embodiments for the treatment of cancer in a subject. In particular aspects, the MAGE-B2-specific TCR expressing cells are T cells.

In another embodiment, there is provided a method of treating cancer in a subject comprising administering a therapeutically effective amount of MAGE-B2-specific cells of the embodiments (e.g., expressing a TCR capable of binding an antigenic peptide derived from MAGE-B2) to the subject. In some aspects, the MAGE-B2-specific cells are T cells.

In certain aspects, the subject is identified to have an HLA-A2 allele, such as a HLA-A*0201, HLA-A*0202, HLA-A*0203, HLA-A*0204, or HLA-A*0205 allele. In certain aspects, the subject is identified to have an HLA-A*0201 allele. In additional aspects, the method further comprises a step of performing lymphodepletion on the subject prior to administration of the therapeutically effective amount of MAGE-B2-specific T cells. In some aspects, the therapeutically effective amount of MAGE-B2-specific T cells is derived from a sample of autologous tumor infiltrating lymphocytes (TILs) having antitumor activity. In some aspects, the MAGE-B2-specific cells are administered to the subject intravenously, intraperitoneally, or intratumorally. In particular aspects, the subject is a human. In some aspects, the method further comprises the step of administering at least one additional therapeutic agent to the subject. In certain aspects, the at least one additional therapeutic agent is selected from the group consisting of chemotherapy, radiotherapy, and immunotherapy. In some aspects, the at least one additional therapeutic agent is an immunotherapy. In some aspects, the immunotherapy is an immune checkpoint inhibitor. In certain aspects, the immune checkpoint inhibitor inhibits an immune checkpoint protein or ligand thereof selected from the group consisting of CTLA-4, PD-1, PD-L1, PD-L2, LAG-3, BTLA, B7H3, B7H4, TIM3, KIR, or adenosine A2a receptor (A2aR). In some aspects, the immune checkpoint inhibitor inhibits PD-1 or CTLA-4.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) Peptide titration assay of T2 cells pulsed with MAGE-B2 peptide. (FIG. 3B) Cytotoxicity of CTL clone to lung cancer cell line H2023 (HLA-A*0201) and normal lung cell line HSAEC2-KT (HLA-A*0201) by $^{51}$Cr release assay. (FIG. 3C) Cytotoxicity of CTL clone to lung cancer cell lines H522, H1355, H1755 and DFC-1032. (FIG. 3D) Cytotoxicity of MAGE-B2 CTL clone to parental lung cancer cell lines PC-9 and H1573 as well as HLA-A2 forced expression in both cell lines.

(FIG. 5A) Peptide titration assay. T2 cells pulsed with different concentration of MAGE-B2 peptide. (FIG. 5B) MAGE-B2 TCR-T cytotoxicity against the lung cancer cell line H2023 (HLA-A*0201) and normal lung cell line HSAEC2-KT (HLA-A*0201) detected by standard $^{51}$Cr release assay.

(FIG. 8A) 3 MAGE-B2 CTL cell lines lysis T2 cells pulsed with various concentrations of MB2-231 peptide with an effector to target (E:T) ratio of 20:1. (FIG. 8B) 3 MAGE-B2 CTL cell lines lysis MAGE-B2 expressing tumor cell line H2023 (HLA-A2$^+$) at various E:T ratios. The normal lung cell line HSAEC2-KT (MAGE-B2$^-$, HLA-A2$^+$) is a negative control. (FIG. 8C) 3 MAGE-B2 CTL cell lines lysis MAGE-B2 expressing and HLA-A2 forced expressing tumor cell line H1299-A2 at various E:T ratios. The parental cell line H1299 (HLA-A2-) is a negative control. (FIGS. 8D-8E) 3 MAGE-B2 CTL cell lines lysis more tumor cell line H1395 (MAGE-B2$^+$, HLA-A2$^+$), H522 (MAGE-B2$^+$, HLA-A2$^+$), H1355 (MAGE-B2$^+$, HLA-A2$^+$), H1755 (MAGE-B2$^+$, HLA-A2$^+$) and DFC-1032 (MAGE-B2$^+$, HLA-A2$^+$).

(FIG. 9A) Tetramer detection of TCR-T before, after infection with retrovirus containing TCR-T gene from high functional CTL cell line MB2-231 C5, and after tetramer guided sorting and expansion. (FIG. 9B) MB2-231 C5 TCR-T lysis T2 cells pulsed with various concentrations of MB2-231 peptide with an effector to target (E:T) ratio of 20:1. (FIG. 9C) MB2-231 C5 TCR-T lysis MAGE-B2 expressing tumor cell line H2023 (HLA-A2$^+$), normal lung cell line HSAEC2-KT (MAGE-B2$^-$, HLA-A2$^+$) is a negative control. (FIG. 9D) MB2-231 C5 TCR-T lysis MAGE-B2 expressing and HLA-A2 forced expressing tumor cell line H1299-A2 at various E:T ratios. The parental cell line H1299 (HLA-A2$^-$) is a negative control. (FIG. 9E) MB2-231 C5 TCR-T lysis more tumor cell line H1395 (MAGE-B2$^+$, HLA-A2$^+$), H522 (MAGE-B2$^+$, HLA-A2$^+$), H1355 (MAGE-B2$^+$, HLA-A2$^+$), H1755 (MAGE-B2$^+$, HLA-A2$^+$) and DFC-1032 (MAGE-B2$^+$, HLA-A2$^+$) at various E:T ratios.

DETAILED DESCRIPTION

Figure 1:
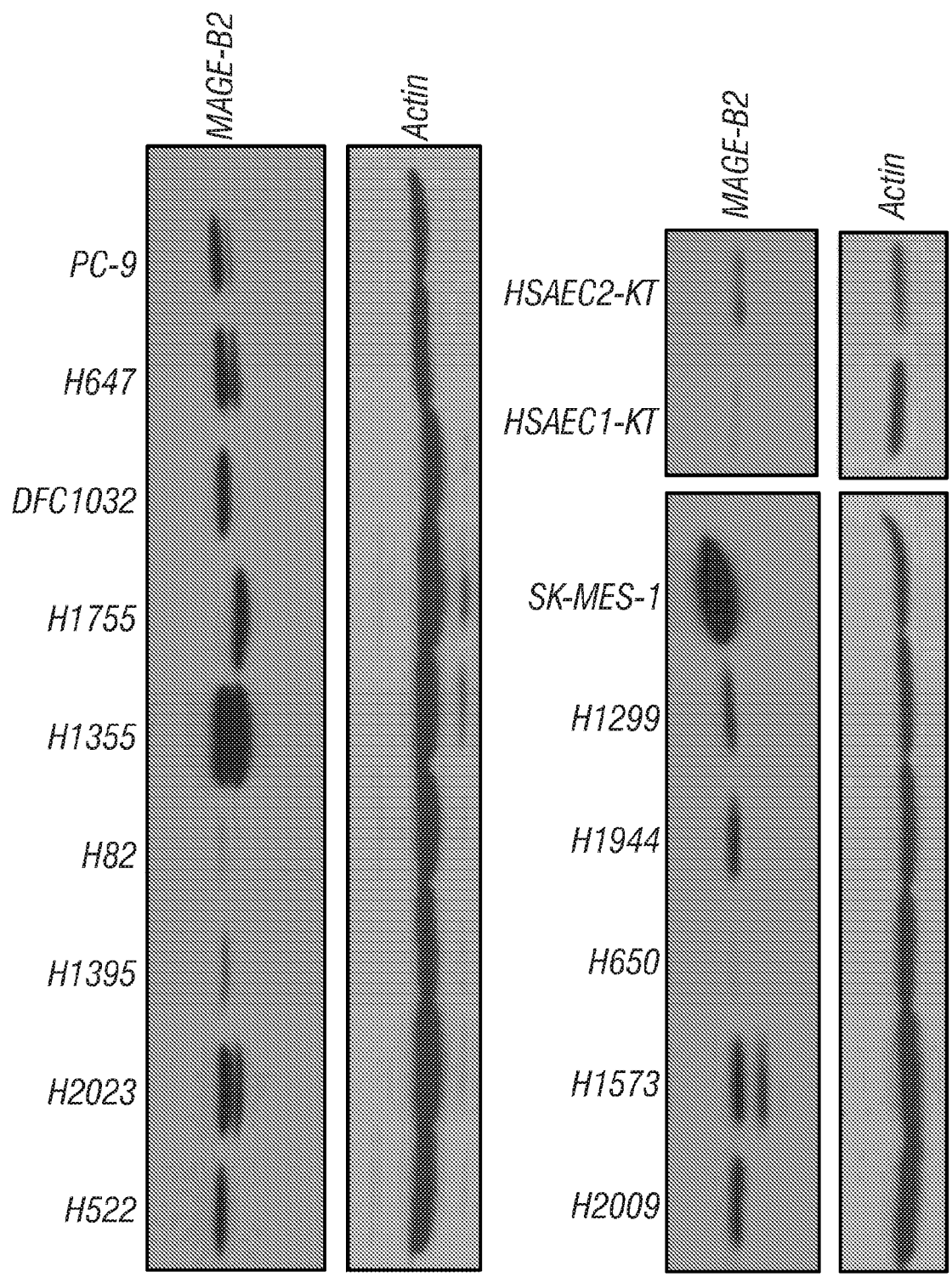
FIG. 1: Western-Blot detection of MAGE-B2 expression in lung cancer cell lines and immortalized normal human small air epithelial cells (HSAEC1-KT and HSAEC2-KT).

Melanoma-associated antigen B2 (MAGE-B2), also known as cancer/testis antigen 3.2 (UniProt No. O15479) (CT3.2), is encoded by a gene located on the X chromosome. MAGE-B2 is expressed in testes, as measured by protein and RNA levels, but not in other normal tissues. MAGE-B2 is overexpressed in several cancers including lung cancer, liver cancer, head and neck cancer, stomach cancer, glioblastoma, and colorectal cancer. One HLA-A2 (e.g., HLA-A*0201, HLA-A*0202, HLA-A*0203, HLA-A*0204, or HLA-A*0205) restricted peptide (GVYDGEEHSV, SEQ ID NO: 1) has been eluted and identified from ovarian cancer cells (Barnea et al., 2002). The epitope was also identified from peptidome analysis of glioblastoma multiforme cells T98G and U-87 (Shraibman et al., 2016).

Using the MAGE-B2 peptide epitope, antigen-specific CTLs were generated in the present studies from patient peripheral blood mononuclear cells (PBMCs) that recognized the endogenously-presented antigen on HLA-matched allogeneic tumor cell lines. These antigen-specific CTLs stimulated by antigen-presenting cells presenting this HLA-A2-restricted MAGE-B2 peptide were shown to be selectively cytotoxic against lung cancer cells.

Thus, in certain aspects, the present disclosure provides a TCR which recognizes and specifically binds the MAGE-B2 HLA-A2 restricted epitope GVYDGEEHSV (SEQ ID NO: 1). The present disclosure also provides a nucleotide sequence encoding this TCR, an expression vector comprising this nucleotide sequence which can be used to modify naïve T cells and generate MAGE-B2-specific T cells. The present disclosure further provides the use of MAGE-B2-specific T cells for therapy, such as adoptive cell therapy for cancer patients, such as HLA-A2-positive cancer patients, whose malignant cells express MAGE-B2 antigen. The antigen-specific T cells, such as CTLs, provided herein may be used to target solid cancers.

I. Definitions

The singular terms "a", "an", and "the" as used herein and in the appended claims include plural referents unless the context clearly dictates otherwise. Thus, for example, reference to "a cell" includes a plurality of such cells and reference to "the peptide" includes reference to one or more peptides and equivalents thereof (e.g., polypeptides) known to those skilled in the art.

The term "or" as used herein and in the appended claims means "and/or" unless explicitly indicated to refer to alternatives only or the alternatives are mutually exclusive.

The term "another" as used herein and in the appended claims may mean at least a second or more.

The term "about" as used herein indicates that a particular value or measurement includes the inherent variation associated with the device used to obtain the measurement, to calculate the value, or the natural variation that exists among the study subjects.

The term "essentially free" as used herein with respect to a component of a solution (e.g., a preparation of one or more proteins, polymers, or small molecules) means that the preparation was not formulated to include that component, or that such component is present only in trace amounts (e.g., as a contaminant). In certain embodiments, a preparation of a molecule of interest is essentially free of a particular component if the preparation comprises less than 0.05% (w/w) of that component. In certain embodiments, a preparation of a molecule of interest is essentially free of a particular component if the preparation comprises less than 0.01% (w/w) of that component. In certain embodiments, a preparation of a molecule of interest is essentially free of a particular component if no amount of the specified component can be detected in the preparation using standard analytical methods (e.g., UV spectrophotometry, mass spectrometry, nuclear magnetic resonance spectroscopy, etc.).

The term "enriched" as used herein with respect to a component of a solution or suspension (e.g., a preparation of one or more cell types, proteins, polymers, or small molecules) means that the preparation was formulated to include that component at a higher than normal concentration, or in greater than normal numbers (e.g., a suspension of lymphocytes may be enriched for effector T lymphocytes).

As used herein, the terms "treat", "treatment", "treating", and the like refer to the process of ameliorating, lessening, or otherwise mitigating the symptoms of a disease or condition in a subject by, for example, administering a therapeutic agent to the subject, or by performing a surgical, clinical, or other medical procedure on the subject.

As used herein, the terms "subject" or "patient" are used interchangeably herein to refer to an individual, e.g., a human or a non-human organism, such as a primate, a mammal, or a vertebrate.

As used herein, the terms "therapeutically effective" or "therapeutically beneficial" and the like refer to a therapeutic agent, or a surgical, clinical, or other medical procedure that ameliorates, mitigates or otherwise relieves one or more symptoms of a disease, disorder, or condition, thereby enhancing the well-being of a subject having a disease, disorder, or condition by, for example, reducing the frequency or severity of the signs or symptoms of a disease, disorder, or condition. Thus, a therapeutically effective or therapeutically beneficial cancer treatment may, for example, reduce the size of a tumor, reduce the growth rate of a tumor, reduce the likelihood of tumor dissemination or metastasis.

As used herein, the terms "pharmaceutically acceptable" or "pharmacologically acceptable" refer to pharmaceutical formulations of therapeutic agents that do not produce an adverse, allergic, or other undesired reaction when administered to a mammalian or vertebrate subject. Such preparations should be formulated in compliance with good manufacturing practice (GMP) standards for sterility, pyrogenicity, purity, and any other relevant standards as required by FDA Office of Biological Standards.

As used herein, the term "pharmaceutically acceptable carrier" refers to any and all chemical compounds or solvents used to formulate a therapeutic agent for delivery to a mammalian or vertebrate subject such as, for example, aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, and any combinations thereof, as would be known to one of ordinary skill in the art.

As used herein, the terms "unit dose", "dose", or "dosage" refer to formulations of a therapeutic agent suitable for administration to a mammalian or vertebrate subject containing a predetermined quantity of the agent expected to be therapeutically effective in the subject when administered by an appropriate route and according to a desired treatment regimen. The actual dosage of a particular therapeutic agent to be administered to a subject may be determined empirically by a health care provider in light of a variety of physical and physiological parameters, including, for example, the subject's body weight, age, health, and gender, the type of disease being treated, the extent of disease progression, previous or concurrent therapeutic interventions, the route of administration, and the potency, stability, and toxicity of the particular therapeutic substance.

II. Mage-B2 TCR Methods and Compositions

In certain embodiments, the present disclosure provides a MAGE-B2 peptide epitope comprising the sequence GVYDGEEHSV (SEQ ID NO: 1). The MAGE-B2 peptide epitope may be contacted with or used to stimulate a population of T cells to induce proliferation of the T cells that recognize or bind the MAGE-B2 peptide epitope. The MAGE-B2 peptide epitope may be administered to a subject, such as a human patient, to enhance the immune response of the subject against a cancer. A MAGE-B2 peptide epitope may be included in an active immunotherapy (e.g., a cancer vaccine) or a passive immunotherapy (e.g., an adoptive cell therapy). Active immunotherapies include immunizing a subject with a purified tumor antigen or a MAGE-B2 peptide epitope (native or modified). Alternately, antigen presenting cells pulsed with a MAGE-B2 peptide epitope (or transfected with genes encoding the tumor antigen) may be administered to a subject. The MAGE-B2 peptide epitope may be modified or contain one or more mutations such as, e.g., a substitution mutation. Adoptive cell therapies may involve administering cells to a subject, wherein the cells (e.g., cytotoxic T cells) have been sensitized in vitro to the MAGE-B2 peptide epitope.

In particular, T cells can be activated and expanded ex vivo for adoptive cell therapies within a short period of time, such as 6 to 8 weeks. The T cells may be isolated and expanded from T cells (e.g., CD4$^+$ T cells, CD8$^+$ T cells, γδ T cells and regulatory T cells (Tregs)) isolated from peripheral blood, such as with the tetramer guided sorting and rapid expansion protocol (REP). Next, the peptide or corresponding polynucleotides (e.g., full length MAGE-B2 or the MAGE-B2 peptide epitope) can be loaded to HLA-A2 positive dendritic cells, lymphoblastoid cell lines (LCLs), PBMCs, or artificial antigen presenting cells (aAPCs), and then co-cultured with the T cells by several rounds of stimulation to generate antigen-specific CTL cell lines or clones. Furthermore, with manipulation of immune modulating parameters, the effector function and long-term persistence in vivo of these expanded antigen specific T cells can be enhanced. These CTLs can be used for adoptive cell therapy for MAGE-B2 and HLA-A2 positive cancer patients. Further, other MAGE-B2-specific cells that can be generated from the present disclosure include NK cells, invariant NK cells, NKT cells, mesenchymal stem cells (MSCs), and induced pluripotent stem (iPS) cells. These cells may be isolated from blood or the umbilical cord. The antigen-specific cells of the present disclosure may be autologous or allogeneic.

In another method, antigen-specific cells can be generated by using the MAGE-B2 TCRs provided herein (e.g., SEQ ID NOs: 2-5 or 18-22). In this method, the TCR sequence is inserted into a vector (e.g., retroviral or lentiviral vector) which is introduced into host cells, such as T cells (e.g., CD4⁺ T cells, CD8⁺ T cells, γδ T cells, and Tregs), NK cells, invariant NK cells, NKT cells, MSCs, or iPS cells to generate antigen-specific cells which can be used for adoptive cell therapy for cancer patients.

MAGE-B2 peptide epitope and TCR sequences are provided below.

```
Peptide epitope:
                                        (SEQ ID NO: 1)
GVYDGEEHSV Alpha Chain (TRAV9-2*01F):
                                        (SEQ ID NO: 2)
ATGAACTATTCTCCAGGCTTAGTATCTCTGATACTCTTACTGCTTGGAAG

AACCCGTGGAAATTCAGTGACCCAGATGGAAGGGCCAGTGACTCTCTCAG

AAGAGGCCTTCCTGACTATAAACTGCACGTACACAGCCACAGGATACCCT

TCCCTTTTCTGGTATGTCCAATATCCTGGAGAAGGTCTACAGCTCCTCCT

GAAAGCCACGAAGGCTGATGACAAGGGAAGCAACAAAGGTTTTGAAGCCA

CATACCGTAAAGAAACCACTTCTTTCCACTTGGAGAAAGGCTCAGTTCAA

GTGTCAGACTCAGCGGTGTACTTCTGTGCTCTGACCAACGACTACAAGCT

CAGCTTTGGAGCCGGAACCACAGTAACTGTAAGAGCAAATATCCAGAACC

CTGACCCTGCCGTGTACCAGCTGAGAGACTCTAAATCCAGTGACAAGTCT

GTCTGCCTATTCACCGATTTTGATTCTCAAACAAATGTGTCACAAAGTAA

GGATTCTGATGTGTATATCACAGACAAAACTGTGCTAGACATGAGGTCTA

TGGACTTCAAGAGCAACAGTGCTGTGGCCTGGAGCAACAAATCTGACTTT

GCATGTGCAAACGCCTTCAACAACAGCATTATTCCAGAAGACACCTTCTT

CCCCAGCCCAGAAAGTTCCTGTGATGTCAAGCTGGTCGAGAAAAGCTTTG

AAACAGATACGAACCTAAACTTTCAAAACCTGTCAGTGATTGGGTTCCGA

ATCCTCCTCCTGAAAGTGGCCGGGTTTAATCTGCTCATGACGCTGCGGCT

GTGGTCCAGCTGA

Alpha Chain
                                        (SEQ ID NO: 3)
MNYSPGLVSL ILLLLGRTRG NSVTQMEGPV TLSEEAFLTI

NCTYTATGYP SLFWYVQYPG EGLQLLLKAT KADDKGSNKG

FEATYRKETT SFHLEKGSVQ VSDSAVYFCA LTNDYKLSFG

AGTTVTVRAN IQNPDPAVYQ LRDSKSSDKS VCLFTDFDSQ

TNVSQSKDSD VYITDKTVLD MRSMDFKSNS AVAWSNKSDF

ACANAFNNSI IPEDTFFPSP ESSCDVKLVE KSFETDTNLN

FQNLSVIGFR ILLLKVAGFN LLMTLRLWSS

Beta Chain (TRBV15*02F)
                                        (SEQ ID NO: 4)
ATGGGTCCTGGGCTTCTCCACTGGATGGCCCTTTGTCTCCTTGGAACAGG

TCATGGGGATGCCATGGTCATCCAGAACCCAAGATACCAGGTTACCCAGT

TTGGAAAGCCAGTGACCCTGAGTTGTTCTCAGACTTTGAACCATAACGTC

ATGTACTGGTACCAGCAGAAGTCAAGTCAGGCCCCAAAGCTGCTGTTCCA

CTACTATGACAAAGATTTTAACAATGAAGCAGACACCCCTGATAACTTCC

AATCCAGGAGGCCGAACACTTCTTTCTGCTTTCTTGACATCCGCTCACCA

GGCCTGGGGGACGCAGCCATGTACCTGTGTGCCACCAGCAGGGGCGGGAG

GTACAATGAGCAGTTCTTCGGGCCAGGGACACGGCTCACCGTGCTAGAGG

ACCTGAAAAACGTGTTCCCACCCGAGGTCGCTGTGTTTGAGCCATCAGAA

GCAGAGATCTCCCACACCCAAAAGGCCACACTGGTGTGCCTGGCCACAGG

CTTCTTCCCTGACCACGTGGAGCTGAGCTGGTGGGTGAATGGGAAGGAGG

TGCACAGTGGGGTCAGCACGGACCCGCAGCCCCTCAAGGAGCAGCCCGCC

CTCAATGACTCCAGATACTGCCTGAGCAGCCGCCTGAGGGTCTCGGCCAC

CTTCTGGCAGAACCCCCGCAACCACTTCCGCTGTCAAGTCCAGTTCTACG

GGCTCTCGGAGAATGACGAGTGGACCCAGGATAGGGCCAAACCCGTCACC

CAGATCGTCAGCGCCGAGGCCTGGGGTAGAGCAGACTGTGGCTTTACCTC

GGTGTCCTACCAGCAAGGGGTCCTGTCTGCCACCATCCTCTATGAGATCC

TGCTAGGGAAGGCACCCTGTATGCTGTGCTGGTCAGCGCCCTTGTGTTG

ATGGCCATGGTCAAGAGAAAGGATTTCTGA

Beta Chain
                                        (SEQ ID NO: 5)
MGPGLLHWMA LCLLGTGHGD AMVIQNPRYQ VTQFGKPVTL

SCSQTLNHNV MYWYQQKSSQ APKLLFHYYD KDFNNEADTP

DNFQSRRPNT SFCFLDIRSP GLGDAAMYLC ATSRGGRYNE

QFFGPGTRLT VLEDLKNVFP PEVAVFEPSE AEISHTQKAT

LVCLATGFFP DHVELSWWVN GKEVHSGVST DPQPLKEQPA

LNDSRYCLSS RLRVSATFWQ NPRNHFRCQV QFYGLSENDE

WTQDRAKPVT QIVSAEAWGR ADCGFTSVSY QQGVLSATIL

YEILLGKATL YAVLVSALVL MAMVKRKDF

Alpha chain CDR1
                                        (SEQ ID NO: 6)
GCCACAGGATACCCTTCC (SEQ ID NO: 7)
ATGYPS Alpha chain CDR2
                                        (SEQ ID NO: 8)
GCCACGAAGGCTGATGACAAG (SEQ ID NO: 9)
ATKADDK
```

Alpha chain CDR3

(SEQ ID NO: 10)
GCTCTGACCAACGACTACAAGCTCAGC (SEQ ID NO: 11)
ALTNDYKLS

Beta chain CDR1

(SEQ ID NO: 12)
TTGAACCATAACGTC (SEQ ID NO: 13)
LNHNV

Beta chain CDR2

(SEQ ID NO: 14)
TACTATGACAAAGATTTT (SEQ ID NO: 15)
YYDKDF

Beta chain CDR3

(SEQ ID NO: 16)
GCCACCAGCAGGGGCGGGAGGTACAATGAGCAGTTC (SEQ ID NO: 17)
ATSRGGRYNEQF

MAGE-B2-231 C5 TCR sequences are provided below. The signal peptide is underlined and the variable region is italicized Alpha Chain (TRAV10*01):

(SEQ ID NO: 18)
ATGAAAAAGCATCTGACGACCTTCTTGGTGATTTTGTGGCTTTATTTTTA
TAGGGGGAATGGCAAAAACCAAGTGGAGCAGAGTCCTCAGTCCCTGATCA
TCCTGGAGGGAAAGAACTGCACTCTTCAATGCAATTATACA
*GTGAGCCCCTTCAGCAAC*TTAAGGTGGTATAAGCAAGATACTGGGAGAGG
TCCTGTTTCCCTGACAATC*ATGACTTTCAGTGAGAACACA*AAGTCGAACG
GAAGATATACAGCAACTCTGGATGCAGACACAAAGCAAAGCTCTCTGCAC
ATCACAGCCTCCCAGCTCAGCGATTCAGCCTCCTACATCTGT
*GTGGTGATTTCAGGCTTTCAGAAACTTGTA*TTTGGAACTGGCACCCGACT
TCTGGTCAGTCCAAATATCCAGAACCCTGACCCTGCCGTGTACCAGCTGA
GAGACTCTAAATCCAGTGACAAGTCTGTCTGCCTATTCACCGATTTTGAT
TCTCAAACAAATGTGTCACAAAGTAAGGATTCTGATGTGTATATCACAGA
CAAAACTGTGCTAGACATGAGGTCTATGGACTTCAAGAGCAACAGTGCTG
TGGCCTGGAGCAACAAATCTGACTTTGCATGTGCAAACGCCTTCAACAAC
AGCATTATTCCAGAAGACACCTTCTTCCCCAGCCCAGAAAGTTCCTGTGA
TGTCAAGCTGGTCGAGAAAAGCTTTGAAACAGATACGAACCTAAACTTTC
AAAACCTGTCAGTGATTGGTTCCGAATCCTCCTCCTGAAAGTGGCCGGG
TTTAATCTGCTCATGACGCTGCGGCTGTGGTCCAGCTAA

Alpha Chain (SEQ ID NO: 19)
MKKHLTTFLVILWLYFYRGNGKNQVEQSPQSLIILEGKNCTLQCNYT
*VSPFSN*LRWYKQDTGRGPVSLT*IMTFSENT*KSNGRYTATLDADTKQSSLH
ITASQLSDSASYIC*VVISGFQKLV*FGTGTRLLVSPNIQNPDAVYQLRDS
KSSDKSVCLFTDFDSQTNVSQSKDSDVYITDKTVLDMRSMDFKSNSAVAW
SNKSDFACANAFNNSIIPEDTFFPSPESSCDVKLVEKSFETDTNLNFQNL
SVIGFRILLLKVAGFNLLMTLRLWSS Beta Chain (TRBV11-3*04)

(SEQ ID NO: 20)
ATGGGTACCAGGCTCCTCTGCTGGGTGGCCTTCTGTCTCCTGGTGGAAGA
ACTCATAGAAGCTGGAGTGGTTCAGTCTCCCAGATATAAGATTATAGAGA
AAAAACAGCCTGTGGCTTTTTGGTGCAATCCTATTTCTGGCCACAATACC
CTTTACTGGTACCGGCAGAACTTGGGACAGGGCCCGGAGCTTCTGATTCG
ATATGAGAATGAGGAAGCAGTAGACGATTCACAGTTGCCTAAGGATCGAT
TTTCTGCAGAGAGGCTCAAAGGAGTAGACTCCACTCTCAAGATCCAGCCT
GCAGAGCTTGGGGACTCGGCCGTGTATCTCTGT
*GCCAGCAGCTTCCCTAAACAGGGATCCTACAATGAGCAGTTC*TTCGGGCC
AGGGACACGGCTCACCGTGCTAGAGGACCTGAAAAACGTGTTCCCACCCG
AGGTCGCTGTGTTTGAGCCATCAGAAGCAGAGATCTCCCACACCCAAAAG
GCCACACTGGTGTGCCTGGCCACAGGCTTCTTCCCTGACCACGTGGAGCT
GAGCTGGTGGGTGAATGGGAAGGAGGTGCACAGTGGGGTCAGCACGGACC
CGCAGCCCCTCAAGGAGCAGCCCGCCCTCAATGACTCCAGATACTGCCTG
AGCAGCCGCCTGAGGGTCTCGGCCACCTTCTGGCAGAACCCCCGCAACCA
CTTCCGCTGTCAAGTCCAGTTCTACGGGCTCTCGGAGAATGACGAGTGGA
CCCAGGATAGGGCCAAACCCGTCACCCAGATCGTCAGCGCCGAGGCCTGG
GGTAGAGCAGACTGTGGCTTTACCTCGGTGTCCTACCAGCAAGGGGTCCT
GTCTGCCACCATCCTCTATGAGATCCTGCTAGGGAAGGCCACCCTGTATG
CTGTGCTGGTCAGCGCCCTTGTGTTGATGGCCATGGTCAAGAGAAAGGAT
TTCTAA

Beta Chain (SEQ ID NO: 21)
MGTRLLCWVAFCLLVEELIEAGVVQSPRYKIIEKKQPVAFWCNPI*SGHNT*
LYWYRQNLGQGPELLIR*YENEEA*VDDSQLPKDRFSAERLKGVDSTLKIQP
AELGDSAVYLC*ASSFPKQGSYNEQF*FGPGTRLTVLEDLKNVFPPEVAVFE
PSEAEISHTQKATLVCLATGFFPDHVELSWWVNGKEVHSGVSTDPQPLKE
QPALNDSRYCLSSRLRVSATFWQNPRNHFRCQVQFYGLSENDEWTQDRAK
PVTQIVSAEAWGRADCGFTSVSYQQGVLSATILYEILLGKATLYAVLVSA
LVLMAMVKRKDF Alpha chain CDR1

(SEQ ID NO: 22)
GTGAGCCCCTTCAGCAAC (SEQ ID NO: 23)
VSPFSN

Alpha chain CDR2

(SEQ ID NO: 24)
ATGACTTTCAGTGAGAACACA (SEQ ID NO: 25)
MTFSENT

-continued

Alpha chain CDR3
(SEQ ID NO: 26)
GTGGTGATTTCAGGCTTTCAGAAACTTGTA (SEQ ID NO: 27)
VVISGFQKLV Beta chain CDR1
(SEQ ID NO: 28)
TCTGGCCACAATACC (SEQ ID NO: 29)
SGHNT Beta chain CDR2
(SEQ ID NO: 30)
TATGAGAATGAGGAAGCA (SEQ ID NO: 31)
YENEEA Beta chain CDR3
(SEQ ID NO: 32)
GCCAGCAGCTTCCCTAAACAGGGATCCTACAATGAGCAGTTC (SEQ ID NO: 33)
ASSFPKQGSYNEQF A. MAGE-B2 Peptides In some aspects, the present disclosure comprises a MAGE-B2 peptide epitope. The MAGE-B2 peptide epitopes may have the amino acid sequence of the HLA-A2 restricted MAGE-B2 peptide GVYDGEEHSV; SEQ ID NO: 1. The MAGE-B2 peptide epitope may have an amino acid sequence with at least 80, 85, 90, 95, 96, 97, 98, 99, or 100 percent sequence identity with the peptide sequence of SEQ ID NO: 1.

The MAGE-B2 peptide epitope may comprise or consist of 7-35 amino acids, preferably 8-35 amino acid residues, and even more preferably 8-25 amino acids, or 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acids in length, or any range derivable therein. For example, a MAGE-B2 peptide epitope of the present disclosure may, in some embodiments, comprise or consist of the MAGE-B2 peptide epitope of SEQ ID NO: 1. An antigenic peptide may comprise an immunoreactive MAGE-B2 peptide epitope, and may comprise additional sequences. The additional sequences may be derived from a native antigen and may be heterologous, and such sequences may, but need not, be immunogenic. In some embodiments, a MAGE-B2 peptide epitope can selectively bind with HLA-A2, particularly HLA-A*0201, HLA-A*0202, HLA-A*0203, HLA-A*0204, or HLA-A*0205.

As would be appreciated by one of skill in the art, MHC molecules can bind peptides of varying sizes, but typically not full-length proteins. While MHC class I molecules have been traditionally described to bind to peptides of 8-11 amino acids long, it has been shown that peptides 15 amino acids in length can bind to MHC class I molecules by bulging in the middle of the binding site or extending out of the MHC class I binding groove. As would be immediately appreciated by one of skill, a naturally occurring full-length tumor antigen, such as MAGE-B2, would not be useful to selectively bind a class II MHC such that it would be endocytosed and generate proliferation of T cells. Generally, the naturally occurring full-length tumor antigen proteins do not display these properties and would thus not be useful for these immunotherapy purposes.

In certain embodiments, a MAGE-B2 peptide epitope is immunogenic or antigenic. As shown in the below examples, a MAGE-B2 peptide epitope of the present disclosure can promote the proliferation of T cells.

A MAGE-B2 peptide epitope may be a recombinant peptide, synthetic peptide, purified peptide, immobilized peptide, detectably labeled peptide, encapsulated peptide, or a vector-expressed peptide (e.g., a peptide encoded by a nucleic acid in a vector comprising a heterologous promoter operably linked to the nucleic acid). In some embodiments, a synthetic MAGE-B2 peptide epitope may be administered to a subject, such as a human patient, to induce an immune response in the subject. Synthetic peptides may display certain advantages, such as a decreased risk of bacterial contamination, as compared to recombinantly expressed peptides. A MAGE-B2 peptide may also be comprised in a pharmaceutical composition such as, e.g., a vaccine composition, which is formulated for administration to a mammalian or human subject.

1. Cell Penetrating Peptides

In some embodiments, an immunotherapy may utilize a MAGE-B2 peptide epitope of the present disclosure that is associated with a cell penetrator, such as a liposome or a cell penetrating peptide (CPP). Antigen presenting cells (such as dendritic cells) pulsed with peptides may be used to enhance antitumor immunity. In some embodiments, an immunotherapy may utilize a nucleic acid encoding a MAGE-B2 peptide epitope of the present disclosure, wherein the nucleic acid is delivered, e.g., in a viral vector or non-viral vector.

Cell penetrating peptides that may be covalently bound to a tumor antigen-specific peptide (e.g., a MAGE-B2 peptide) include, e.g., HIV Tat, herpes virus VP22, the Drosophila Antennapedia homeobox gene product, signal sequences, fusion sequences, or protegrin I. Covalently binding a peptide to a CPP can prolong the presentation of a peptide by dendritic cells, thus enhancing antitumor immunity. In some embodiments, a MAGE-B2 peptide of the present disclosure (e.g., comprised within a peptide or polyepitope string) may be covalently bound (e.g., via a peptide bond) to a CPP to generate a fusion protein. In other embodiments, a MAGE-B2 peptide epitope or nucleic acid encoding the peptide epitope may be encapsulated within or associated with a liposome, such as a multilamellar, vesicular, or multivesicular liposome, an exocytic vesicle or exosome.

In some embodiments, cellular uptake is facilitated by the attachment of a lipid, such as stearate or myristate, to the polypeptide. Lipidation has been shown to enhance the passage of peptides into cells. The attachment of a lipid moiety is another way that the present disclosure increases polypeptide uptake by the cell. Cellular uptake is further discussed below.

A MAGE-B2 peptide epitope of the present disclosure may be included in a liposomal vaccine composition. For example, the liposomal composition may be or comprise a proteoliposomal composition.

In some embodiments, a MAGE-B2 peptide epitope may be associated with a nanoparticle to form nanoparticle-polypeptide complex. In some embodiments, the nanoparticle is a liposome or other lipid-based nanoparticle such as a lipid-based vesicle (e.g., a DOTAP:cholesterol vesicle). In other embodiments, the nanoparticle is an iron-oxide based superparamagnetic nanoparticle. In some embodiments, the nanoparticle is a semiconductor nanocrystal or a semiconductor quantum dot, both of which can be used in optical imaging. In further embodiments, the nanoparticle can be a nanoshell, which comprises a gold layer over a core of silica.

2. Biological Functional Equivalents

A MAGE-B2 peptide epitope of the present disclosure may be modified to contain amino acid substitutions, insertions and/or deletions that do not alter their respective interactions with an HLA class protein, such as HLA-A2, binding regions. As a nonlimiting example, certain amino acids may be substituted for other amino acids in a MAGE-B2 peptide disclosed herein without appreciable loss of HLA-binding, as demonstrated by detectably unchanged peptide binding to HLA-A2. It is thus contemplated that a MAGE-B2 peptide disclosed herein (or a nucleic acid encoding such a peptide) which is modified in sequence and/or structure, but which is unchanged in biological utility or activity remains within the scope of the compositions and methods disclosed herein.

It is also well understood by the skilled artisan that, inherent in the definition of a biologically functional equivalent peptide, is the concept that there is a limit to the number of changes that may be made within a defined portion of the molecule while still maintaining an acceptable level of equivalent biological activity. Biologically functional equivalent peptides are thus defined herein as those peptides in which certain, not most or all, of the amino acids may be substituted. Of course, a plurality of distinct peptides with different substitutions may easily be made and used in accordance with the present disclosure.

The skilled artisan is also aware that where certain residues are shown to be particularly important to the biological or structural properties of a peptide, e.g., residues in specific epitopes, such residues may not generally be exchanged. This may be the case in the present disclosure, as a mutation in a MAGE-B2 peptide disclosed herein could result in a loss of species-specificity and in turn, reduce the utility of the resulting peptide for use in methods of the present disclosure. Thus, peptides which are antigenic (e.g., bind HLA-A*0201, HLA-A*0202, HLA-A*0203, HLA-A*0204, or HLA-A*0205 specifically) and comprise conservative amino acid substitutions are understood to be included in the present disclosure. Conservative substitutions are least likely to drastically alter the activity of a protein. A "conservative amino acid substitution" refers to replacement of amino acid with a chemically similar amino acid, i.e., replacing nonpolar amino acids with other nonpolar amino acids; substitution of polar amino acids with other polar amino acids, acidic residues with other acidic amino acids, etc.

Amino acid substitutions, such as those which might be employed in modifying a MAGE-B2 peptide disclosed herein are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. In some embodiments, the mutation may enhance TCR-pMHC interaction and/or peptide-MHC binding.

The present disclosure also contemplates isoforms of the MAGE-B2 peptide disclosed herein. An isoform contains the same number and kinds of amino acids as a peptide of the present disclosure, but the isoform has a different molecular structure. The isoforms contemplated by the present disclosure are those having the same properties as a peptide of the present disclosure as described herein.

Nonstandard amino acids may be incorporated into proteins by chemical modification of existing amino acids or by de novo synthesis of a peptide disclosed herein. A nonstandard amino acid refers to an amino acid that differs in chemical structure from the twenty standard amino acids encoded by the genetic code.

In some embodiments, the present disclosure contemplates a chemical derivative of a MAGE-B2 peptide disclosed herein. "Chemical derivative" refers to a peptide having one or more residues chemically derivatized by reaction of a functional side group, and retaining biological activity and utility. Such derivatized peptides include, for example, those in which free amino groups have been derivatized to form specific salts or derivatized by alkylation and/or acylation, p-toluene sulfonyl groups, carbobenzoxy groups, t-butylocycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include those peptides which comprise one or more naturally occurring amino acids derivatives of the twenty standard amino acids. For example, 4-hydroxyproline may be substituted for serine; and ornithine may be substituted for lysine.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The amino acids described herein are preferred to be in the "L" isomeric form. However, residues in the "D" isomeric form can be substituted for any L-amino acid residue, as long as the desired functional properties set forth herein are retained by the protein.

Preferred MAGE-B2 peptides or analogs thereof preferably specifically or preferentially bind a HLA-A2. Determining whether or to what degree a particular tumor antigen-specific peptide or labeled peptide, or an analog thereof, can bind an HLA-A2 and can be assessed using an in vitro assay such as, for example, an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immnunofluorescent assay (FA), nephelometry, flow cytometry assay, chemiluminescence assay, lateral flow immunoassay, u-capture assay, mass spectrometry assay, particle-based assay, inhibition assay and/or an avidity assay.

B. Engineered MAGE-B2-Specific Cells

In some embodiments, the present disclosure provides a MAGE-B2-specific TCR. The TCR may comprise alpha chain CDRs of SEQ ID NOs: 6-12 and/or beta chain CDRs of SEQ ID NOs: 13-17. The TCR may comprise an alpha chain with at least 90%, 91%, 92%, 93%, 94%, 95%, 96%, 97%, 98%, 99%, or 100%, identity or similarity to SEQ ID NOs: 2-3 and or a beta chain with at least 90%, 91%, 92%, 93%, 94%, 95%, 96%, 97%, 98%, 99%, or 100%, identity or similarity to SEQ ID NOs: 4-5. Also provided herein are polypeptides and polynucleotides encoding the alpha chain and/or beta chain of the MAGE-B2 TCRs provided herein. Further provided herein are cells, such as T cells, NK cells, invariant NK cells, NKT cells, MSCs, or iPS cells, engineered to express the MAGE-B2-specific TCR provided herein. These non-T cell effector immune cells may express a TCR together with CD3 molecules or other signaling domains linked to the TCR, which would initiate the signal transduction in these cells.

The engineered immune cells may be constructed using any of the many well-established gene transfer methods known to those skilled in the art. In certain embodiments, the engineered cells are constructed using viral vector-based gene transfer methods to introduce nucleic acids encoding a MAGE-B2-specific TCR. The viral vector-based gene transfer method may comprise a lentiviral vector, a retroviral vector, an adenoviral or an adeno-associated viral vector. In certain embodiments, the engineered cells are constructed using non-viral vector-based gene transfer methods to introduce nucleic acids encoding a MAGE-B2-specific TCR. The vector for the TCR may comprises the alpha chain polypeptide and the beta chain polypeptide, which may be linked by a linker domain or IRES sequence. The linker domain may comprise one or more cleavage sites, such as a Furin cleavage site and/or a P2A cleavage site, which may be separated by a spacer, such as SGSG or GSG. In certain embodiments, the non-viral vector-based gene transfer method comprises a gene-editing method selected from the group consisting of a zinc-finger nuclease (ZFN), a transcription activator-like effector nuclease (TALENs), and a clustered regularly interspaced short palindromic repeats (CRISPR)/CRISPR-associated protein 9 (Cas9) nuclease. In certain embodiments, the non-viral vector-based gene editing method comprises a transfection or transformation method selected from the group consisting of lipofection, nucleofection, virosomes, liposomes, polycation or lipid:nucleic acid conjugates, naked DNA, artificial virions, and agent-enhanced uptake of DNA.

C. Soluble TCRs and BiTEs

In addition, the present disclosure provides soluble TCRs which can be used to treat HLA-A2 positive cancer patients directly. Soluble bispecific T cell-engaging molecules (BiTEs) can be generated by linking the MAGE-B2 TCR to CD3-specific Fab fragments. These bispecific molecules can bind the tumor cell surface via their MAGE-B2 TCR binding to the peptide/HLA complex, and the CD3-specific Fab fragments would crosslink the TCR, such as on the target T cell. This would result in cellular activation and elimination of the target cell. Thus, these soluble bispecific TCR constructs can be used for treating the cancer patients directly.

Finally, the soluble TCR can be used as a probe for diagnostic evaluation of peptide/MHC in tumor cells or to direct therapeutic molecules to the tumor site. This soluble TCR molecule also could be labeled with tracers such as a fluorescent probe or radioactive probe, and then used for diagnostic evaluation of the presentation of peptide/MHC in tumor cells. Furthermore, this soluble TCR molecule could be linked with therapeutic molecules such as toxin, and then direct these therapeutic molecules to the tumor sites for the treatment of cancer patients.

In some embodiments, the present disclosure provides soluble TCRs, such as a MAGE-B2-specific TCR provided herein. Soluble TCRs may be used for investigating specific TCR-pMHC interactions or as a diagnostic tool to detect infection, or to detect autoimmune disease markers. Soluble TCRs may have applications in staining, for example to stain cells for the presence of a particular peptide antigen presented in the context of the MHC. Similarly, soluble TCRs can be used to deliver a therapeutic agent, for example a cytotoxic compound or an immunostimulating compound, to cells presenting a particular antigen. Soluble TCRs may also be used to inhibit T cells, for example, those reacting to an auto-immune peptide antigen. In some aspects, the TCR is linked to another molecule that delivers a cell in proximity to the tumor. In further aspects, the TCR delivers a toxin, a cytokine, costimulatory ligand, or inhibitor ligand and directs the molecule, cell or compound to the target cells expressing the peptide-MHC.

In some aspects, the present disclosure provides a soluble T cell receptor (sTCR), which comprises (i) all or part of a TCR α chain (e.g., SEQ ID NO: 2 or 3), except the transmembrane domain thereof, and (ii) all or part of a TCR β chain (e.g., SEQ ID NO: 4 or 5), except the transmembrane domain thereof, wherein (i) and (ii) each comprise a functional variable domain and at least a part of the constant domain of the TCR chain, and are linked by a disulfide bond between constant domain residues which is not present in native TCR.

In some aspects, the soluble TCR comprises a TCR α or γ chain extracellular domain dimerized to a TCR β or δ chain extracellular domain respectively, by means of a pair of C-terminal dimerization peptides, such as leucine zippers.

A soluble TCR of the present disclosure may be provided in substantially pure form, or as a purified or isolated preparation. For example, it may be provided in a form which is substantially free of other proteins.

A plurality of soluble TCRs of the present disclosure may be provided in a multivalent complex. Thus, the present disclosure provides, in one aspect, a multivalent TCR complex, which comprises a plurality of soluble TCRs as described herein. Each of the plurality of soluble TCRs is preferably identical.

In its simplest form, a multivalent TCR complex according to the present disclosure comprises a multimer of two or three or four or more T cell receptor molecules associated (e.g. covalently or otherwise linked) with one another, preferably via a linker molecule. Suitable linker molecules include, but are not limited to, multivalent attachment molecules such as avidin, streptavidin, neutravidin and extravidin, each of which has four binding sites for biotin. Thus, biotinylated TCR molecules can be formed into multimers of TCRs having a plurality of TCR binding sites. The number of TCR molecules in the multimer will depend upon the quantity of TCR in relation to the quantity of linker molecule used to make the multimers, and also on the presence or absence of any other biotinylated molecules. Preferred multimers are dimeric, trimeric or tetrameric TCR complexes.

Suitable structures for use in the present methods include membrane structures such as liposomes and solid structures which are preferably particles such as beads, for example latex beads. Other structures which may be externally coated with T cell receptor molecules are also suitable. Preferably, the structures are coated with T cell receptor multimers rather than with individual T cell receptor molecules.

In the case of liposomes, the T cell receptor molecules or multimers thereof may be attached to or otherwise associated with the membrane. Techniques for this are well known to those skilled in the art.

A label or another moiety, such as a toxic or therapeutic moiety, may be included in a multivalent TCR complex of the present disclosure. For example, the label or other moiety may be included in a mixed molecule multimer. An example of such a multimeric molecule is a tetramer containing three TCR molecules and one peroxidase molecule. This could be achieved by mixing the TCR and the enzyme at a molar ratio of 3:1 to generate tetrameric complexes, and isolating the desired complex from any complexes not containing the correct ratio of molecules. These mixed molecules could contain any combination of molecules, provided that steric hindrance does not compromise or does not significantly compromise the desired function of the molecules. The positioning of the binding sites on the streptavidin molecule is suitable for mixed tetramers since steric hindrance is not likely to occur.

The TCR (or multivalent complex thereof) of the present disclosure may alternatively or additionally be associated with (e.g. covalently or otherwise linked to) a therapeutic agent which may be, for example, a toxic moiety for use in cell killing, or an immunostimulating agent such as an interleukin or a cytokine. A multivalent TCR complex of the present disclosure may have enhanced binding capability for a TCR ligand compared to a non-multimeric T cell receptor heterodimer. Thus, the multivalent TCR complexes according to the present disclosure are particularly useful for tracking or targeting cells presenting particular antigens in vitro or in vivo, and are also useful as intermediates for the production of further multivalent TCR complexes having such uses. The TCR or multivalent TCR complex may therefore be provided in a pharmaceutically acceptable formulation for use in vivo.

The present disclosure also provides a method for delivering a therapeutic agent to a target cell, which method comprises contacting potential target cells with a TCR or multivalent TCR complex in accordance with the present disclosure under conditions to allow attachment of the TCR or multivalent TCR complex to the target cell, said TCR or multivalent TCR complex being specific for the TCR ligand and having the therapeutic agent associated therewith.

In particular, the soluble TCR or multivalent TCR complex can be used to deliver therapeutic agents to the location of cells presenting a particular antigen. This would be useful in many situations and, in particular, against tumors. A therapeutic agent could be delivered such that it would exercise its effect locally but not only on the cell it binds to. Thus, one particular strategy envisages anti-tumor molecules linked to T cell receptors or multivalent TCR complexes specific for tumor antigens.

Many therapeutic agents could be employed for this use, for instance radioactive compounds, enzymes (perforin for example) or chemotherapeutic agents (cisplatin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

The soluble TCRs of the present disclosure may be used to modulate T cell activation by binding to specific TCR ligand and thereby inhibiting T cell activation. Autoimmune diseases involving T cell-mediated inflammation and/or tissue damage would be amenable to this approach, for example type I diabetes. Knowledge of the specific peptide epitope presented by the relevant pMHC is required for this use.

The use of the soluble TCRs and/or multivalent TCR complexes of the present disclosure in the preparation of a composition for the treatment of cancer or autoimmune disease is also envisaged.

Also provided is a method of treatment of cancer or autoimmune disease comprising administration to a patient in need thereof of an effective amount of the soluble TCRs and/or multivalent TCR complexes of the present disclosure.

As is common in anti-cancer and autoimmune therapy the soluble TCRs of the present disclosure may be used in combination with other agents for the treatment of cancer and autoimmune disease, and other related conditions found in similar patient groups.

III. Methods of Use

In another aspect, provided herein are methods for treating cancer in a subject comprising administering to the subject a therapeutically effective amount of the population of MAGE-B2 TCR-specific cells, such as T cells, NK cells, invariant NK cells, NKT cells, MSCs, or iPS cells, produced by any of the methods provided herein. The cells may be adoptively transferred to a subject with a cancer from which TILs may be cultured from or tumor antigen-specific CTLs can be generated from in vitro.

Provided herein are methods for treating or delaying progression of cancer in an individual comprising administering to the individual an effective amount a MAGE-B2-specific T cell therapy. Adoptive T cell therapies with genetically engineered TCR-transduced T cells (conjugate TCR to other bioreactive proteins (e.g., anti-CD3)) are also provided herein. In further embodiments, methods are provided for the treatment of cancer comprising immunizing a subject with a purified tumor antigen or an immunodominant tumor antigen-specific peptide.

The MAGE-B2 peptide provided herein can be utilized to develop cancer vaccines or immunogens. These peptide specific vaccines or immunogens can be used for immunizing cancer patients directly to induce anti-tumor immuno-response in vivo, or for expanding antigen specific T cells in vitro with peptide or coded polynucleotide loaded APC stimulation. These large number of T cells can be adoptively transferred to patients to induce tumor regression.

Tumors for which the present treatment methods are useful include any malignant cell type expressing MAGE-B2, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli;

solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

In certain embodiments, the method further comprises a step of performing lymphodepletion prior to administration of the therapeutically effective amount of the population of MAGE-B2 TCR cells. In certain embodiments, the lymphodepletion comprises non-myeloablative lymphodepleting chemotherapy. In certain embodiments, the non-myeloablative lymphodepleting chemotherapy comprises administration of cyclophosphamide and fludarabine.

In certain embodiments, the method further comprises a step of administering a T-cell growth factor that promotes the growth and activation of autologous T cells to the subject, either concomitantly with the autologous T cells or subsequently to the autologous T cells. In certain embodiments, the T cell growth factor comprises any suitable growth factor that promotes the growth and activation of the autologous T-cells. In certain embodiments, the T cell growth factor is selected from the group consisting of interleukin (IL)-2, IL-7, IL-15, and IL-12, and combinations thereof (e.g., IL-2 and IL-7, IL-2 and IL-15, IL-7 and IL-15, IL-2, IL-7 and IL-15, IL-12 and IL-7, IL-12 and IL-15, or IL-12 and IL-2).

In certain embodiments, the therapeutically effective amount of the population of MAGE-B2 TCR-specific cells produced by any of the methods provided herein is administered to the subject intravenously, intratumorally, or intraperitoneally. The appropriate dosage of the cell therapy may be determined based on the type of cancer to be treated, the severity and course of the disease, the clinical condition of the individual, the individual's clinical history and response to the treatment, and the discretion of the attending physician.

A. Combination Therapies

In certain embodiments, the methods provided herein further comprise a step of administering at least one additional therapeutic agent to the subject. All additional therapeutic agents disclosed herein will be administered to a subject according to good clinical practice for each specific composition or therapy, taking into account any potential toxicity, likely side effects, and any other relevant factors.

In certain embodiments, the additional therapy may be immunotherapy, radiation therapy, surgery (e.g., surgical resection of a tumor), chemotherapy, bone marrow transplantation, or a combination of the foregoing. The additional therapy may be targeted therapy. In certain embodiments, the additional therapy is administered before the primary treatment (i.e., as adjuvant therapy). In certain embodiments, the additional therapy is administered after the primary treatment (i.e., as neoadjuvant therapy.

In certain embodiments, the additional therapy comprises an immunotherapy. In certain embodiments, the immunotherapy comprises an immune checkpoint inhibitor. In certain embodiments, the immune checkpoint inhibitor inhibits an immune checkpoint protein selected from the group consisting of programmed cell death pathway 1 (PD-1/CD279) and its ligands (PD-L1/CD274 and PD-L2/CD273), cytotoxic T lymphocyte-associated antigen 4 (CTLA-4/CD152), lymphocyte-activation gene 3 (LAG-3/CD223), B and T lymphocyte attenuator (BTLA), T cell immunoreceptor with Ig and immunoreceptor tyrosine-based inhibitory motif (ITIM) domains (TIGIT), T cell immunoglobulin domain and mucin domain 3 (TIM-3/HAVcr2), killer immunoglobulin-like receptor (KIR/CD158), V-domain immunoglobulin suppressor of T cell activation (VISTA), and the adenosine A2a receptor (A2aR).

In certain embodiments, the immune checkpoint inhibitor is a PD-1 binding antagonist. In certain embodiments, the PD-1 binding antagonist is an anti-PD-1 antibody. In certain embodiments, the anti-PD-1 antibody is selected from the group consisting of nivolumab, pembrolizumab, and CT-011. In certain embodiments, the PD-1 binding antagonist is an immunoadhesin (e.g., an immunoadhesin comprising an extracellular or PD-1 binding portion of PDL1 or PDL2 fused to an immunoglobulin constant region (e.g., an Fc region of an immunoglobulin sequence).

In certain embodiments, the immune checkpoint inhibitor is a CTLA-4 binding antagonist. In certain embodiments, the CTLA-4 binding antagonist is an anti-CTLA-4 antibody. In certain embodiments, the anti-CTLA-4 antibody is selected from the group consisting of ipilimumab and tremelimumab.

In certain embodiments, the additional therapeutic agent comprises treatment with radiotherapy. In certain embodiments, the radiotherapy is selected from the group consisting of gamma rays (γ-rays), X-rays, microwaves, proton beam irradiation, ultraviolet irradiation, and the directed delivery of radioisotopes to the tumor. In certain embodiments, the radiotherapy comprises treatment with X-rays. In certain embodiments, the X-rays are administered in daily doses of 50 to 200 roentgens over a period of three to four weeks. In certain embodiments, the X-rays are administered in a single dose of 2000 to 6000 roentgens. In certain embodiments, the radiotherapy comprises directed delivery of radioisotopes to the tumor. Dosage ranges for radioisotopes vary widely depending on the half-life of the isotope, the strength and type of radiation emitted, and the degree of uptake by tumor cells, but determination of an appropriate therapeutically effective dose is within the level of ordinary skill in the art.

In certain embodiments, the additional therapeutic agent comprises administration of agents for the treatment of side-effects associated with the primary treatment (e.g., nausea, cachexia, and the like). In certain embodiments, the additional therapy comprises an immunotherapy. In certain embodiments, the additional therapy comprises radiation therapy. In some embodiments, the radiotherapy comprises gamma irradiation. In certain embodiments, the additional therapy comprises surgery. In certain embodiments, the additional therapy comprises a combination of radiation therapy and surgery. In certain embodiments, the additional therapy comprises treatment with a class of chemotherapeutic agent selected from the group consisting of alkylating agents, anthracyclines, cytoskeletal disruptors, epothilones, histone deacetylase inhibitors, topoisomerase I inhibitors, topoisomerase II inhibitors, kinase inhibitors, nucleotide analogs and nucleotide precursor analogs, peptide antibiotics, platinum-based compounds, retinoids, *vinca* alkaloids and derivatives thereof.

The additional therapies contemplated herein may be administered before, after, or concurrently with administration of the compositions provided herein. In certain embodiments, the additional therapy is administered before the compositions provided herein. In certain embodiments, the additional therapy is administered after the compositions provided herein. In certain embodiments, the additional therapy is administered at one or more intervals before or after administration of the compositions provided herein. Determination of an appropriate interval for administration of an additional therapy such that the subject being treated benefits from the combination therapy is within the level of ordinary skill in the art.

B. Pharmaceutical Compositions

In another aspect, provided herein are pharmaceutical compositions and formulations comprising MAGE-B2 TCR-specific cells and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of aqueous solutions, such as normal saline (e.g., 0.9%) and human serum albumin (e.g., 10%). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e g Zinc-protein complexes); and/or non-ionic surfactants such as polyethylene glycol (PEG).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Production and Characterization of MAGE-B2-Specific T Cells

The expression of MAGE-B2 was analyzed in lung cancer cell lines and immortalized normal human small air epithelial cells (HSAEC1-KT and HSAEC2-KT) (FIG. 1). MAGE-B2 protein was found to be strongly expressed in most lung cancer cell lines and there almost no expression was observed in the normal ling cell lines.

To generate MAGE-B2 specific CD8+ CTLs, dendritic cells were pulsed with RNA encoding the MAGE-B2 HLA-A2 restricted epitope. Next, T cells were stimulated with the pulsed dendritic cells and the CD8$^+$ tetramers with detected by flow cytometry. The T cells were then sorted, cloned and expanded by the random expansion protocol (REP). The T cells were then characterized by functional screening before cloning of the functional MAGE-B2-specific TCR.

Figure 2:
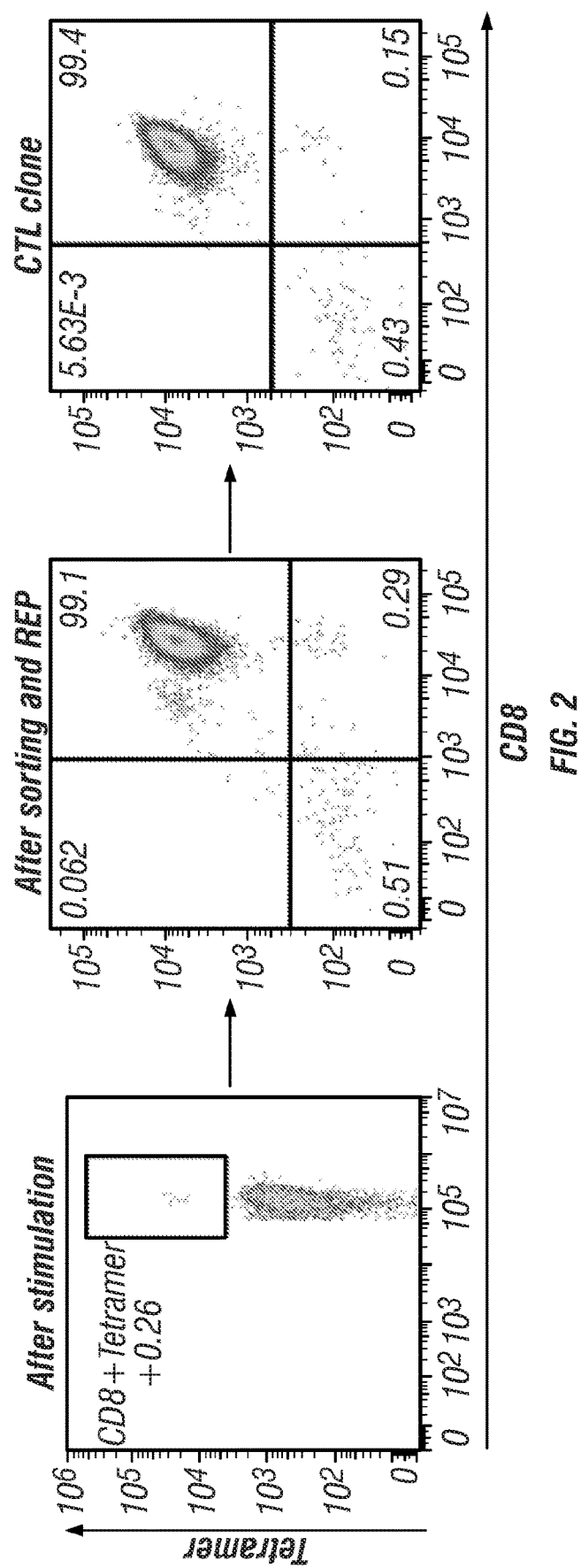
FIG. 2: MAGE-B2 HLA-A2 restricted peptide-specific cytotoxic T lymphocyte (CTL) generation. Detection of T cell population comprising tetramer with HLA-A2 restricted MAGE-B2 epitope (GVYDGEEHSV) (left). Sorting and expansion of CD8$^+$tetramer$^+$ population with rapid expansion protocol (REP) (middle). Generation of CTL clones using the limiting dilution method (right).

Thus, the MAGE-B2 HLA-A2 restricted epitope was used for the generation of MAGE-B2-specific cytotoxic T lymphocytes (CTLs). Naïve T cells were derived from a healthy HLA-A2 donor and stimulated with autogeneous mature dendritic cells (mDC) pulsed with full length MAGE-B2 RNA. After two rounds of stimulation, a tetramer with the HLA-A2 restricted MAGE-B2 epitope (GVYDGEEHSV; SEQ ID NO: 1) was used to detect the T cell population which recognized the epitope. The CD8$^+$tetramer$^+$ population was then sorted and expanded with the rapid expansion protocol (REP) to generate the CTL cell line. The correlated CTL clones were generated using the limiting dilution method. Over 99% of the cells were observed to be CD8$^+$ and tetramer$^+$ (FIG. 2).

Figure 3A:
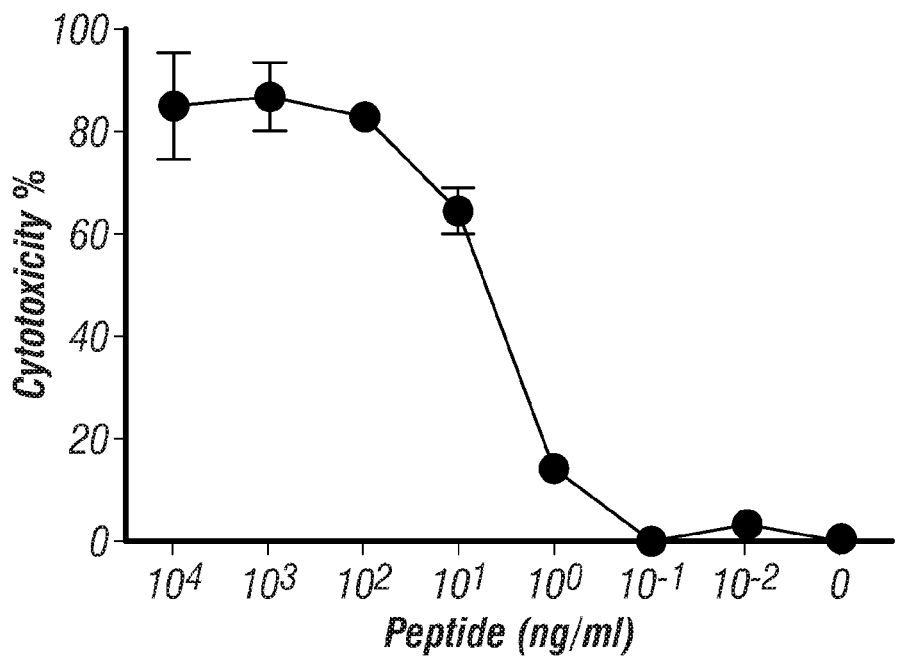
FIGS. 3A-3D: Killing ability detection of MAGE-B2 CTL clone.
Figure 3B:
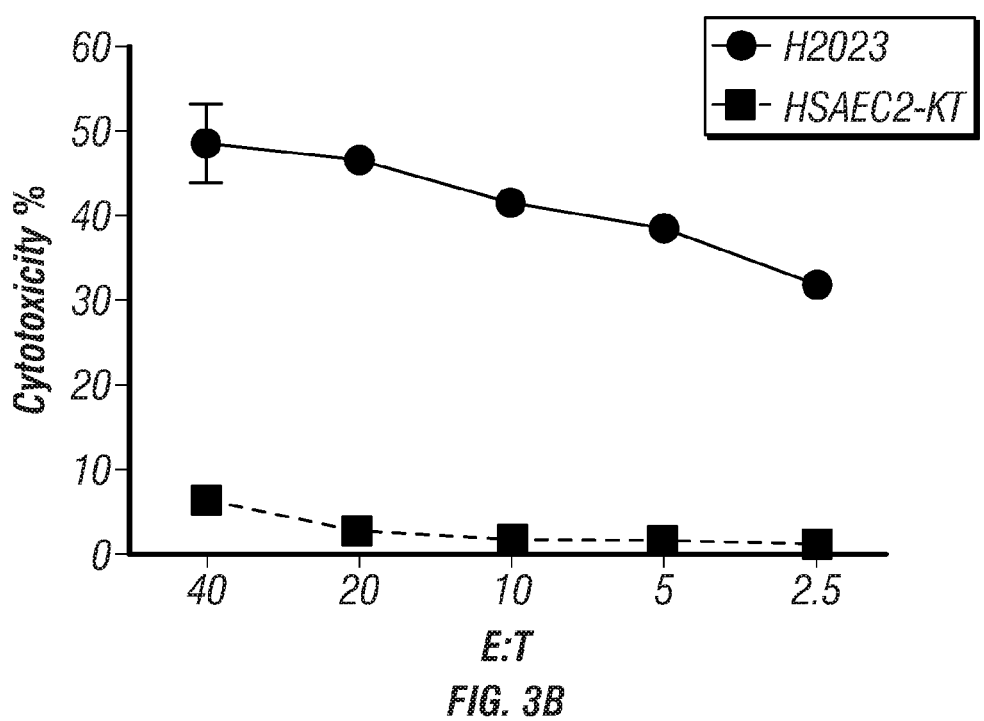
Figure 3C:
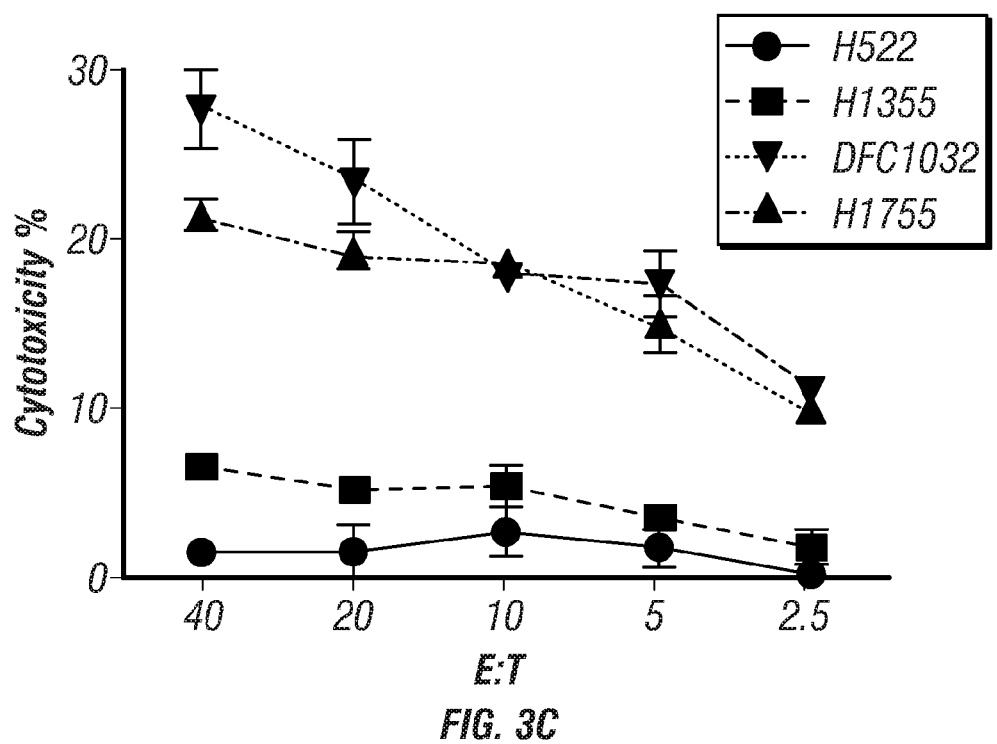
Figure 3D:
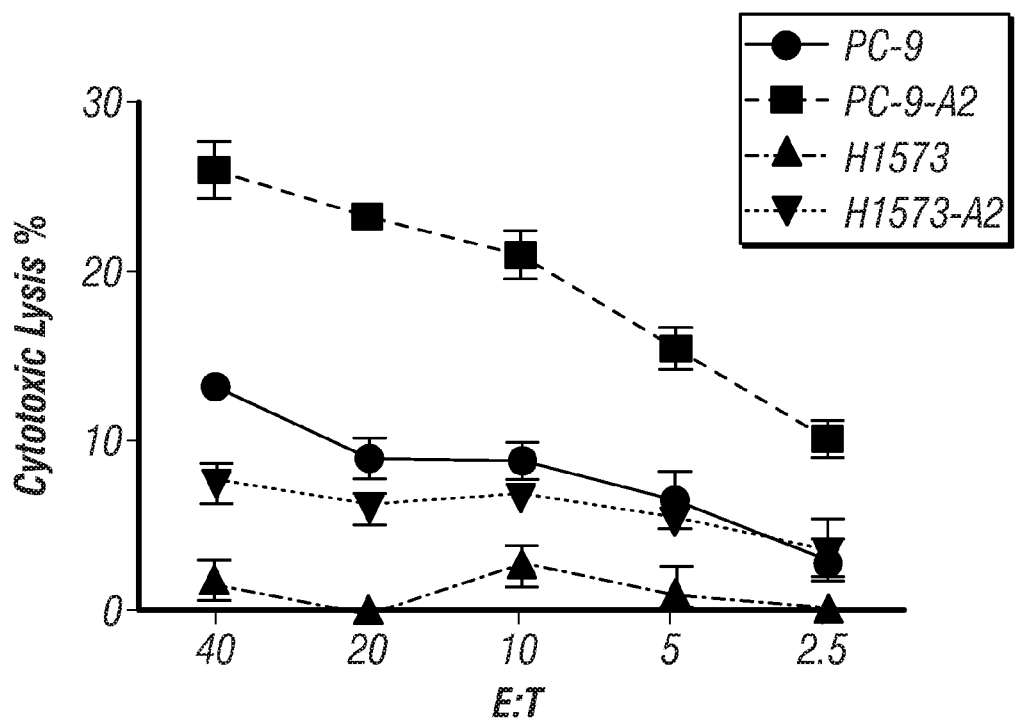

Functional avidity of the MAGE-B2-specific T cells was tested next. In a peptide titration assay, T2 cells were pulsed with different concentration of MAGE-B2 peptide (from 10 pg/ml to 10 µg/ml) (FIG. 3A). The T2 cells were used as target cells and co-cultured with the isolated MAGE-B2 CTL clone (E:T=20:1). The cytotoxic activity (FIG. 3B) of the CTL clone was measured against the lung cancer cell line H2023 (HLA-A*0201) and the normal lung cell line HSAEC2-KT (HLA-A*0201). The target cells were co-cultured with the MAGE-B2 CTL clone at different E:T ratios. The cytotoxic activity was detected with the standard $^{51}$Cr release assay. The MAGE-B2 CTL clone was observed to be cytotoxic against the lung cancer cell line but not normal lung cell line (FIG. 3B). In addition, the HLA-A2$^+$ lung cancer cell lines H522, H1355, H1755 and DFC-1032 were used as target cells and co-cultured with the MAGE-B2 CTL clone at different E:T ratios and cytotoxicity was measured. The MAGE-B2 CTL clone was observed to be cytotoxic to the lung cancer cell lines DFC-1032 and H1755 (FIG. 3C). Finally, the cytotoxicity of the CTL clone was assessed against the parental lung cancer cell lines PC-9 and H1573 as well as both cell lines with HLA-A2 forced expression. Greater cytotoxic activity was observed against the cells lines with HLA-A2 forced expression as compared to the parental PC-9 and H1573 cells (FIG. 3D).

Figure 4:
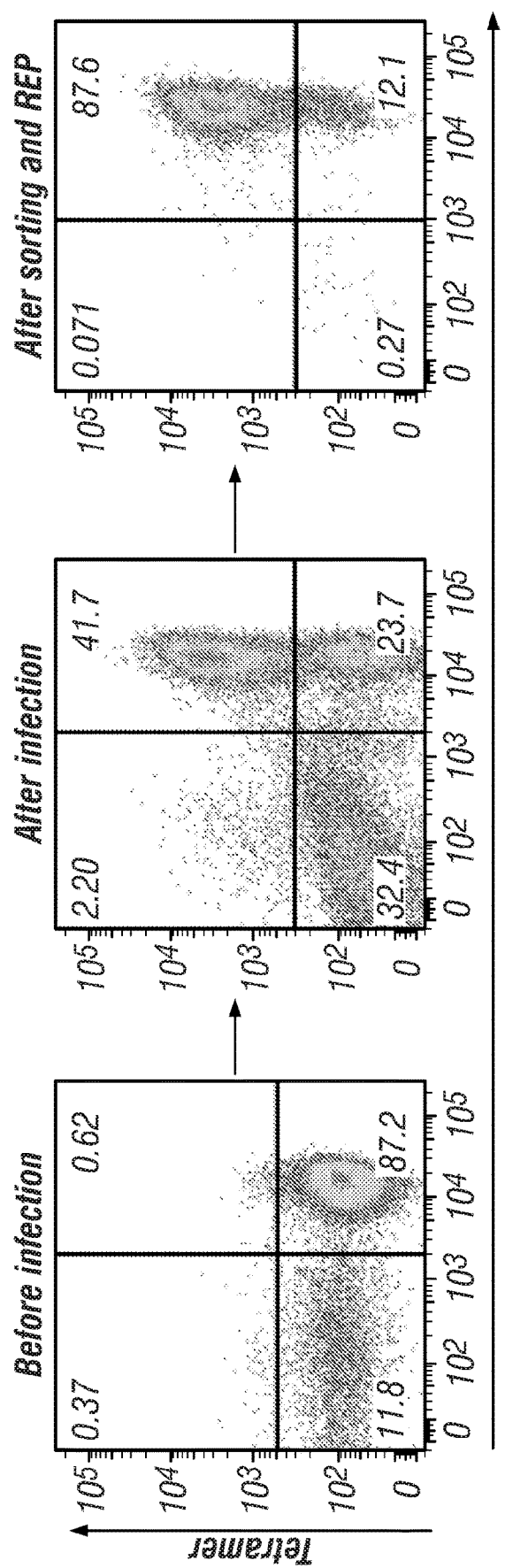
FIG. 4: MAGE-B2 T cell receptor engineered T cells (TCR-T) generation. The activated allogeneic PBMCs (left) were infected with the retrovirus and a CD8$^+$tetramer$^+$ appeared after infection (middle). The TCR-T cell line was developed by sorting and expanding the CD8$^+$tetramer$^+$ population (right).

To generate MAGE-B2 TCR engineered T cells (TCR-T), the TCR from the MAGE-B2 CTL clone was cloned out and inserted into the retrovirus vector pMSGV1. A linker fragment containing a Furin cleavage site, a SGSG linker and a P2A cleavage site was inserted between the TCR-β chain and TCR-α chain to guarantee that both chains were expressed equally under the MSCV promoter. The recombinant retrovirus was generated by co-transfection of the retrovirus vector and an envelope vector RD114 into the package cell line GP2-293. Two to three days after transfection, the supernatant containing the retrovirus was used to infect the allogeneic PBMCs which were activated for two days with 50 ng/mg OKT3 and 300 U/ml IL-2 stimulation. The infection was performed one more time after one day of the first infection. After 5 days, a clear CD8$^+$Tetramer$^+$ population was detected by flow cytometry (FIG. 4). The TCR-T cell line was developed by sorting and expanding the CD8$^+$tetramer$^+$ population using the rapid expansion protocol.

Figure 5A:
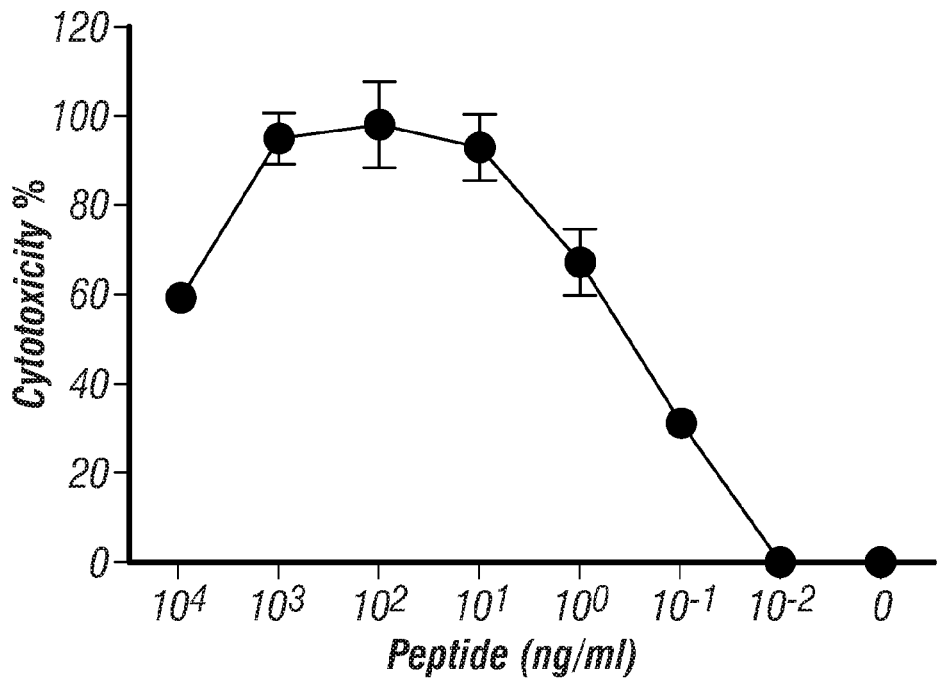
FIGS. 5A-B: MAGE-B2 TCR-T killing ability assay.
Figure 5B:
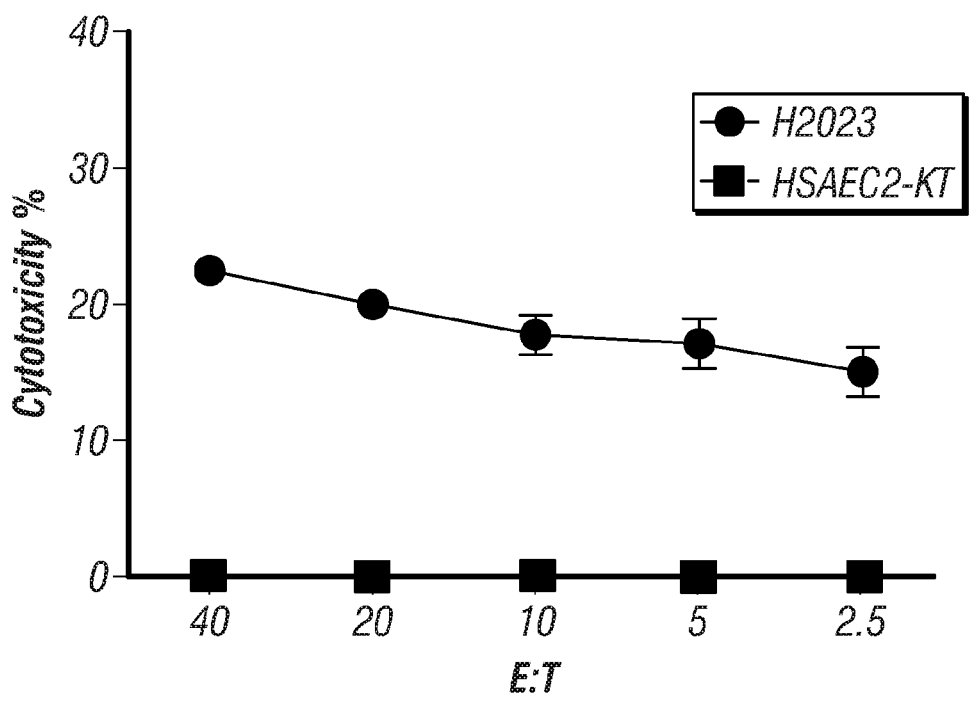

A peptide titration assay was performed with T2 cells pulsed with different concentrations of MAGE-B2 peptide (from 10 pg/ml to 10 µg/ml) as target cells. The T2 cells were co-cultured with the MAGE-B2 TCR-T cell line (E:T=20:1). The cytotoxicity was detected with the standard $^{51}$Cr release assay (FIG. 5A). The cytotoxicity of the MAGE-B2 TCR-T against lung cancer cell line H2023 (HLA-A*0201) and normal lung cell line HSAEC2-KT (HLA-A*0201) was also assessed (FIG. 5B). The lung cancer cell line H2023 and the normal lung cell line HSAEC2-KT were co-cultured with the MAGE-B2 TCR-T cells at different E:T ratios. The killing activity was detected with the standard $^{51}$Cr release assay. It was observed that the MAGE-B2 TCR-T cell line was specifically cytotoxic to the lung cancer cell line.

Figure 6:
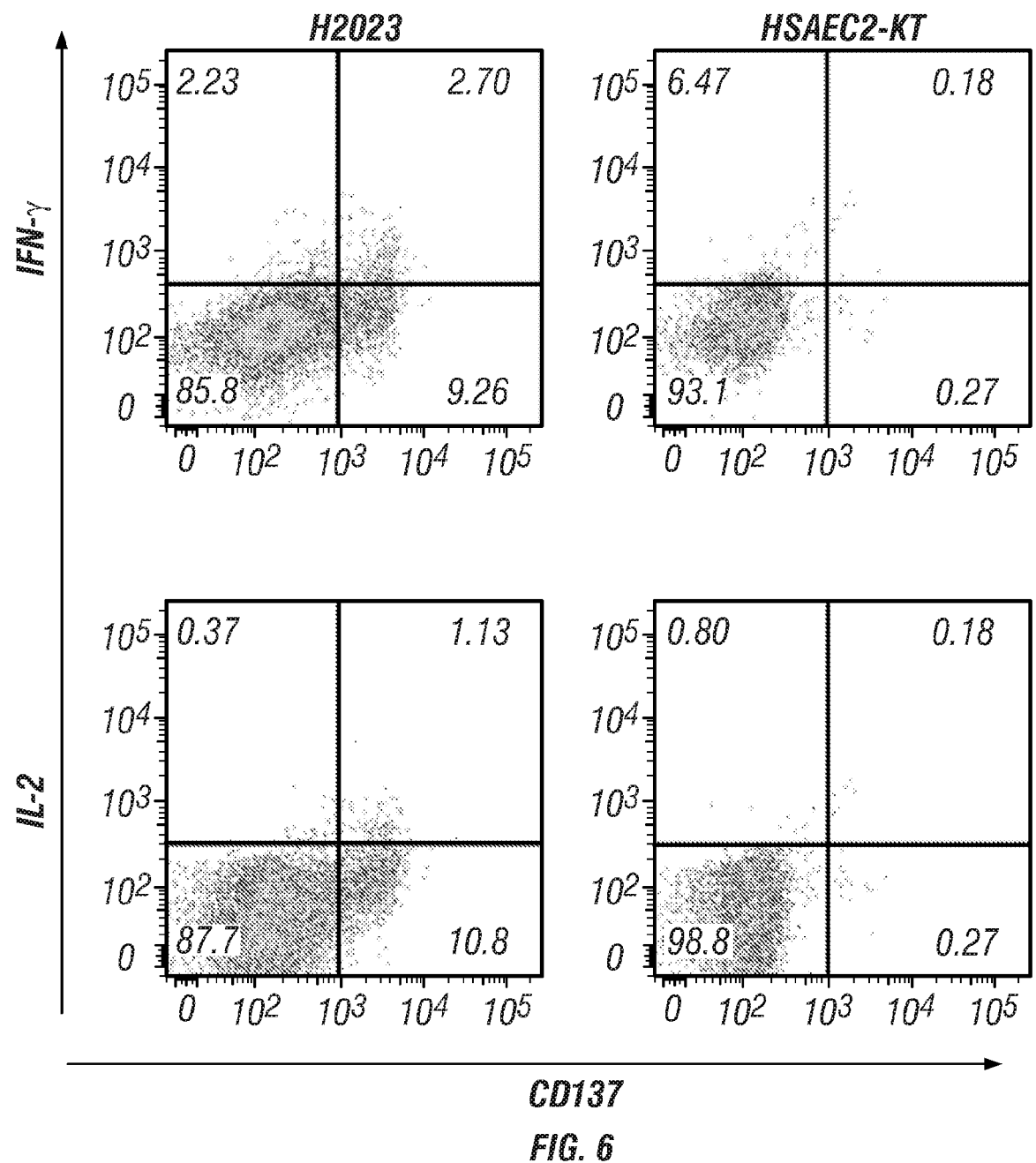
FIG. 6: MAGE-B2 TCR-T functional detection with intracellular cytokine staining (ICS).
Figure 6:
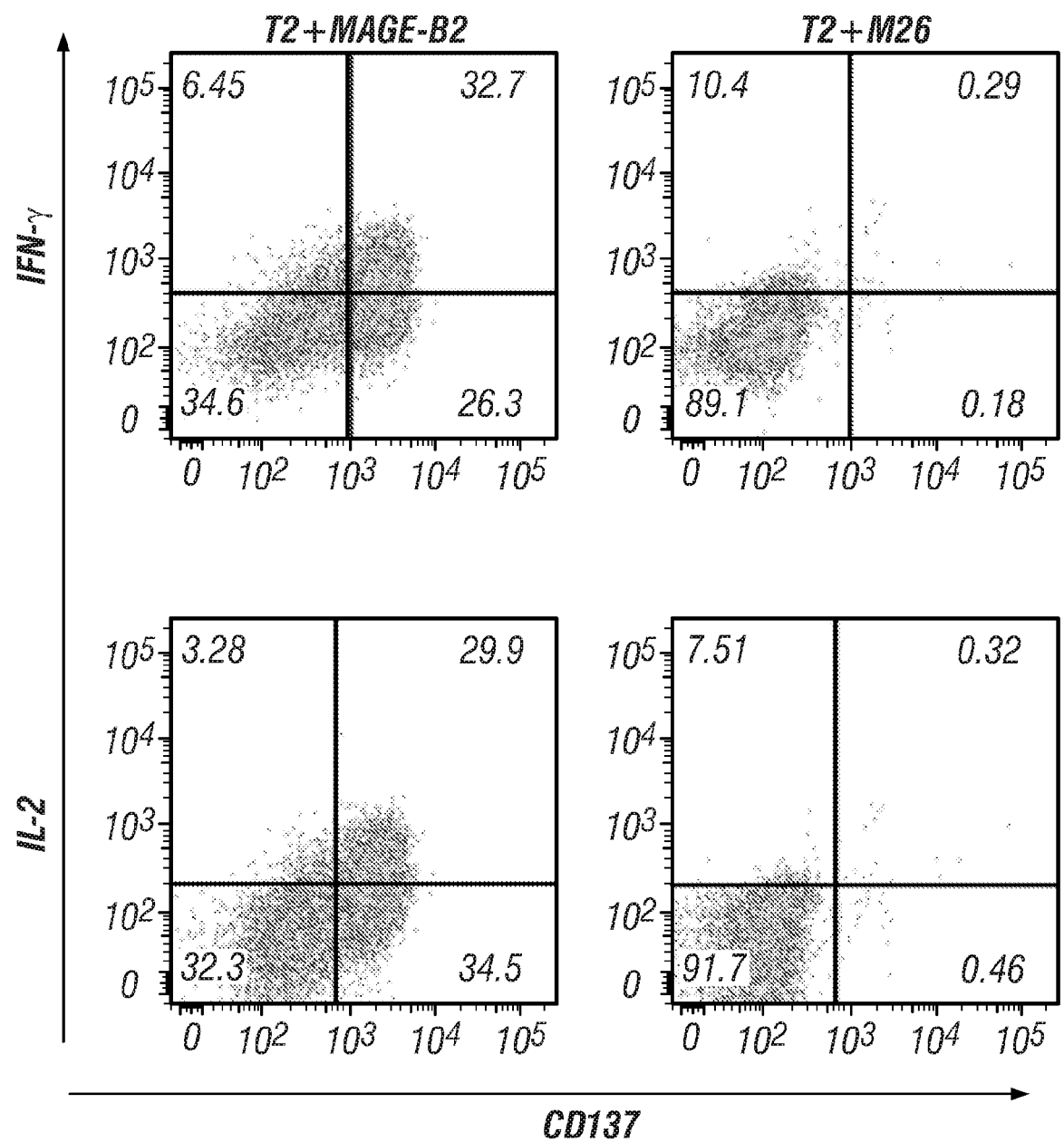
Figure 6:
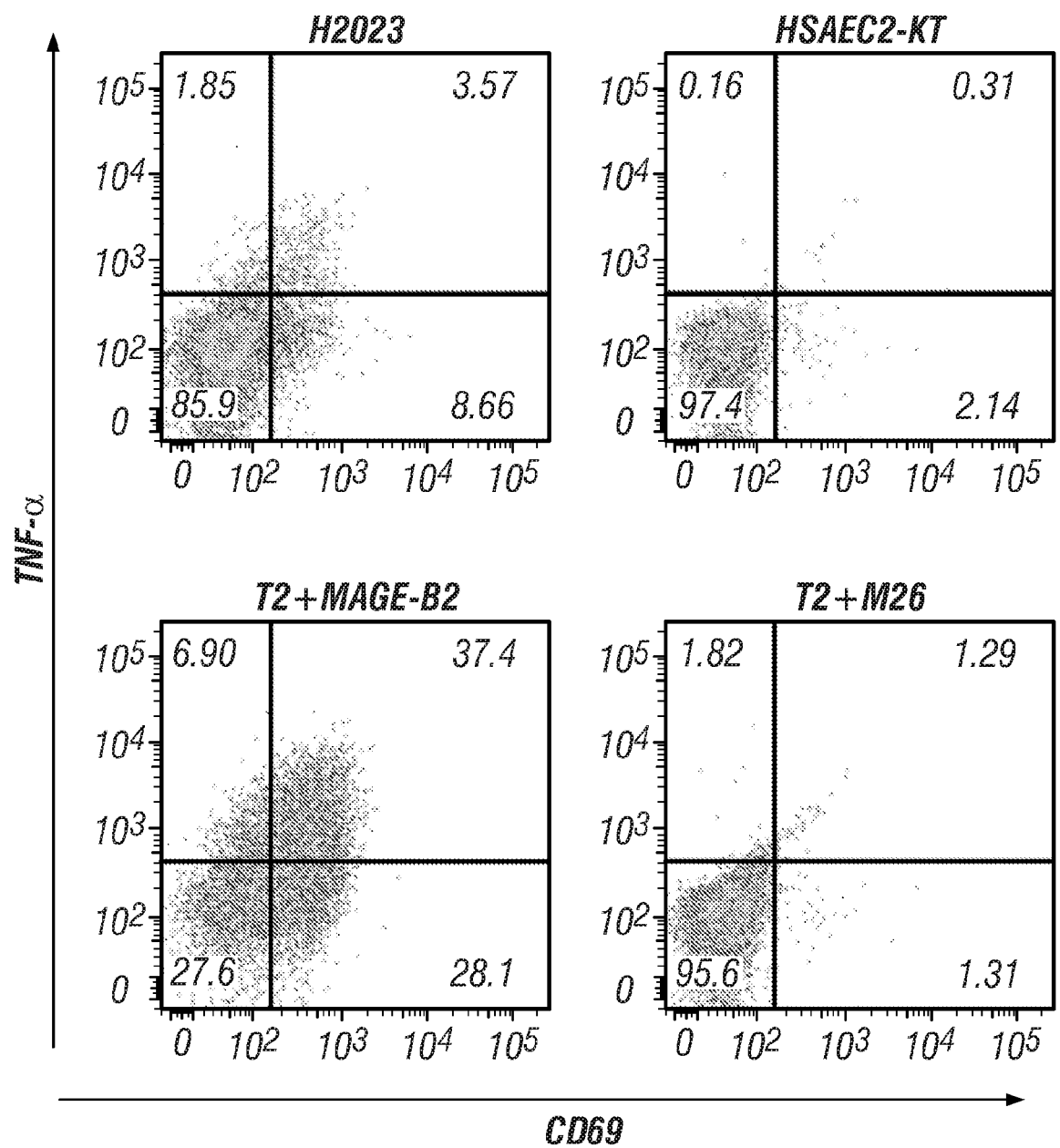

Finally, the MAGE-B2 TCR-T cells were functionally characterized by intracellular cytokine staining (ICS). The MAGE-B2 TCR-T cell line was co-cultured with the lung cancer cell line H2023, normal lung cell line HSAEC2-KT, T2 pulsed with MAGE-B2 peptide, as well as T2 pulsed with MART-1 peptide M26. The IFN-γ, TNF-α, IL-2 and antigen specific response markers CD137 and CD69 were detected by the ICS assay. After co-culturing, IFN-γ, TNF-α, IL-2, CD137 and CD69 levels of MAGE-B2 TCR-T cell line were significantly enhanced when the TCR-T cells were co-cultured with the lung cancer cell line H2023 or T2 pulsed with MAGE-B2 peptide, compared with co-culture with the normal lung cell line HSAEC2-KT or T2 pulsed with control peptide M26 (FIG. 6).

Thus, the MAGE-B2 TCR-T cells may be used for the treatment of HLA-A2 (e.g., HLA-A*0201, HLA-A*0202, HLA-A*0203, HLA-A*0204, or HLA-A*0205) positive patients with advanced or recurrent cancer, such as by generating and expanding TCR gene modified CTLs using allogeneic PBMCs. After functional detection (e.g., phenotype and cytotoxicity), the TCR modified T cells are infused to patients.

Example 2—Materials and Methods

Generate T Cell Clone:

Full length MAGE-B2 RNA was transfected to matured dendritic cells (DCs) derived from an HLA-A2 healthy donor. The RNA transfected DC were co-cultured with naïve T cell at the ratio of DC:T=1:10 in the presence of IL-21. After one week, the RNA-transfected DC were used to re-stimulate the T cells. After two rounds of stimulation, the CD8 and tetramer double positive T cell population was sorted and expanded with the rapid expansion protocol (REP). The T cell clones were generated with the limiting dilution method. The high activity CTL clones were screened via a cytotoxicity assay against cancer cells.

T Cell Receptor (TCR) Cloning and Retrovirus Expression Vector Construction:

The TCR (including alpha chain and beta chain) were cloned using the 5'-RACE method according manufacturer's instructions. The TCR V-alpha and TCR V-beta usage were identified with the IMGT/V-QUEST annotation tool. For the TCR expression retrovirus vector construction, the forward primers were designed according to the TCR V-alpha or beta usage. The reverse primers were designed according to the sequence of TCR alpha or beta constant region. Expression cassettes containing the alpha- and beta-TCR chains separated by the Furin and P2A linker peptide were generated and the full-length PCR products were cloned into the retrovirus vector pMSGV1. The cloned DNA sequences were verified with sequencing.

Retrovirus Generation and Infection of Human Peripheral Blood Lymphocytes (PBL):

The pMSGV1 vector containing the TCR and the envelope vector RD114 were co-transfected to the package cell line GP2-293. After transfection for 6-8 hours, the medium was refreshed. The supernatant was harvested 24 hours later and was added to the 6 well plate which has been coated with 20 µg/mL RetroNectin followed by centrifugation (2000×g) at 32° C. for 2 hours. The supernatant was removed then and the PBL which were activated with 50 ng/ml OKT3 and 300 U/ml IL-2 for two days were added to the retrovirus loaded plate followed by centrifugation (1000×g) at 32° C. for 10 min Cells were then incubated overnight at 32° C., and the procedure was repeated the following day (total of two transductions). After that, the cells were expanded at 37° C. in a 5% CO2 incubator and split as necessary.

TCR Engineered T Cell Clone Generation:

After infection, the CD8+ and tetramer+ T cell population were sorted and expanded with rapid expansion protocol (REP).

$^{51}$Cr Release Assay:

The killing ability of the TCR engineered T cell or CTL clone to lyse HLA-A2 tumor targets was measured using a standard $^{51}$Cr release assay. Tumor cells or normal cells were labeled for 2 h at 37° C. with 200 µCi of $^{51}$Cr. Labeled target cells were washed and then incubated with effector cells at the different ratios for 4 h at 37° C. in 0.2 ml of complete medium. Harvested supernatants were counted using automatic gamma counter. Maximal and spontaneous $^{51}$Cr release was determined by incubating the labeled target cells in either trypan lysis buffer or medium for 4 h at 37° C. Each data point was determined as an average of quadruplicate wells. The percent specific lysis was calculated as follows: % killing=((specific release−spontaneous release)/(total release−spontaneous release))×100.

Intracellular Cytokine Staining (ICS) Assay:

The T cells were incubated with target cells at 10:1 ration in the presence of brefeldin A (BFA) at 37° C. overnight. After co-culturing, the T cells were harvested and washed. The cells were stained with flow antibody anti surface marker first. After that, the cells were washed and fixed with Fix Buffer and then were permeabilized using Permeabilizing Solution. Permeabilized cells are then stained with intracellular cytokine flow antibody. Finally, the level of cytokine producing in the cells was analyzed using FACS.

Figure 7:
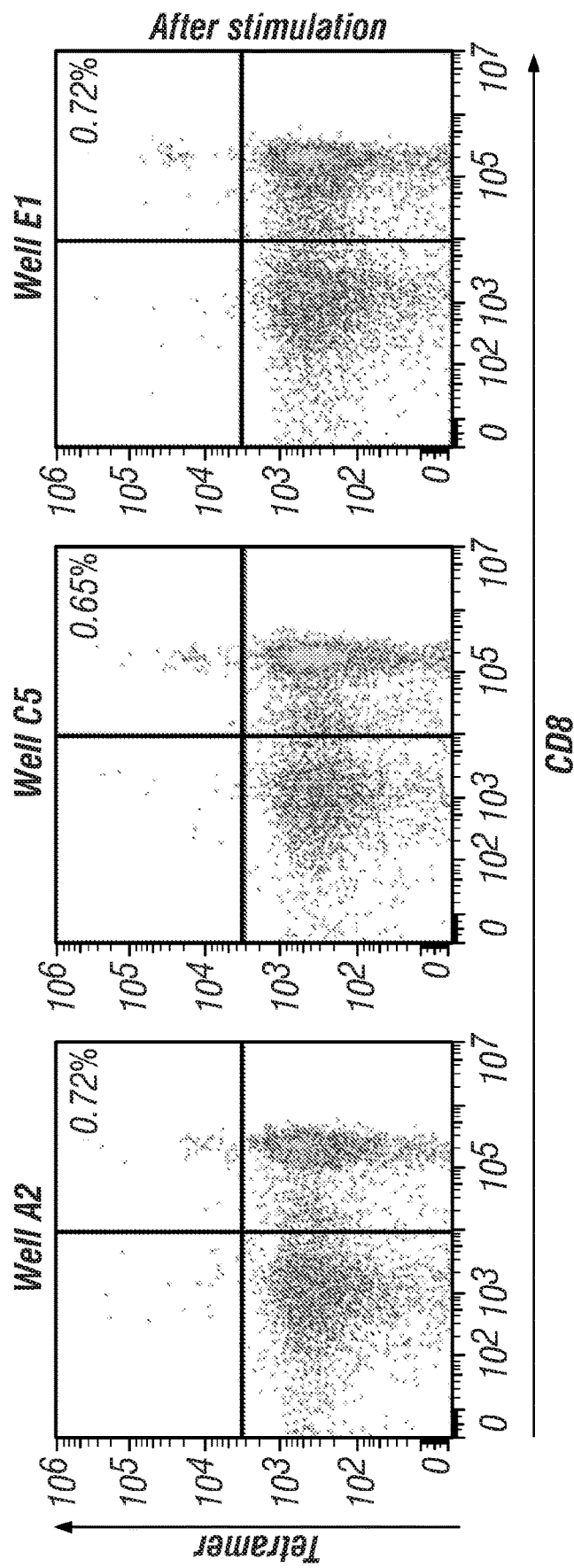
FIG. 7: Representative generation of MAGE-B2 specific T cell products from dendritic cell-T cell (DC-T) co-culturing system with healthy donor PBMCs. Small CD8$^+$/Tetramer$^+$ populations were observed in 3 wells of one 48 well plate after 2 stimulations using MB2-231 peptide pulsed DC. The 3 positive wells were sorted separately using tetramer guided sorting technology and underwent 1 or 2 rounds of expansions with REP. CD8 and tetramer staining of the final products is shown.
Figure 7:
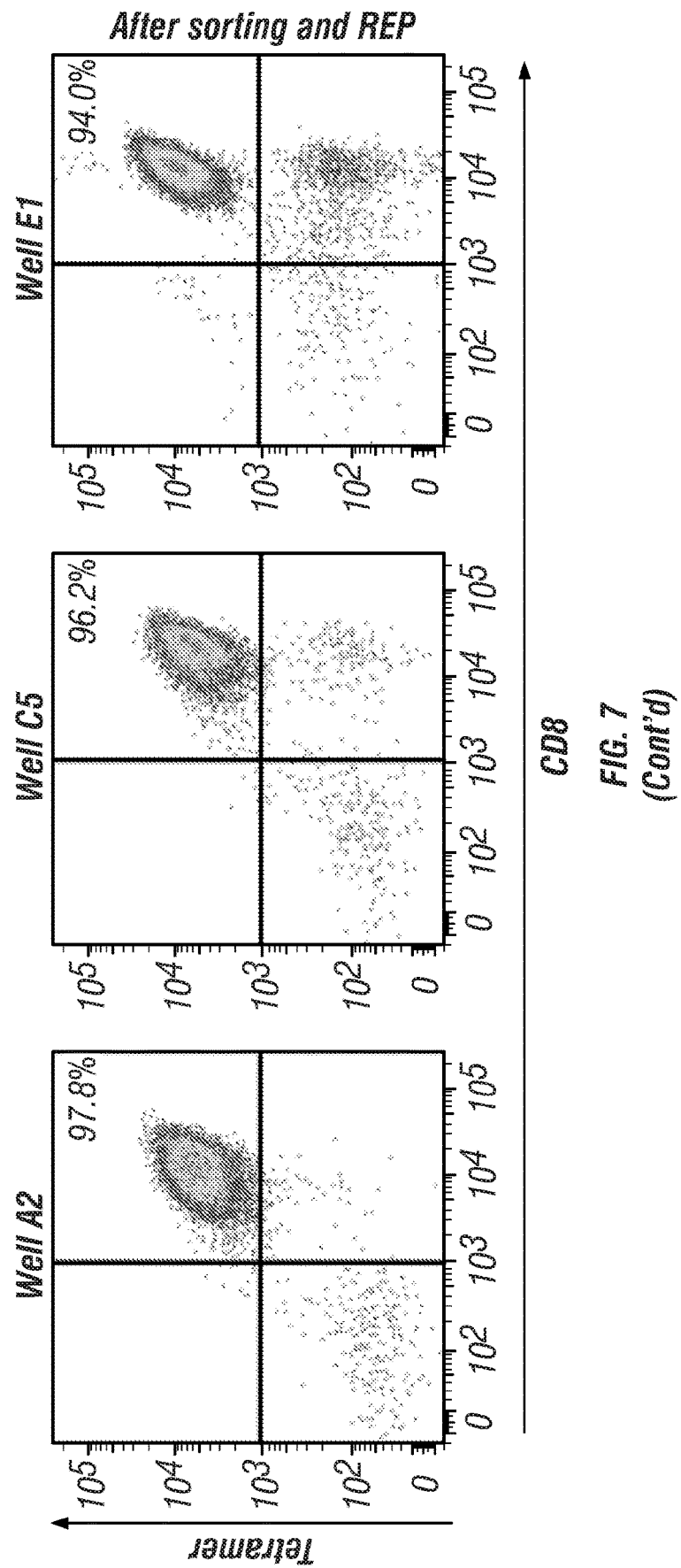

Example 3—Generation of MAGE-B2 HLA-A2 Restricted-Peptide (MB2-231)-Specific TCR-T Generation Additional MAGE-B2 specific T cell products were generated using MAGE-B2 peptide (GVYDGEEHSV; SEQ ID NO: 1) pulsed dendritic cells to stimulate the PBMC derived from the same healthy donor (FIG. 7). Small CD8+/Tetramer+ populations were observed in 3 wells of one 48 well plate after 2 stimulations. The 3 positive wells were sorted separately using tetramer guided sorting technology and underwent 1 or 2 rounds of expansions with REP. CD8 and tetramer staining of the final products is shown in FIG. 7.

Figure 8A:
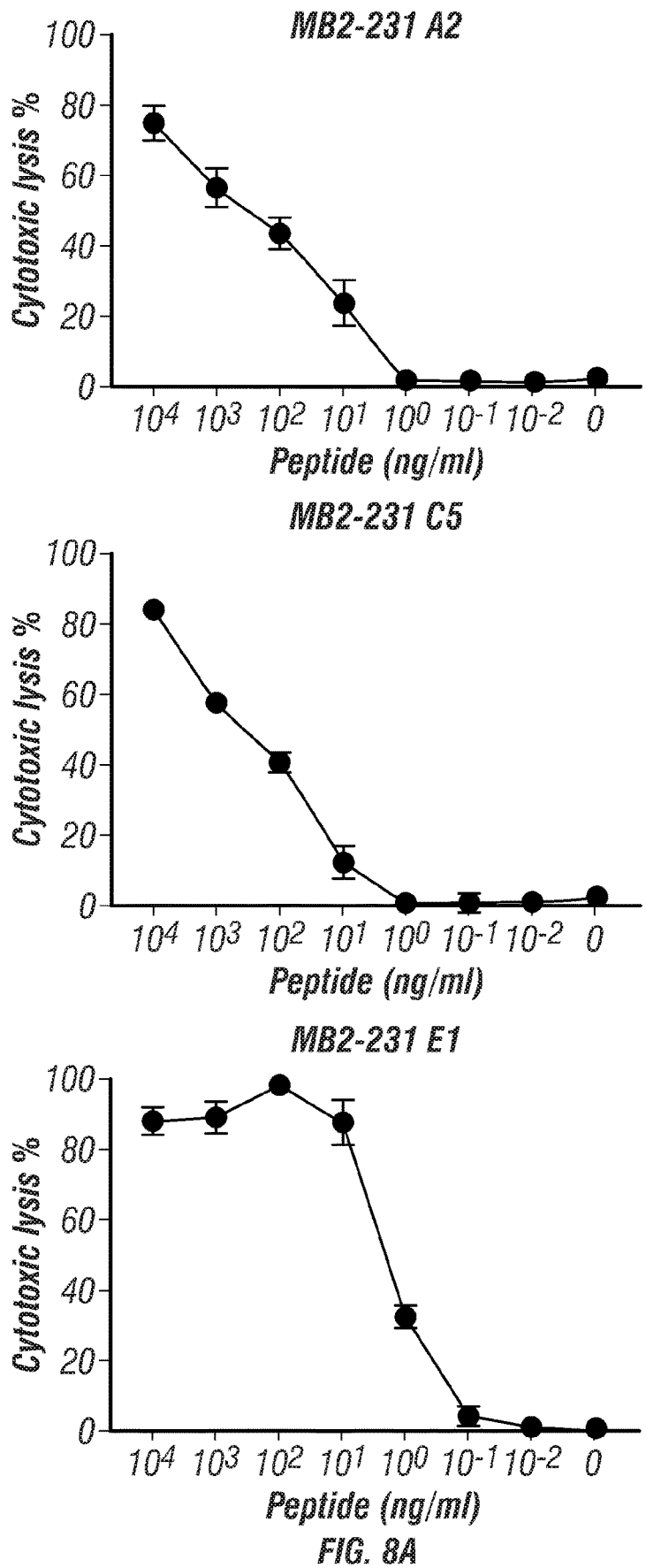
FIGS. 8A-8E: Functional avidity of MAGE-B2 specific T cells.
Figure 8B:
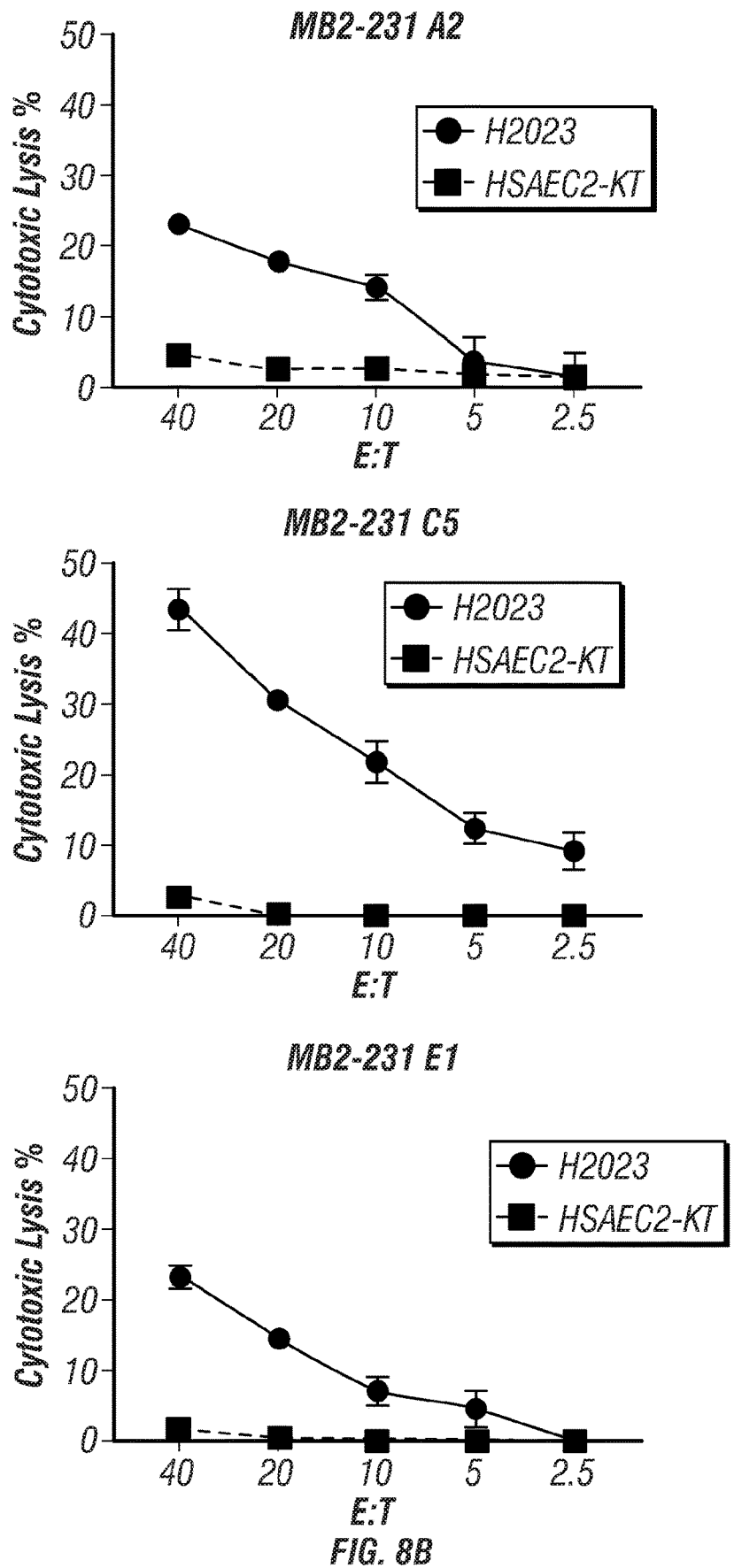
Figure 8C:
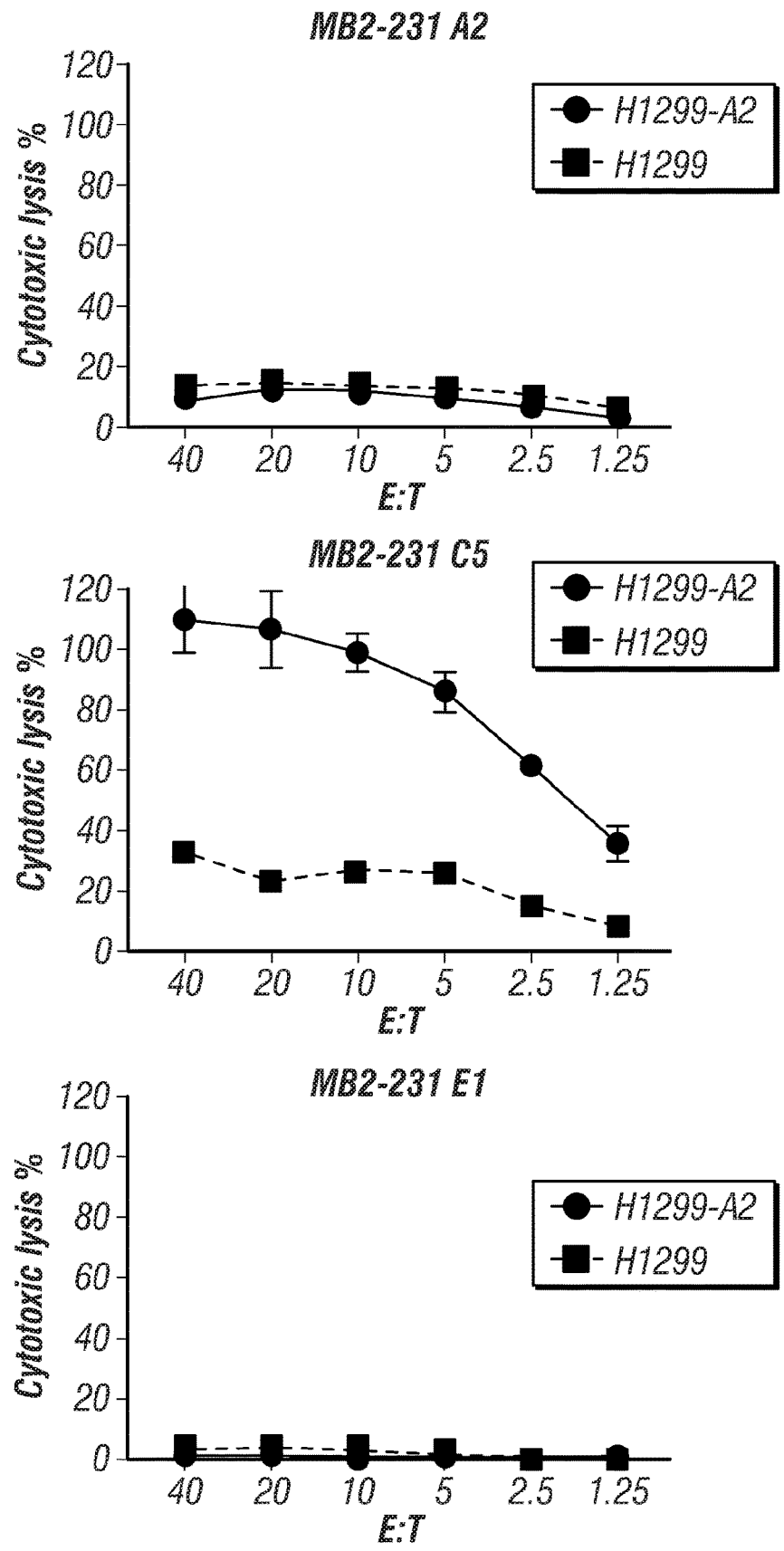
Figure 8D:
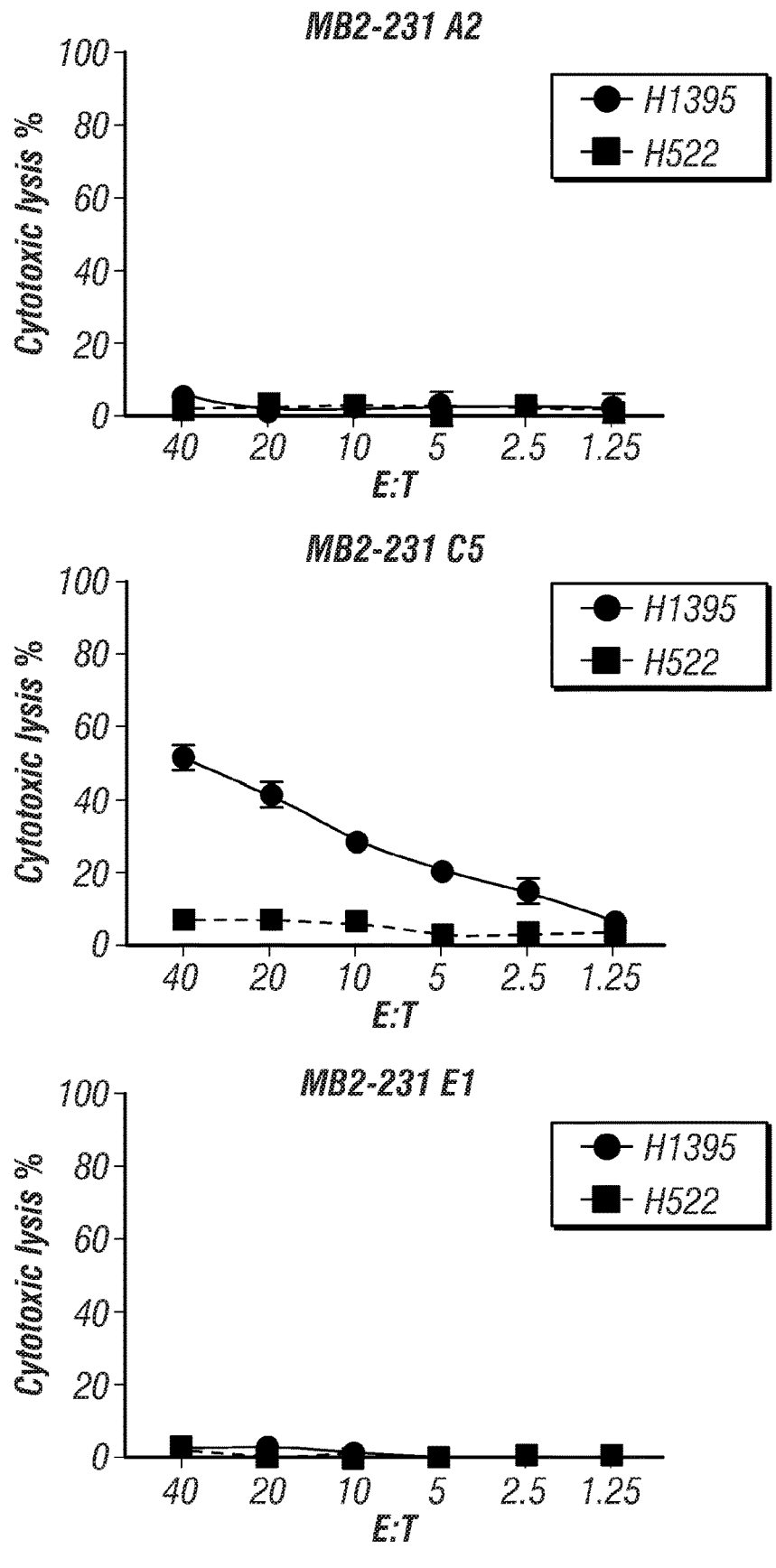
Figure 8E:
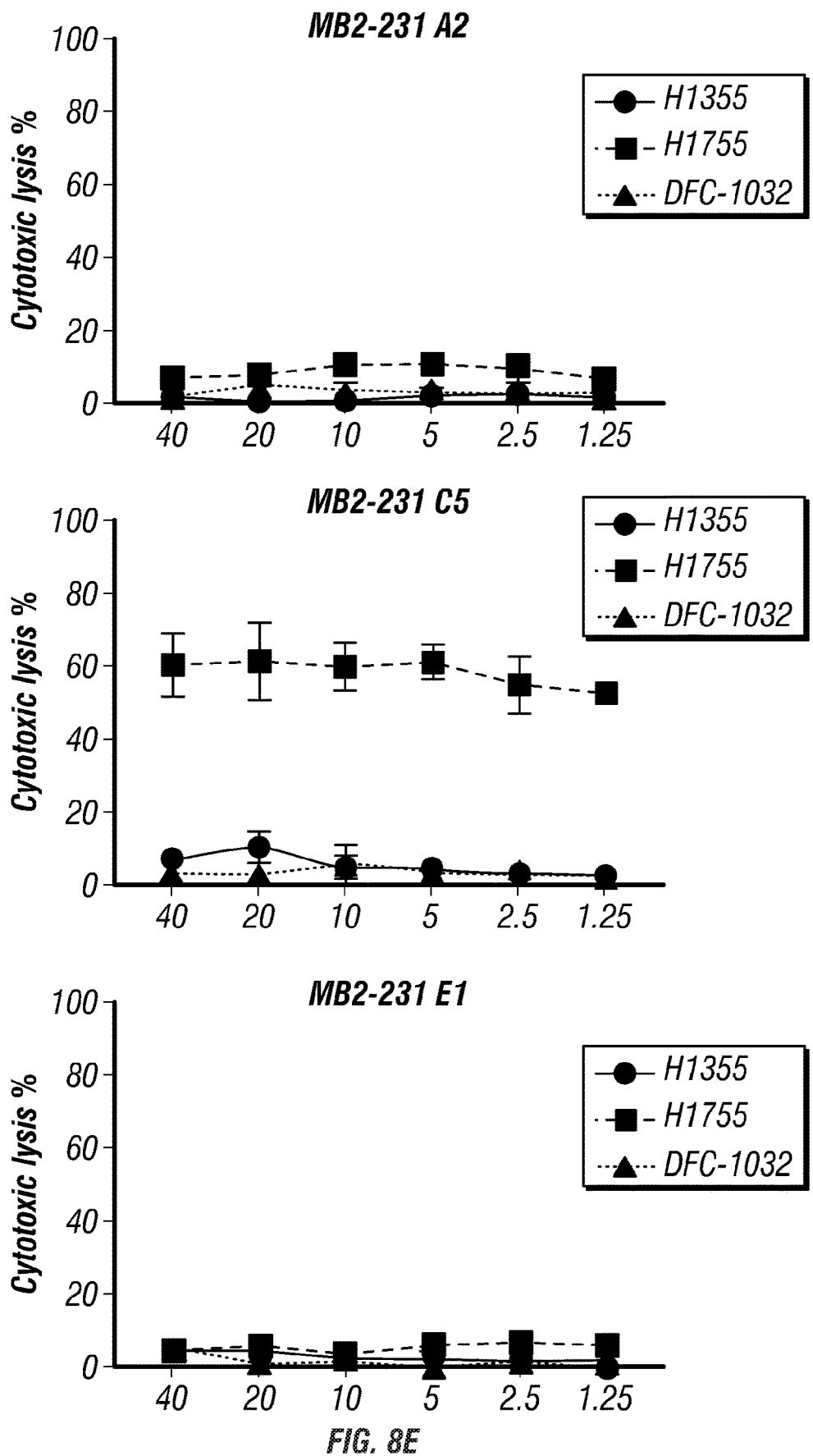

The functional avidity of 3 MAGE-B2 specific CTL cell lines was shown by the lysis of T2 cell lines pulsed with various concentrations of MAGE-B2 peptide (GVYDGEEHSV; SEQ ID NO: 1) with an effector to target (E:T) ratio of 20:1. The cytotoxicity was detected with the standard 51Cr release assay (FIG. 8A). The cytotoxicity of 3 MAGE-B2 specific CTL cell lines against lung cancer cell line H2023 (HLA-A*0201+, MAGE-B2+) and normal lung cell line HSAEC2-KT (HLA-A*0201+, MAGE-B2−) were also assessed (FIG. 8B). The lung cancer cell line H2023 and the normal lung cell line HSAEC2-KT were co-cultured with the MAGE-B2 TCR-T cells at different E:T ratios. The killing activity was detected with the standard 51Cr release assay. It was observed that all 3 MAGE-B2 specific CTL cell line were specifically cytotoxic to the lung cancer cell line H2023 (FIG. 8B). The cytotoxicity of 3 MAGE-B2 specific CTL cell lines against other lung cancer cell lines H1299 (HLA-A*0201−, MAGE-B2+), H1299-A2 (HLA-A*0201 forced expressing, MAGE-B2+), H1395 (HLA-A*0201+, MAGE-B2+), H522 (HLA-A*0201+, MAGE-B2−), H1355 (HLA-A*0201+, MAGE-B2−), H1755 (HLA-A*0201+, MAGE-B2+) and DFC-1032 (HLA-A*0201+, MAGE-B2−) were further assessed (FIG. 8C, 8D, 8E).

Figure 9A:
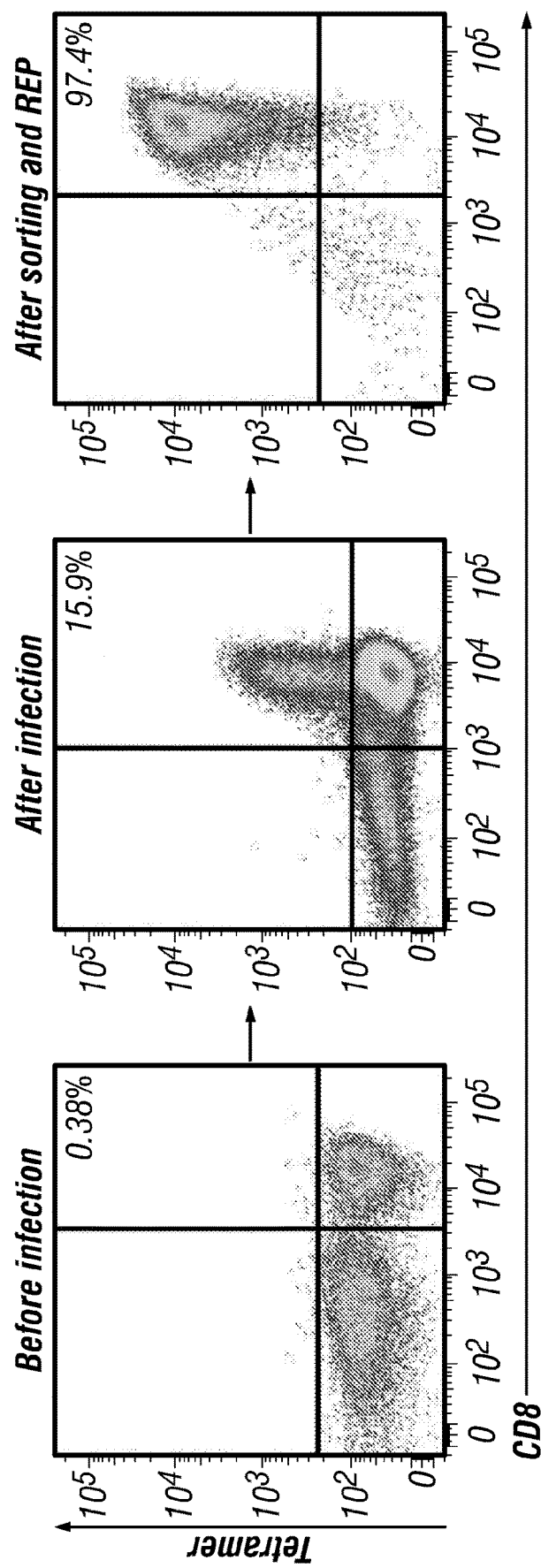
FIGS. 9A-9E: Generation and functional avidity of MAGE-B2 TCR-T.
Figure 9B:
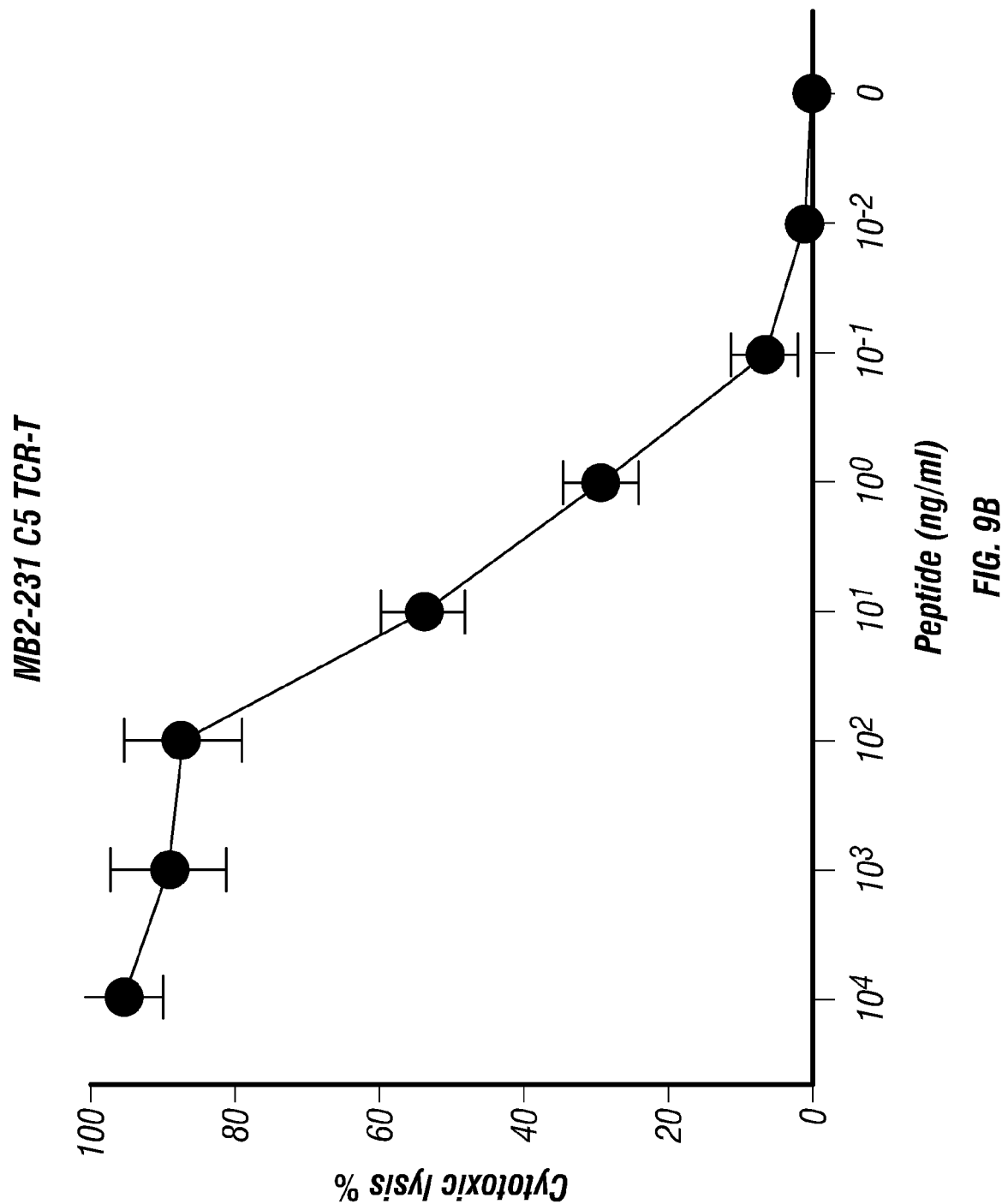
Figure 9C:
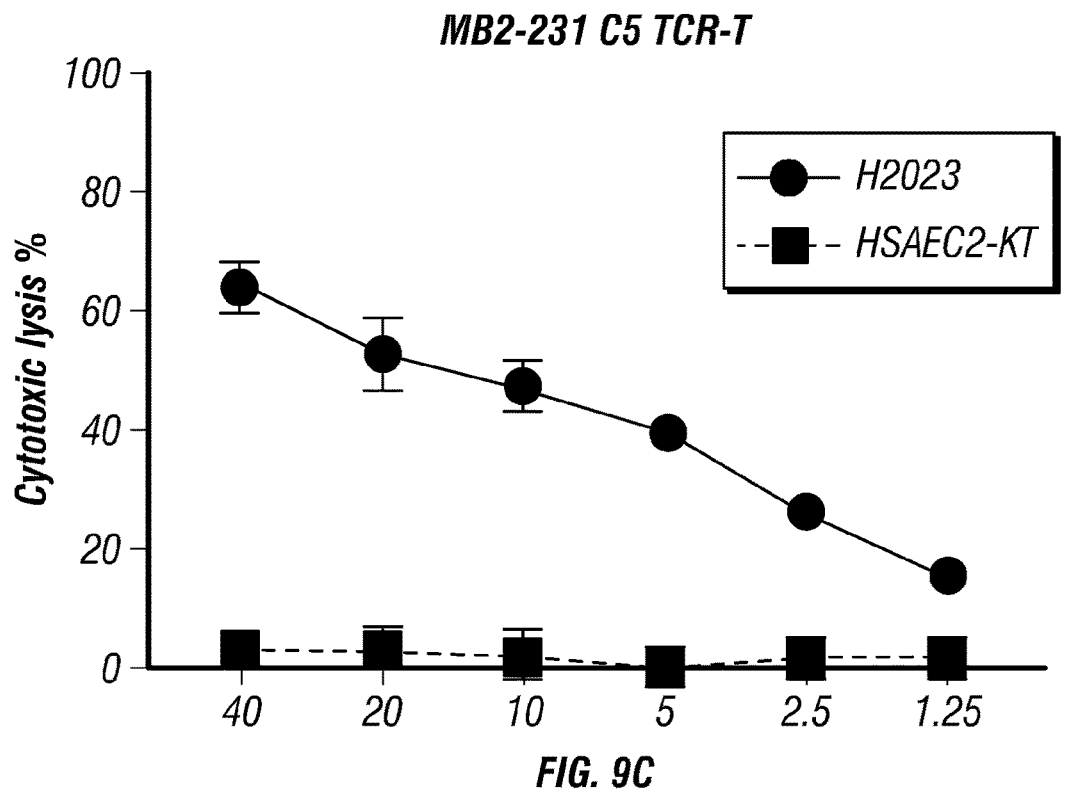
Figure 9D:
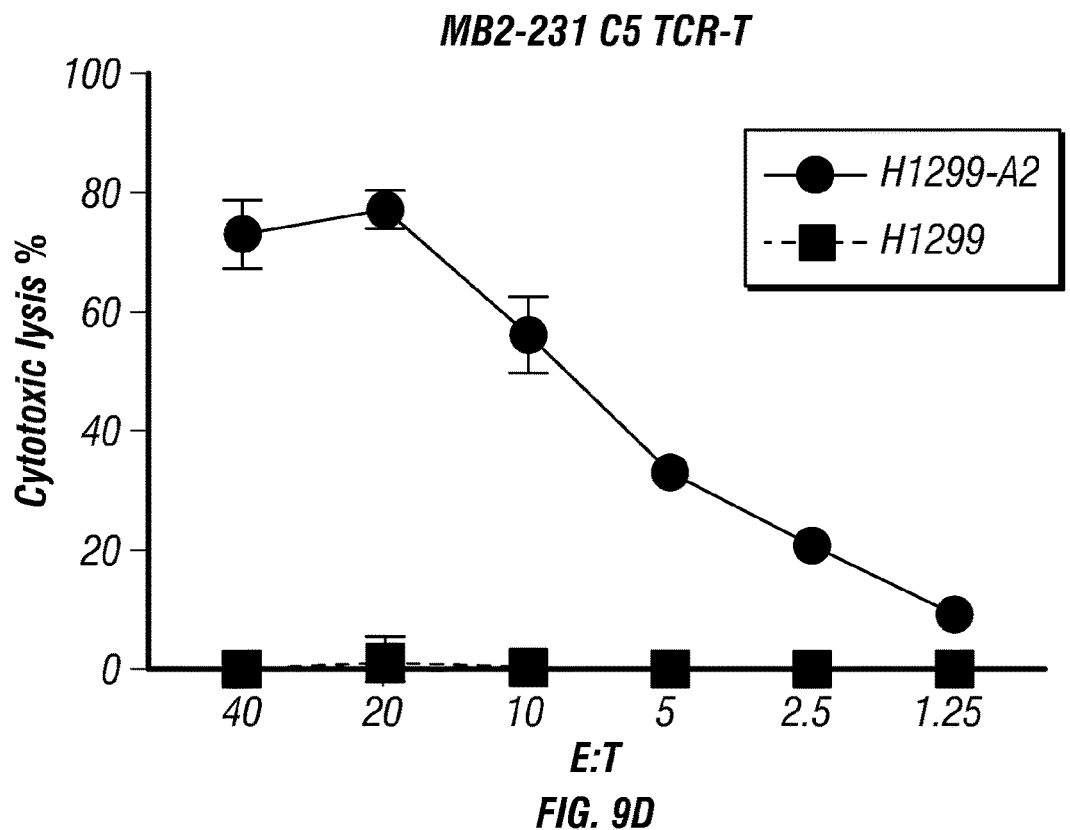
Figure 9E:
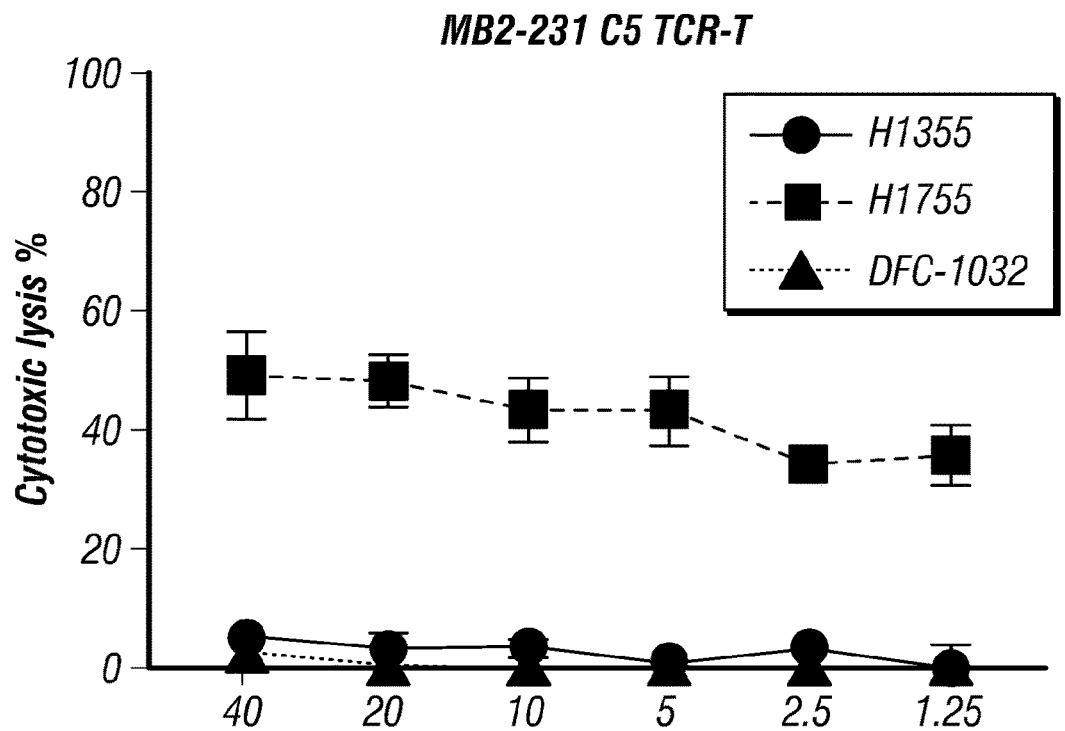
Figure 9E:
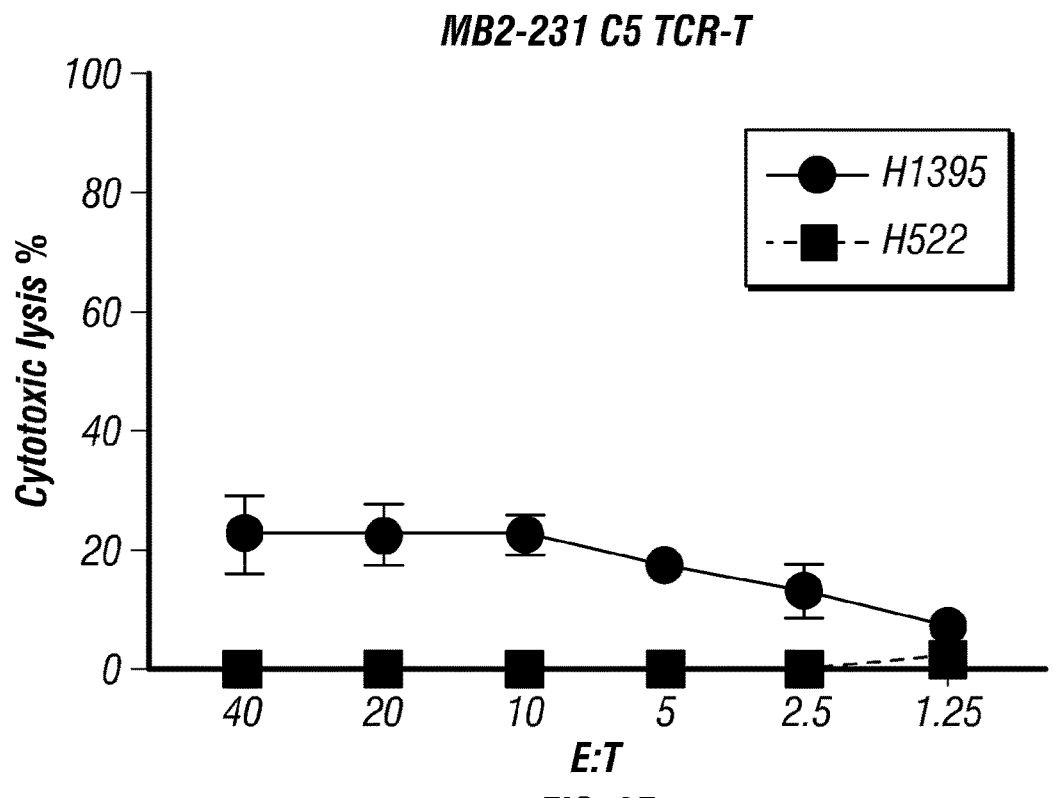

To generate MAGE-B2 TCR engineered T cells (TCR-T), the TCR from the MAGE-B2 CTL cell line C5 was cloned out and inserted into the retrovirus vector pMSGV1. A linker fragment containing a Furin cleavage site, a SGSG linker and a P2A cleavage site was inserted between the TCR-β chain and TCR-α chain to guarantee that both chain were expressed equally under the MSCV promoter. The recombinant retrovirus was generated by co-transfection of the retrovirus vector and an envelope vector RD114 into the package cell line Phoenix-GP. Two to three days after transfection, the supernatant containing the retrovirus was used to infect the allogeneic HLA-A*0201+healthy donor's PBMCs which were activated for two days with 50 ng/mg OKT3 and 300 U/ml IL-2 stimulation. After 5 days, a clear CD8+Tetramer+ population was detected by flow cytometry (FIG. 9A). The CD8+tetramer+ population was sorted using tetramer guided sorting technology and expanded with REP. CD8 and tetramer staining of the final products is shown in FIG. 9A. The functional avidity of MAGE-B2 TCR-T was shown by the lysis of T2 cell lines pulsed with various concentrations of MAGE-B2 peptide (GVYDGEEHSV; SEQ ID NO: 1) with an effector to target (E:T) ratio of 20:1. The cytotoxicity was detected with the standard 51Cr release assay (FIG. 9B). The cytotoxicity of MAGE-B2 TCR-T against lung cancer cell line H2023 (HLA-A*0201+, MAGE-B2+) and normal lung cell line HSAEC2-KT (HLA-A*0201+, MAGE-B2−) were also assessed (FIG. 9C). The cytotoxicity of MAGE-B2 TCR-T against other lung cancer cell lines H1299 (HLA-A*0201−, MAGE-B2+), H1299-A2 (HLA-A*0201 forced expressing, MAGE-B2+), H1395 (HLA-A*0201+, MAGE-B2+), H522 (HLA-A*0201+, MAGE-B2−), H1355 (HLA-A*0201+, MAGE-B2−), H1755 (HLA-A*0201+, MAGE-B2+) and DFC-1032 (HLA-A*0201+, MAGE-B2−) were further assessed (FIG. 9D, 9E).

Figure 10A:
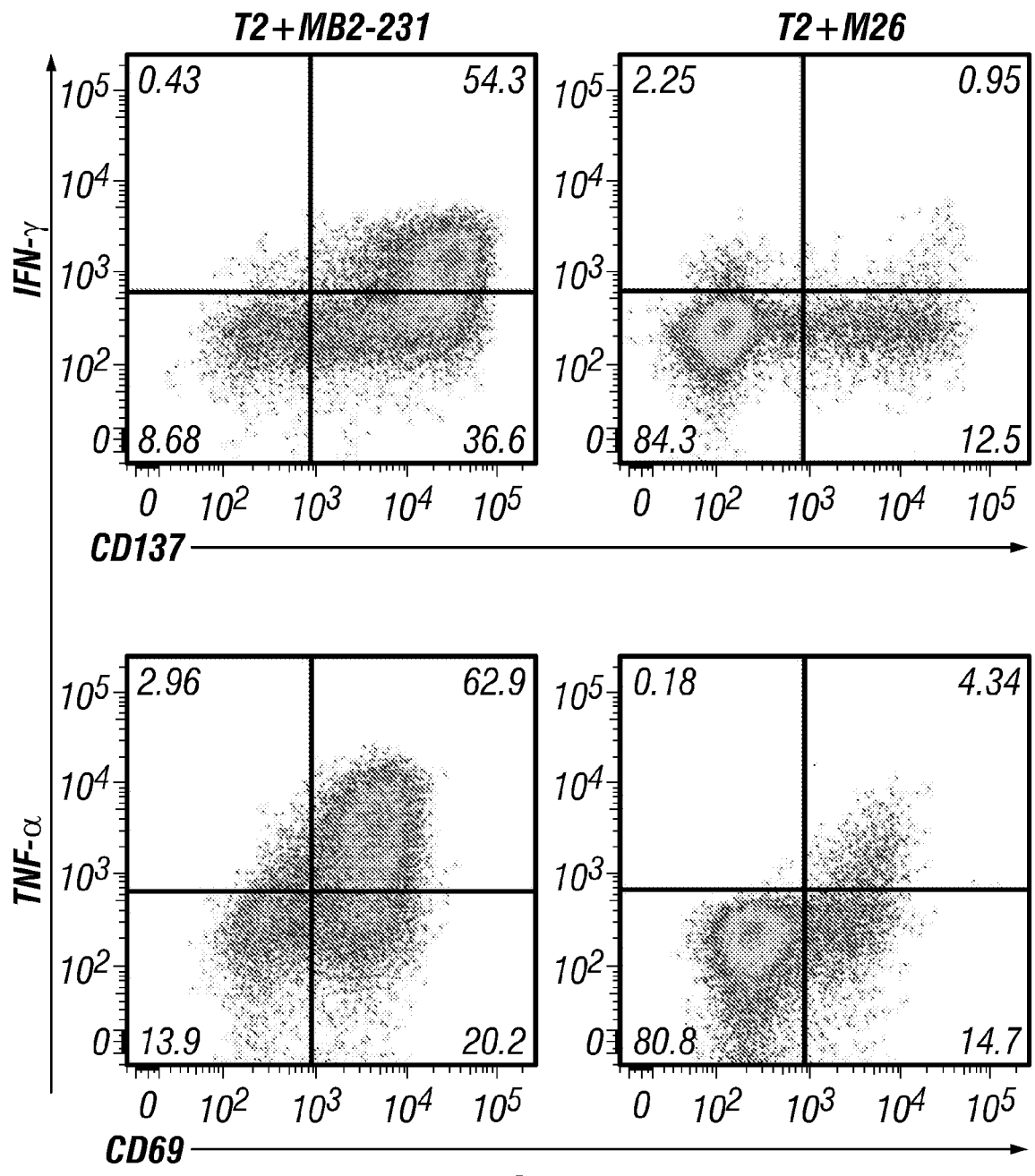
FIGS. 10A-10C: Functional detection of MB2-231 C5 TCR-T with intracellular cytokine staining (ICS) assay. The MB2-231 C5 TCR-T was co-cultured with T2 pulsed with MB2-231 peptide/M26 peptide, tumor cell line H2023 (MAGE-B2$^+$, HLA-A2$^+$), normal lung cell line HSAEC2-KT (MAGE-B2$^-$, HLA-A2$^+$), tumor cell line H1395 (MAGE-B2$^+$, HLA-A2$^+$), H522 (MAGE-B2$^+$, HLA-A2$^+$), H1299-A2 (MAGE-B2$^+$, HLA-A2 forced expressing), H1299 (MAGE-B2$^+$, HLA-A2$^-$), H1355 (MAGE-B2$^+$, HLA-A2$^+$), H1755 (MAGE-B2$^+$, HLA-A2±) and DFC-1032 (MAGE-B2$^+$, HLA-A2±) at E:T=10:1 ratio. After overnight, the TCR pathway down-stream activated marker, CD137, CD69, IFN-γ and TNF-α were detected with ICS assay. M26 peptide pulsed T2, HSAEC2-KT, H1299 were as negative control. After co-culturing with T2 pulsed with MB2-231 peptide, H2023, H1395, H1299-A2, H1755, the level of CD137, CD69, IFN-γ and TNF-α were significantly enhanced compared with negative control.
Figure 10A:
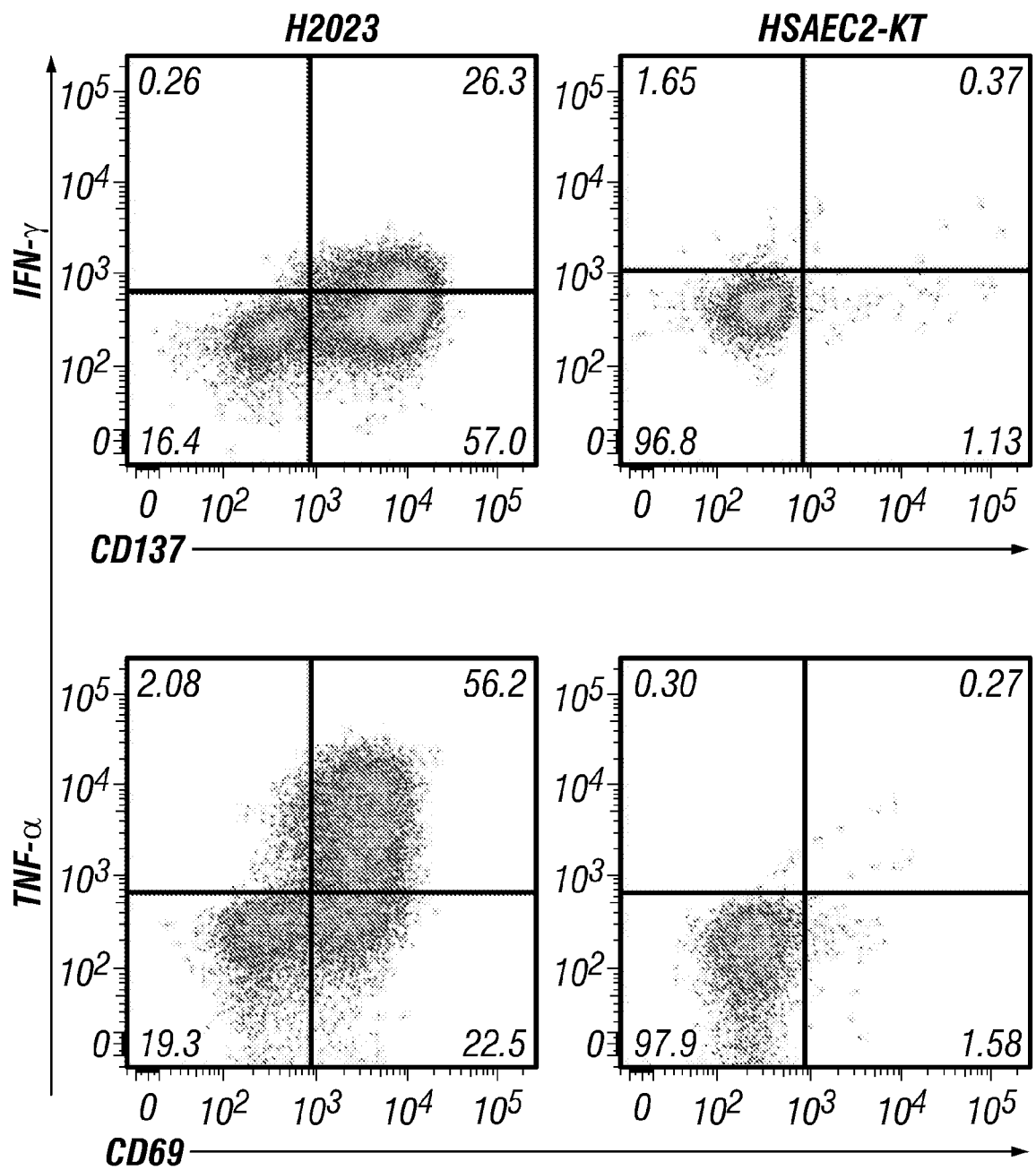
Figure 10B:
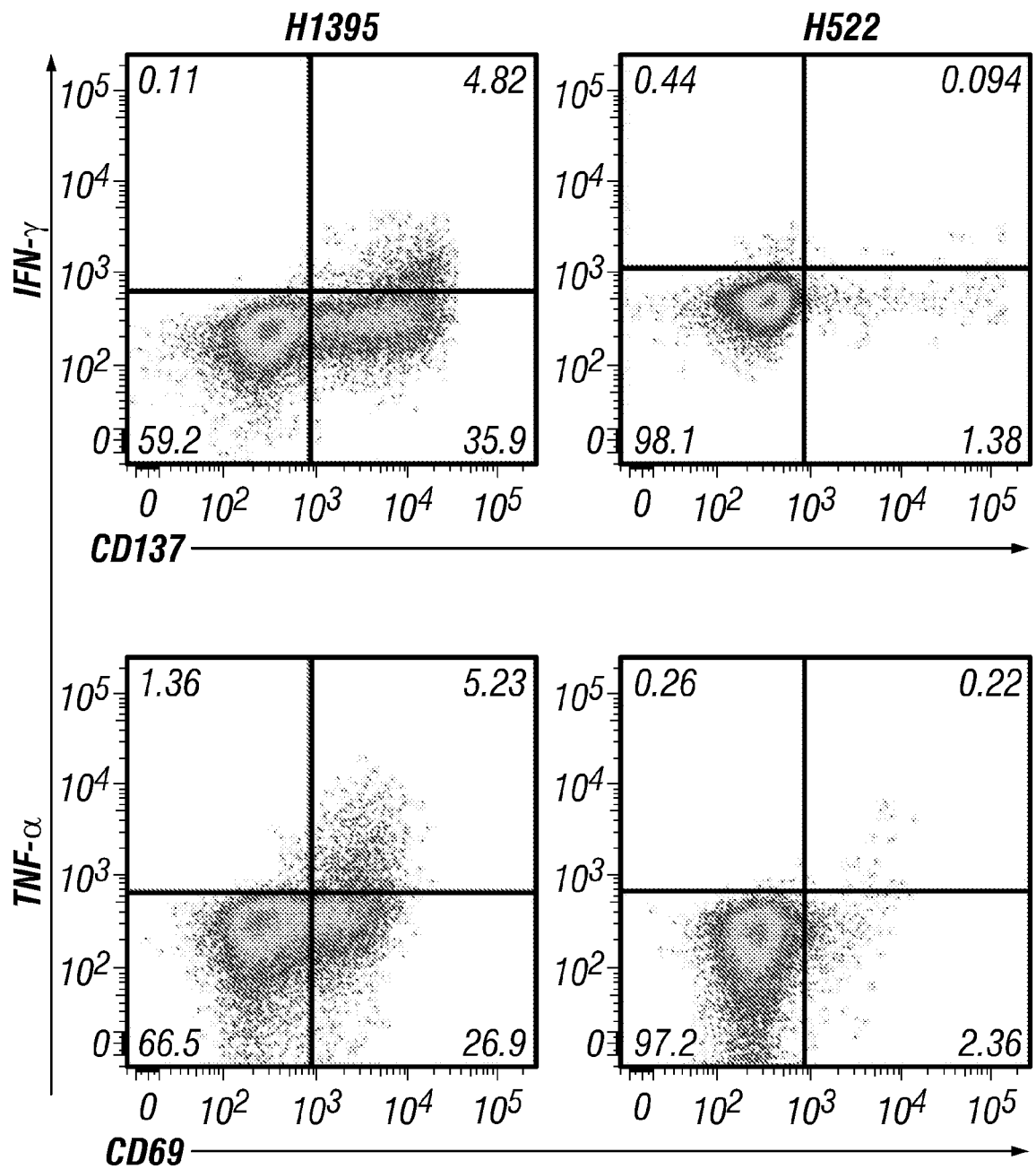
Figure 10B:
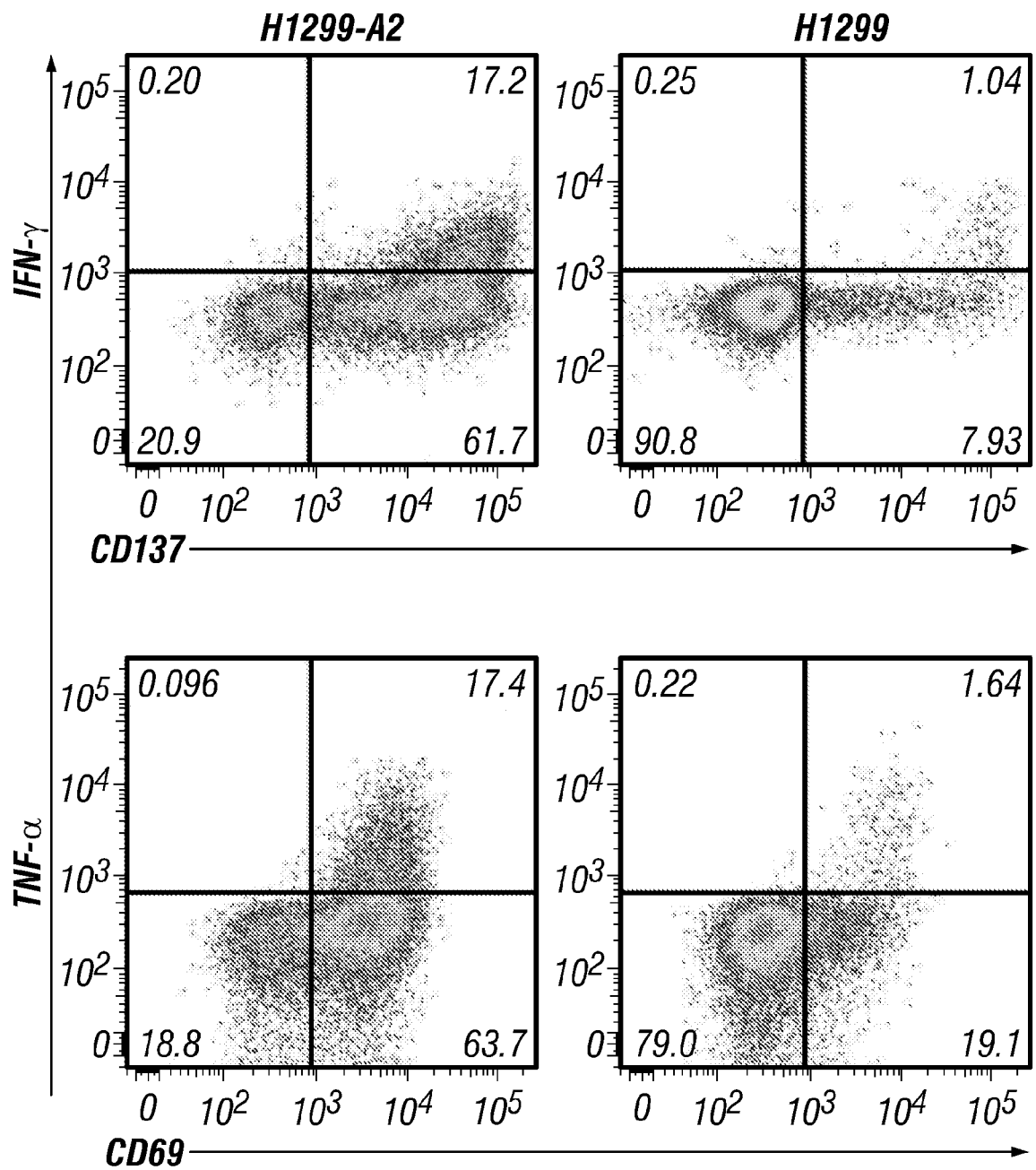
Figure 10C:
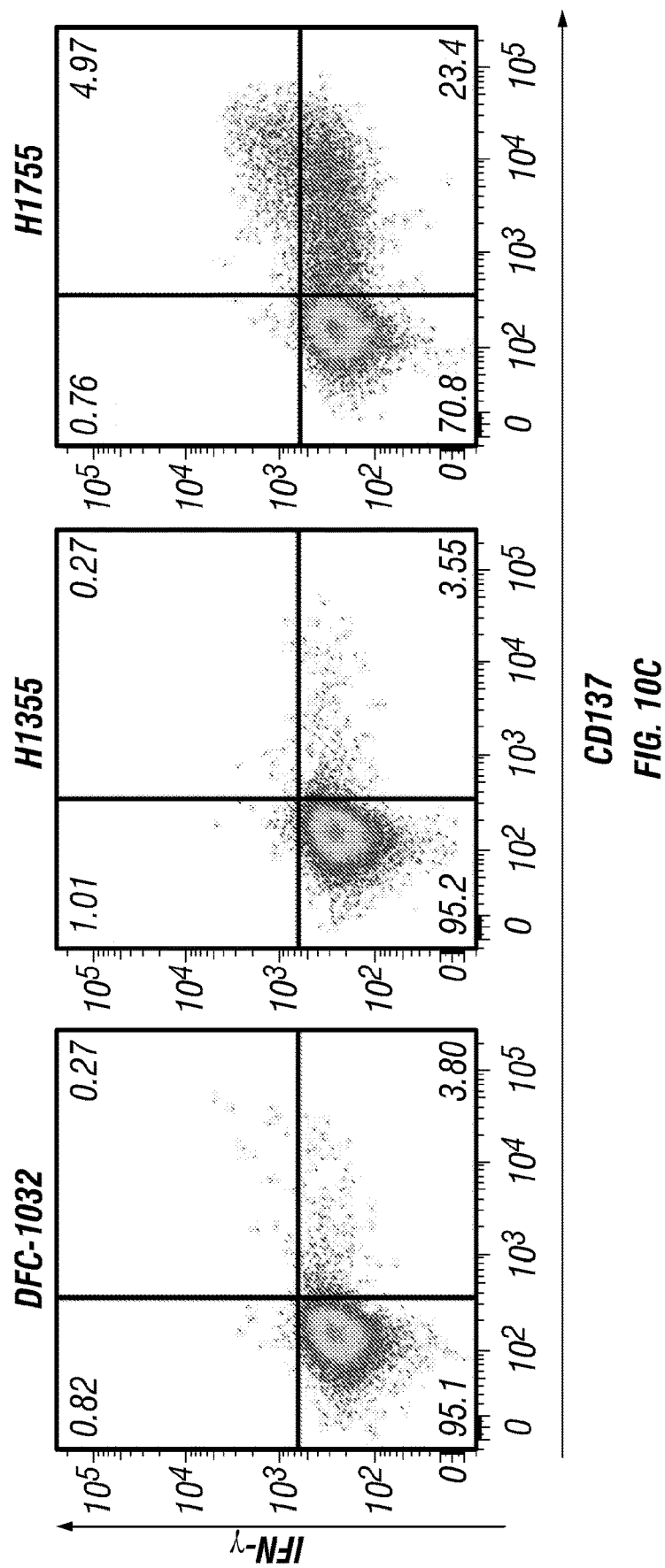
Figure 10C:
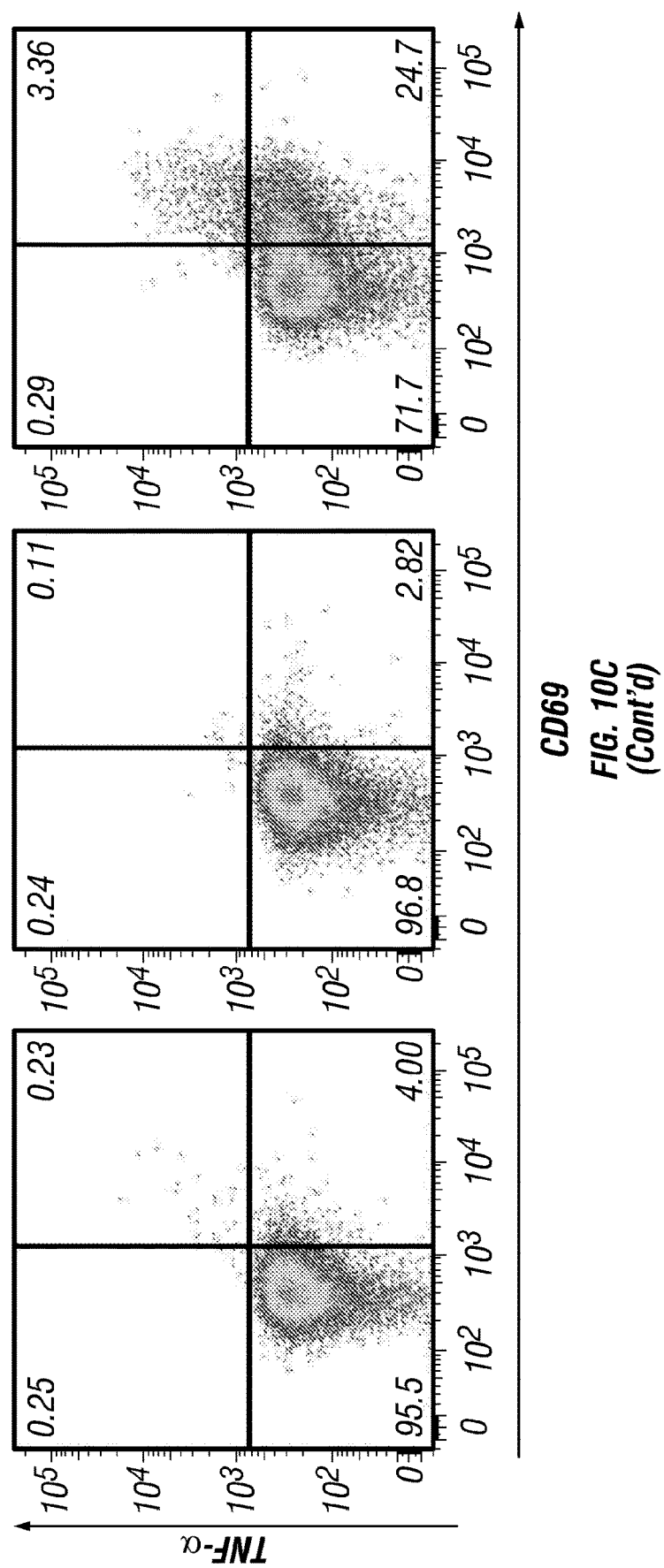

Finally, the MAGE-B2 TCR-T cells were functionally characterized by intracellular cytokine staining (ICS). The MAGE-B2 TCR-T cell line was co-cultured with the T2 pulsed with MAGE-B2 peptide (GVYDGEEHSV; SEQ ID NO: 1), as well as T2 pulsed with MART-1 peptide M26 (as control) (FIG. 10A). The response of MAGE-B2 specific TCR-T to lung cancer cell line H2023, normal lung cell line HSAEC2-KT (as control) was also assessed (FIG. 10A). Furthermore, other lung cancer cell lines, H1395, H522, H1299, H1299-A2, DFC-1032, H1355 and H1755, were also used as target to evaluate the function and specificity of MAGE-B2 TCR-T (FIG. 10B, 10C). The cytokine releasing of IFN-γ, TNF-α, and up-regulation of antigen specific response markers CD137 and CD69 of MAGE-B2 TCR-T cell line were detected with ICS.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within

REFERENCES

The following references, to the extent that they provide exemplary procedural or other details supplementary to those set forth herein, are specifically incorporated herein by reference.

Barnea et al., *Eur J Immunol*, 32(1):213-22, 2002.
Remington: The Science and Practice of Pharmacy, 22nd Edition, Pharmaceutical Press, 2012.
Shraibman et al., *Mol Cell Proteomics*, 15(9):3058-70, 2016.

What is claimed is:

1. An isolated T cell receptor (TCR) capable of binding an antigenic peptide derived from the Melanoma-associated Antigen B2 (MAGE-B2), comprising:
   (a) a TCR alpha polypeptide having at least 90% identity to the sequence of SEQ ID NO: 3 and a TCR beta polypeptide having at least 90% identity to the sequence of SEQ ID NO: 5, wherein the TCR alpha polypeptide comprises a CDR1 sequence with at least 95% identity to SEQ ID NO: 7, a CDR2 sequence with at least 95% identity to SEQ ID NO: 9, and a CDR3 sequence with at least 95% identity to SEQ ID NO: 11 and the TCR beta polypeptide comprises a CDR1 sequence with at least 95% identity to SEQ ID NO: 13, a CDR2 sequence with at least 95% identity to SEQ ID NO: 15, and CDR3 sequence with at least 95% identity to SEQ ID NO: 17; or
   (b) a TCR alpha polypeptide having at least 90% identity to the sequence of SEQ ID NO: 19 and a TCR beta polypeptide having at least 90% identity to the sequence of SEQ ID NO: 21, wherein the TCR alpha polypeptide comprises a CDR1 sequence with at least 95% identity to SEQ ID NO: 23, a CDR2 sequence with at least 95% identity to SEQ ID NO: 25, and a CDR3 sequence with at least 95% identity to SEQ ID NO: 27 and the TCR beta polypeptide comprises a CDR1 sequence with at least 95% identity to SEQ ID NO: 29, a CDR2 sequence with at least 95% identity to SEQ ID NO: 31, and CDR3 sequence with at least 95% identity to SEQ ID NO: 33.

2. The TCR of claim 1, wherein the antigenic peptide is HLA-A2 restricted.

3. The TCR of claim 2, wherein the antigenic peptide is HLA-A*0201 restricted.

4. The TCR of claim 1, wherein the TCR alpha polypeptide comprises a CDR1 with the sequence of SEQ ID NO: 7, a CDR2 with the sequence of SEQ ID NO: 9, and a CDR3 with the sequence of SEQ ID NO: 11 and the TCR beta polypeptide comprises a CDR1 with the sequence of SEQ ID NO: 13, a CDR2 with the sequence of SEQ ID NO: 15, and CDR3 with the sequence of SEQ ID NO: 17.

5. The TCR of claim 1, wherein the TCR alpha polypeptide has at least 95% identity to the sequence of SEQ ID NO: 3 and the TCR beta polypeptide has at least 95% identity to the sequence of SEQ ID NO: 5.

6. The TCR of claim 1, wherein the TCR alpha polypeptide comprises the sequence of SEQ ID NO: 3 and the TCR beta polypeptide comprises the sequence of SEQ ID NO: 5.

7. The TCR of claim 1, wherein the TCR alpha polypeptide comprises a CDR1 with the sequence of SEQ ID NO: 23, a CDR2 with the sequence of SEQ ID NO: 25, and a CDR3 with the sequence of SEQ ID NO: 27 and the TCR beta polypeptide comprises a CDR1 with the sequence of SEQ ID NO: 29, a CDR2 with the sequence of SEQ ID NO: 31, and a CDR3 with the sequence of SEQ ID NO: 33.

8. The TCR of claim 1, wherein the TCR alpha polypeptide has at least 95% identity to the sequence of SEQ ID NO: 19 and the TCR beta polypeptide has at least 95% identity to the sequence of SEQ ID NO: 21.

9. The TCR of claim 1, wherein the TCR alpha polypeptide comprises the sequence of SEQ ID NO: 19 and the TCR beta polypeptide comprises the sequence of SEQ ID NO: 21.

10. The TCR of claim 1, wherein the TCR is a soluble TCR lacking a transmembrane domain.

11. The TCR of claim 10, further comprising a detectable label.

12. The TCR of claim 10, further comprising a therapeutic agent.

13. A multivalent TCR complex comprising a plurality of TCRs according to claim 1.

14. A polypeptide comprising a TCR alpha polypeptide comprising a CDR1 with the sequence of SEQ ID NO: 7, a CDR2 with the sequence of SEQ ID NO: 9, and a CDR3 with the sequence of SEQ ID NO: 11 and/or a TCR beta polypeptide comprising a CDR1 with the sequence of SEQ ID NO: 13, a CDR2 with the sequence of SEQ ID NO: 15, and CDR3 with the sequence of SEQ ID NO: 17.

15. A polypeptide comprising a TCR alpha polypeptide comprising a CDR1 with the sequence of SEQ ID NO: 23, a CDR2 with the sequence of SEQ ID NO: 25, and a CDR3 with the sequence of SEQ ID NO: 27 and/or a TCR beta polypeptide comprising a CDR1 with the sequence of SEQ ID NO: 29, a CDR2 with the sequence of SEQ ID NO: 31, and CDR3 with the sequence of SEQ ID NO: 33.

16. An expression vector comprising a polynucleotide sequence encoding the TCR of claim 1.

17. A method for engineering a MAGE-B2-specific immune cell comprising contacting said immune cell with the expression vector of claim 16.

18. A composition comprising a therapeutically effective amount of MAGE-B2-specific cells produced according to claim 17 for the treatment of cancer in a subject.

* * * * *

UNITED STATES PATENT AND TRADEMARK OFFICE
CERTIFICATE OF CORRECTION

PATENT NO. : 12,202,877 B2
APPLICATION NO. : 17/048748
DATED : January 21, 2025
INVENTOR(S) : Yee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1129 days.

Signed and Sealed this
Nineteenth Day of August, 2025

Coke Morgan Stewart
*Acting Director of the United States Patent and Trademark Office*